United States Patent
Astles et al.

(10) Patent No.: US 7,148,236 B2
(45) Date of Patent: Dec. 12, 2006

(54) MODULATORS OF ACETYLCHOLINE RECEPTORS

(75) Inventors: Peter Charles Astles, Basingstoke (GB); Stephen Richard Baker, Basingstoke (GB); Rowena Villanueva Cube, San Diego, CA (US); Jose Antonio Martinez-Perez, Alcoberidas-Madrid (ES); Ana Isabel Mateo Herranz, Alcobendas-Madrid (ES); Jean Michel Vernier, San Diego, CA (US); Colin Peter Dell, Basingstoke (GB); Sonia Gutierrez, Alcobendas-Madrid (ES); Lourdes Prieto, Alcobendas-Madrid (ES); Martine Keenan, Basingstoke (GB); Adam Jan Sanderson, Basingstoke (GB); Colin William Smith, Basingstoke (GB)

(73) Assignee: Merck & Co., Inc., Rahway, NJ (US)

( * ) Notice: Subject to any disclaimer, the term of this patent is extended or adjusted under 35 U.S.C. 154(b) by 184 days.

(21) Appl. No.: 10/500,516

(22) PCT Filed: Jul. 29, 2002

(86) PCT No.: PCT/US02/21296

§ 371 (c)(1),
(2), (4) Date: Jun. 29, 2004

(87) PCT Pub. No.: WO03/062235

PCT Pub. Date: Jul. 31, 2003

(65) Prior Publication Data

US 2005/0182088 A1    Aug. 18, 2005

Related U.S. Application Data

(60) Provisional application No. 60/350,152, filed on Jan. 17, 2002.

(51) Int. Cl.
*A01N 43/42* (2006.01)
*A61K 31/44* (2006.01)
*C07D 451/02* (2006.01)
*C07D 451/04* (2006.01)
*C07D 451/06* (2006.01)

(52) U.S. Cl. ............... 514/304; 546/127; 546/126
(58) Field of Classification Search ............ 546/126, 546/198, 127; 514/304, 323, 324, 312
See application file for complete search history.

(56) References Cited

U.S. PATENT DOCUMENTS

| | | | | |
|---|---|---|---|---|
| 5,306,723 A | * | 4/1994 | Chenard | 514/304 |
| 5,498,610 A | * | 3/1996 | Chenard | 514/222.8 |
| 6,046,213 A | * | 4/2000 | Chenard et al. | 514/327 |

FOREIGN PATENT DOCUMENTS

| | | |
|---|---|---|
| EP | 0 398 578 B1 | 3/1997 |
| JP | 04054181 * | 2/1992 |
| WO | 96/37226 * | 11/1996 |
| WO | WO 96/37226 | 11/1996 |
| WO | WO 97/19059 | 5/1997 |
| WO | WO 99/32117 | 7/1999 |
| WO | WO 00/44755 | 8/2000 |
| WO | WO 01/19817 A2 | 3/2001 |

OTHER PUBLICATIONS

Abreo et al., "Novel 3-pyridyl ethers with subnanomolar affinity for central neuronal nicotinic acetylcholine receptors", Journal of Medicine Chemistry, vol. 39, pp. 817-825.*
Hu et al., "Regional vascular and cardiac responses to systemic neuropeptide-Y in normal and diabetic rats", Peptieds, vol. 18, pp. 809-815.*
Kraiss, G. et al., Stereospecific Methods of Forming Ethers by Nucleophilic Reactions of 3α-Substituted Tropanes, *The Journal of Organic Chemistry*, Jun. 1968, 2601-2603, vol. 33, No. 6.
Elliott, R.L.et al., 2-(Aryloxymethyl) Azacyclic Analogues as Novel Nicotinic Acetylcholine Receptor (nAChR) Ligands, *Bioorganic & Medicinal Chemistry Letters*, 1996, 2283-2288, vol. 6, No. 19.
Radl S. et al., Synthesis and Analgesic Activity of Some Side-Chain Modified Anpirtoline Derivatives, *Arch. Pharm. Pharm. Med. Chem.*, 2000, 107-112, vol. 333.

* cited by examiner

*Primary Examiner*—Thomas McKenzie
*Assistant Examiner*—Niloofar Rahmani
(74) *Attorney, Agent, or Firm*—John C. Todaro; Melvin Winokur

(57) ABSTRACT

The present invention relates to compounds that modulate neurotransmission by promoting the release of neurotransmitters such as acetylcholine, dopamine and norepinephrine. More particularly, the present invention relates to thio-bridged aryl compounds that are capable of modulating acetylcholine receptors and pharmaceutical compositions comprising such compounds. The compounds disclosed are useful for the treatment of dysfunctions of the central and autonomic nervous systems.

62 Claims, No Drawings

MODULATORS OF ACETYLCHOLINE RECEPTORS

This is the national phase application, under 35 USC 371, for PCT/US02/21296, filed 29 Jul. 2002, which claims the benefit, under 35 USC 119(e), of U.S. provisional application No. 60/350,152, filed 17 Jan. 2002.

The present invention relates to compounds that modulate neurotransmission by promoting the release of neurotransmitters such as acetylcholine, dopamine and norepinephrine. More particularly, the present invention relates to thiobridged aryl compounds that are capable of modulating acetylcholine receptors and pharmaceutical compositions comprising such compounds.

Acetylcholine receptors modulate the release of neurotransmitters such as for example dopamine, norepinephrine, acetylcholine, and serotonin from different brain regions. By such action, acetylcholine receptors participate in the modulation of neuroendocrine function, respiration, mood, motor control and function, focus and attention, concentration, memory and cognition, and the mechanisms of substance abuse. Ligands for acetylcholine receptors have been demonstrated to have effects on attention, cognition, appetite, substance abuse, memory, extrapyramidal function, cardiovascular function, pain, and gastrointestinal motility and function. The distribution of acetylcholine receptors that bind nicotine, i.e., nicotinic acetylcholine receptors, is widespread in the brain, including being found in the basal ganglia, limbic system, cerebral cortex and mid- and hindbrain nuclei. In the periphery, their distribution includes being in muscle, autonomic ganglia, the gastrointestinal tract and the cardiovascular system.

Acetylcholine receptors have been shown to be decreased in the brains of patients suffering from Alzheimer's disease or Parkinson's disease, diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. Thus, there is a continuing need for compounds that can modulate the activity of acetylcholine receptors.

Nicotinic acetylcholine receptors (nAChRs) belong to the ligand gated ion channel family of neurotransmitter receptors. In neuronal and peripheral tissue, nAChRs possess a pentameric structure consisting of 5 protein subunits surrounding a central ion channel. Five neuromuscular subunits (α, β, γ, δ, ε), ten peripheral or neuronal α-subunits (α1 to α10), and three peripheral or neuronal β-subunits (β2 to β4) have been identified. These subunits combine to form pentameric receptors in three ways: first, with homomeric 5[α] stoichiometry, for example, α7 to α9; second, with heteromeric 2[α]3[β] stoichiometry, for example, combinations of α1 to α6 and β2 to β4 subunits; and third, the 2[α]1[β]1[δ]1[γ/δ] stoichiometry found in neuromuscular receptors.

Nicotine modulates multiple neuronal, peripheral and neuromuscular subtypes of nAChRs. While demonstrating beneficial effects in a number of neuronal diseases mediated by nAChRs, nicotine also demonstrates a number of undesirable side effects on cardiovascular, gastrointestinal and neuromuscular systems. It will be appreciated that there is a need for compounds that can selectively modulate a single or specific group of nAChRs.

It is desired to provide new compounds which selectively modulate the activity, of acetylcholine receptors. In particular, it is desired to provide compounds that are capable of acting as selective modulators, preferably agonists, of beta 4 subtype nicotinic acetylcholine receptors. It is also desirable to provide a method of treatment of dysfunctions of the central and peripheral nervous systems to treat, for example, dementia, cognitive and conduct disorders including attention deficit hyperactivity disorder, neurodegenerative disorders, including Alzheimers disease, Parkinson's disease and other diseases in which degeneration leads to impaired functioning of the sensory or motor systems, extrapyramidal disorders associated with neuroleptic use, convulsive disorders, epilepsy, cardiovascular disorders, endocrine disorders, psychotic disorders including schizophrenia and related disorders, bipolar disease and obsessive-compulsive disorder, eating disorders, sleep-related disorders, affective disorders including depression, anxiety, panic states and stress-related disorders, aggression, emesis, pain and hyperalgesic states of inflammatory and neuropathic origins, sleep and sexual disorders and alcohol and drug abuse or states associated with drug withdrawal including smoking cessation.

WO97/19059 discloses substituted aryl compounds capable of modulating acetylcholine receptors. WO99/32117 discloses similar compounds wherein the aryl moiety is replaced by a 2- or 4-pyridine moiety. Specifically, it discloses the compound

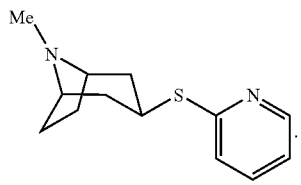

Other compounds specifically disclosed all possess a linker, usually methylene or ethylene, between the S atom and either (or both) of the two ring systems shown above. It would be desirable to provide alternative compounds to those disclosed in WO97/19059 and WO99/32117. Preferably, such alternatives should exhibit one or more of the following advantages: improved binding to nAChRs, greater modulation of nAChRs, improved selectivity between different nAChRs and improved pharmacokinetic properties (e.g. improved bioavailability).

Radl et al (Archiv der Pharmazie, Weinheim, Germany, 2000, 333(5), 107–112) discloses the synthesis and analgesic activity of some side-chain modified anpirtoline derivatives including 3-(3-chlorophenylthio)-8-methyl-8-azabicyclo[3.2.1]octane and 2-chloro-6-(3-(8-methyl-8-azabicyclo[3.2.1]octyl)thio)-pyridine.

EP0398578 discloses 3-phenylthio-8-azabicyclo[3.2.1]octane and 3-phenylthio-8-methyl-8-azabicyclo[3.2.1]octane as intermediates in the synthesis of piperidino and 8-azabicyclo[3.2.1]oct-8-yl alkanols which are usefull for the treatment of CNS disorders.

The present invention provides compounds represented by Formula (I) or pharmaceutically acceptable salts thereof:

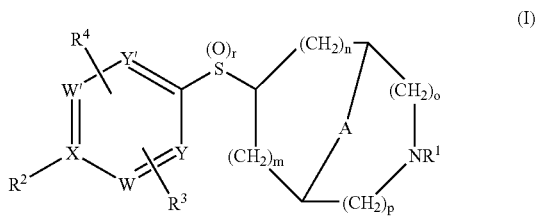

(I)

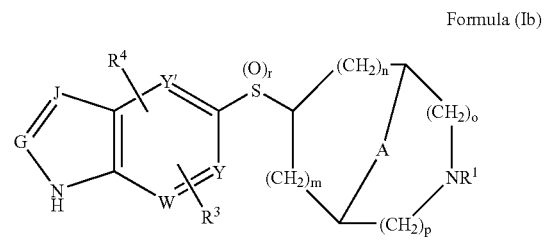

Formula (Ib)

wherein:
R¹ is —H,
C$_{1-12}$alkyl optionally substituted with 1, 2 or 3 groups independently selected from halogen, hydroxyl, thiol, C$_{1-4}$alkoxy or C$_{1-4}$alkylthio, or aryl-C$_{1-4}$alkyl;
R² is —H,
—OH,
—NH$_2$,
—NH-Q-V-T, wherein
Q is —C(O)—, —C(O)—NH—, —C(O)O—, or —SO$_2$—;
V is H, aryl, aryl-C$_{1-12}$alkyl, diaryl-C$_{1-12}$alkyl, lactonyl, or C$_{1-18}$alkyl optionally substituted with halogen, hydroxyl, C$_{1-4}$alkoxy, —C(O)OC$_{1-4}$alkyl, —OC(O)C$_{1-4}$alkyl, aryl-C$_{1-4}$alkoxy, aryloxy, or SO$_2$C$_{1-4}$alkyl; and
T is H, halogen, C$_{1-5}$alkyl, C$_{1-4}$alkoxy, nitro, aryl, aryl-C$_{1-4}$alkyl, or aryloxy unless V is H in which case T is absent,
aryl,
-(L)$_a$-Z, wherein
L is CH$_2$, CO, O, NH or N(C$_{1-4}$alkyl) and a is 0 or 1; and
Z is C$_{1-3}$alkyl-F, C$_{0-3}$alkyl-aryl-R⁶, C$_{0-3}$alkyl-CO—R⁶, C$_{0-3}$alky-CO—NR⁶$_2$, C$_{0-3}$alkyl-CO$_2$—R⁶, C$_{0-3}$alkyl-SO$_2$—R⁶, CO$_{0-3}$alkyl-SO$_2$—NR⁶$_2$, C$_{1-3}$alkyl-OR⁶, C$_{1-3}$alkyl-CN or C$_{1-3}$alkyl-NR⁶$_2$, wherein each C$_{0-3}$alkyl or C$_{1-3}$alkyl portion is optionally substituted with from 1 to 6 groups selected from F and C$_{1-5}$alkyl, linked back to the aromatic ring so as to form a fused bicyclic compound represented by Formula (Ia)

(Ia)

wherein
D is O or S; and
E is O, S, NR⁵, C(R⁵)$_2$, O—CR⁵$_2$, NR⁵—CR⁵$_2$, NR⁵—CO, CR⁵$_2$—O, CR⁵$_2$—S(O)$_r$, CR⁵$_2$—NR⁵, CR⁵$_2$—CR⁵$_2$, CO—NR⁵, or CR⁵=CR⁵; or linked back to the aromatic ring so as to form a fused bicyclic compound represented by Formula (Ib)

wherein
G is CR⁵ or N; and
J is CR⁵ or N;
unless X is N in which case R² is absent
R³ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R⁴ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R⁵ is each independently H or C$_{1-4}$alkyl;
R⁶ is each independently H, C$_{1-6}$alkyl, aryl or arylC$_{1-4}$alkyl, each of which (except H) maybe optionally substituted with from 1 to 3 fluorine atoms;
X is C or N;
W is C or N;
W' is C or N;
Y is C or N;
Y' is C or N;
provided that there are no more than two N atoms in the aryl ring;
A is optionally a double bond, (CH$_2$)$_q$ or (CH$_2$)O(CH$_2$);
m, n, o and p are independently 0, 1, 2 or 3;
q is optionally 1, 2 or 3;
r is 0, 1 or 2.

provided that
when X, W, W', Y and Y' are all C, R³ is H, R⁴ is H or Cl positioned meta to the sulphur atom, A is (CH$_2$)$_q$ and R¹ is selected from H, unsubstituted C$_{1-4}$alkyl and unsubstituted C$_{3-4}$cycloalkyl; then R² may not be H or —OH, and that
when one of X, Y and Y' is N, R³ is H, R⁴ is H or Cl positioned meta to the sulphur atom, A is (CH$_2$)$_q$ and R¹ is selected from H, unsubstituted C$_{1-4}$alkyl and unsubstituted C$_{3-4}$cycloalkyl; then R² may not be H or —OH.

In a further embodiment of the present invention: R² is —H,
—NH$_2$,
—NH-Q-V-T as defined in claim 1,
aryl,
-(L)$_a$-Z as defined in claim 1,
linked back to the aromatic ring so as to form a fused bicyclic compound represented by Formula (Ia) as defined in claim 1, or linked back to the aromatic ring so as to form a fused bicyclic compound represented by Formula (Ib) as defined in claim 1;

unless X is N in which case R² is absent.
In a further embodiment of the present invention:

$R^2$ is —NH-Q-V-T as defined in claim 1, aryl, -(L)$_a$-Z as defined in claim 1, linked back to the aromatic ring so as to form a fused bicyclic compound represented by Formula (Ia) as defined in claim 1, or linked back to the aromatic ring so as to form a fused bicyclic compound represented by Formula (Ib) as defined in claim 1; unless X is N in which case $R^2$ is absent.

In a further embodiment of the present invention:
$R^2$ is —NH-Q-V-T wherein
Q is —C(O)—NH—, or —C(O)O—;
V is as defined in claim 1; and
T is as defined in claim 1;
aryl,
-(L)$_a$-Z as defined in claim 1,
linked back to the aromatic ring so as to form a fused bicyclic compound represented by Formula (Ia) as defined in claim 1, or linked back to the aromatic ring so as to form a fused bicyclic compound represented by Formula (Ib) as defined in claim 1;
unless X is N in which case $R^2$ is absent.

In one embodiment, the present invention provides a sub-group of compounds (Group A) represented by formula (II) or pharmaceutically acceptable salts thereof:

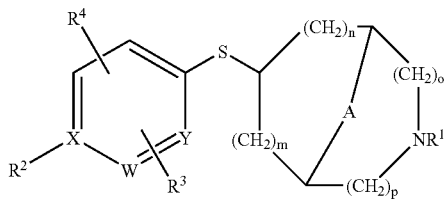

(II)

wherein:
$R^1$ is —H; or
  $C_{1-12}$alkyl optionally substituted with 1, 2 or 3 groups independently selected from halogen, hydroxyl, thiol, $C_{1-4}$alkoxy or $C_{1-4}$alkylthio; or
  aryl-$C_{1-4}$alkyl
$R^2$ is —H;
  —OH;
  —NH$_2$;
  —NH-Q-V-T
Q is —C(O)—;
  —C(O)—NH—;
  —C(O)O—; or
  —SO$_2$—
V is aryl;
  aryl-$C_{1-12}$alkyl;
  diaryl-$C_{1-12}$alkyl;
  lactonyl; or
  $C_{1-18}$alkyl optionally substituted with halogen, hydroxyl, $C_{1-4}$alkoxy, —C(O)OC$_{1-4}$alkyl, —OC(O)C$_{1-4}$alkyl, aryl-$C_{1-4}$alkoxy, aryloxy, SO$_2$C$_{1-4}$alkyl;
T is H;
  halogen;
  aryl;
  aryl-$C_{1-4}$alkyl; or
  aryloxy; unless X is N in which case $R^2$ is absent
$R^3$ and $R^4$ are each independently selected from H, halogen, $C_{1-4}$alkyl, cyano, CF$_3$, OC$_{1-4}$alkyl, aryloxy, arylC$_{1-4}$alkoxy, $C_{3-10}$cycloalkoxy, carboxy, carbonamido, —CO—NH—$C_{1-4}$alkyl, aryl, hydroxy, —SO$_2$NH$_2$, —SO$_2$NHC$_{1-4}$alkyl, —$C_{1-4}$alkyl—OH;

X is C or N;
W is C or N, provided that both X and Y are not N;
Y is C or N
A is optionally a double bond, (CH$_2$)$_q$ or (CH$_2$)O(CH$_2$)
m, n, o and p are independently 0, 1, 2 or 3
q is optionally 1, 2 or 3.

Within Group A, A is preferably a double bond or (CH$_2$)$_q$ and $R^1$ is preferably —H; or $C_{1-12}$alkyl optionally substituted with 1, 2 or 3 groups independently selected from hydroxyl, thiol, $C_{1-4}$alkoxy or $C_{1-4}$alkylthio; or aryl-$C_{1-4}$alkyl.

Within Group A, $R^1$ is more preferably H; $C_{1-6}$alkyl optionally substituted with 1 or 2 hydroxyl groups; or aryl-$C_{1-4}$alkyl. When $R^1$ is an aryl-$C_{1-4}$alkyl group, examples of suitable groups are benzyl, p-methoxybenzyl, furanylmethyl, imidazolylmethyl, pyridinylmethyl, thienylmethyl, pyridylmethyl, N-hydroxypyridylmethyl or thiazolylmethyl.

Within Group A, $R^1$ is more preferably H, methyl, cyclopropylmethyl, 2-hydroxyethyl or isobutyl. When $R^1$ is one of these groups, greater potency is generally observed. More preferably, $R^1$ is a methyl group.

In one embodiment of Group A, $R^2$ is H. When $R^2$ is H, $R^3$ is preferably carbonamido (—CONH$_2$) or —$C_{1-4}$alkyl-OH and $R^4$ is H, $C_{1-4}$alkyl, CF$_3$, halogen or cyano (more preferably H, halogen or cyano). More preferably $R^3$ is carbonamido (—CONH$_2$) or —$C_{1-4}$alkyl-OH and $R^4$ is methyl, CF$_3$, Cl or cyano (more preferably Cl or cyano).

In another embodiment of Group A, $R^2$ is OH. When $R^2$ is OH, $R^3$ and $R^4$ are preferably H, $C_{1-4}$alkyl, CF$_3$, cyano or halogen (more preferably H, cyano or halogen). More preferably $R^3$ is methyl, CF$_3$, Cl or cyano (more preferably Cl or cyano) attached to position Y when Y is C.

Generally, within Group A, when $R^2$ is of formula —NH-Q-V-T, T is preferably H and $R^3$ and $R^4$ are preferably H, methyl, CF$_3$, chloro- or cyano (more preferably H, chloro- or cyano).

In another embodiment of Group A, $R^2$ is of the formula —NH—SO$_2$-V-T, wherein V is aryl, —$C_{1-12}$alkyl or aryl-$C_{1-12}$alkyl. In this embodiment of the present invention $R^3$ is preferably H, methyl, CF$_3$, Cl or cyano (more preferably H, Cl or cyano) and $R^4$ is preferably H.

Within Group A, when $R^2$ is of formula —NH—SO$_2$-V-T, preferably V is selected from $C_{1-12}$alkyl, phenyl, naphthyl, thienyl, oxazolyl, isoxazolyl, or phenyl(CH═CH)—, optionally substituted with 1, 2, 3 or 4 substituents selected from:
—NO$_2$;
halogen;
—CF$_3$;
$C_{1-12}$alkoxy;
$C_{1-12}$allkylthio;
$C_{1-12}$alkyl;
$C_{1-4}$alkylsulfonyl;
—CN;
—OCF$_3$;
—C(O)OC$_{1-4}$alkyl;
—OCH$_2$CF$_3$;
—NHC(O)C$_{1-4}$alkyl.

Within Group A, when $R^2$ is of formula —NH—SO$_2$-V-T, preferably T is selected from H, or diazole, oxazole, isoxazole, phenyl or phenoxy, optionally substituted with 1, 2, 3 or 4 substituents selected from
—NO$_2$;
halogen;
—CF$_3$;
$C_{1-12}$alkoxy;

$C_{1-12}$alkylthio;
$C_{1-12}$alkyl;
$C_{1-4}$alkylsulfonyl;
—CN;
—OCF$_3$;
—C(O)OC$_{1-4}$alkyl;
—OCH$_2$CF$_3$;
—NHC(O)C$_{1-4}$alkyl.

Within Group A, when $R^2$ is of formula —NH—SO$_2$-V-T, V is more preferably selected from 3-chloro-4-methylphenyl, 3-chlorophenyl, 3-methoxyphenyl, 4-bromophenyl, 4-methoxyphenyl, 4-methylphenyl, naphthyl, 2,4,6-trimethylphenyl, phenyl(CH═CH)—, 4-chlorophenyl, 2-chlorophenyl, 2,5-dichlorothien-3-yl, 2,5,6-trimethyl-4-methoxyphenyl, 4-methoxyphenyl, 2,3,4-trifluorophenyl, 3-cyanophenyl, 2-methoxycarbonylthien-3-yl or 4-pentylphenyl (even more preferably selected from 4-bromophenyl, 4-methoxyphenyl, 4-methylphenyl, naphthyl, 2,4,6-trimethylphenyl, phenyl(CH═CH)—, 4-chlorophenyl, 2-chlorophenyl, 2,5-dichlorothien-3-yl, 2,5,6-trimethyl-4-methoxyphenyl, 4-methoxyphenyl, 2,3,4-trifluorophenyl, 3-cyanophenyl, 2-methoxycarbonylthien-3-yl or 4-pentylphenyl) and T is preferably H.

In a further embodiment within Group A, when $R^2$ is of formula —NH—SO$_2$-V-T, T is preferably 2-chloro-5-nitrophenoxy and V is preferably phenyl.

In an alternative embodiment of Group A, $R^2$ is of formula —NH—C(O)-V-T wherein V is selected from
aryl;
aryl-$C_{1-12}$alkyl;
diaryl-$C_{1-12}$alkyl;
lactonyl; or
$C_{1-18}$alkyl optionally substituted with halogen, hydroxyl, $C_{1-4}$alkoxy, C(O)OC$_{1-4}$alkyl, OC(O)C$_{1-4}$alkyl, aryl-$C_{1-4}$alkoxy, aryloxy. In this embodiment of the present invention, $R^3$ is preferably H, methyl, CF$_3$, Cl or cyano (more preferably H, Cl or cyano) and $R^4$ is H.

When $R^2$ is of formula —NH—C(O)-V-T, preferably V is selected from $C_{1-12}$alkyl, phenyl, phenyl-$C_{1-12}$alkyl, diphenylmethyl, naphthyl, furanyl, thienyl, diazolyl, pyridinyl, thiazolyl, benzothienyl, fluorenyl, oxazolyl or isoxazolyl, optionally substituted with 1, 2, 3 or 4 substituents independently selected from
—NO$_2$;
halogen;
—CF$_3$;
$C_{1-12}$alkoxy;
$C_{1-12}$alkylthio;
$C_{1-12}$alkyl;
$C_{1-4}$alkylsulfonyl;
—CN;
—OCF$_3$;
—C(O)O—$C_{1-4}$alkyl;
—OCH$_2$CF$_3$.

When $R^2$ is of formula —NH—C(O)-V-T, more preferably V is $C_{1-12}$alkyl.

When $R^2$ is of formula —NH—C(O)-V-T, preferably T is selected from
H;
halogen; or
diazole, oxazole, isoxazole, phenyl, phenoxy or benzodioxanyl optionally substituted with 1, 2, 3 or 4 substituents selected from
—NO$_2$;
halogen;
—CF$_3$;
$C_{1-12}$alkylthio;
$C_{1-12}$alkoxy;
$C_{1-12}$alkyl;
$C_{1-4}$alkylsulfonyl;
—CN;
—OCF$_3$;
—C(O)O—CIA alkyl.

When $R^2$ is of formula —NH—C(O)-V-T, more preferably T is H.

In an alternative embodiment of Group A, $R^2$ is of formula —NH—C(O)NH-V-T wherein V is selected from
$C_{1-18}$alkyl optionally substituted with halogen, hydroxyl, $C_{1-4}$alkoxy, C(O)OC$_{1-4}$alkyl, OC(O)C$_{1-4}$alkyl, aryl-$C_{1-4}$ alkoxy or aryloxy;
aryl; or
aryl-$C_{1-12}$alkyl.

When $R^2$ is of formula —NH—C(O)NH-V-T, preferably V is selected from phenyl, phenyl-$C_{1-12}$alkyl or naphthyl optionally substituted with 1, 2, 3 or 4 substituents selected from
—NO$_2$;
halogen;
—CF$_3$;
$C_{1-12}$alkylthio;
$C_{1-12}$alkoxy;
$C_{1-12}$alkyl;
$C_{1-4}$alkylsulfonyl;
—CN;
—OCF$_3$;
—C(O)O—$C_{1-4}$alkyl.

When $R^2$ is of formula —NH—C(O)NH-V-T, preferably T is H.

In an alternative embodiment of Group A, $R^2$ is of formula —NH—C(O)O-V-T, wherein V is selected from
$C_{1-18}$alkyl optionally substituted with halogen, hydroxyl, $C_{1-4}$alkoxy, C(O)OC$_{1-4}$alkyl, OC(O)C$_{1-4}$alkyl, aryl-$C_{1-4}$ alkoxy or aryloxy;
aryl; or
aryl-$C_{1-12}$ alkyl.

When $R^2$ is of formula —NH—C(O)O-V-T, preferably V is selected from phenyl or phenyl-$C_{1-12}$alkyl optionally substituted with 1, 2, 3 or 4 substituents selected from
—NO$_2$;
halogen;
—CF$_3$;
$C_{1-12}$alkylthio;
$C_{1-12}$alkoxy;
$C_{1-12}$alkyl;
$C_{1-4}$alkylsulfonyl;
—CN;
—OCF$_3$;
—C(O)O—$C_{1-4}$alkyl; or
—OCH$_2$CF$_3$.

When $R^2$ is of formula —NH—C(O)O-V-T, preferably T is H.

In another embodiment, the present invention provides a further sub-group of compounds (Group B) represented by formula (I) or pharmaceutically acceptable salts thereof:
wherein $R^2$ is of formula —NH—C(O)-V-T
wherein V is H, $C_{1-6}$alkyl, $C_{3-6}$cycloalkyl, aryl or aryl-$C_{1-12}$alkyl; and
T is H, halogen, $C_{1-5}$alkyl, $C_{1-4}$alkoxy, nitro, aryl, aryl-$C_{1-4}$alkyl, or aryloxy unless V is H in which case T is absent.

In a preferred embodiment within Group B, when V is H, $C_{1-6}$alkyl or $C_{3-6}$cycloalkyl, preferably T is H unless V is H in which case T is absent.

In another preferred embodiment within Group B, when V is aryl or aryl-$C_{1-12}$alkyl, preferably T is H, halogen, $C_{1-5}$alkyl, $C_{1-4}$alkoxy, nitro, aryl, aryl-$C_{1-4}$alkyl, or aryloxy.

More preferably, V is phenyl, pyridyl, thienyl, thiazolyl, thiadiazolyl, or phenyl-$C_{1-6}$alkyl; and T is H, halogen, $C_{1-5}$alkyl, $C_{1-4}$alkoxy, nitro, aryl, aryl-$C_{1-4}$alkyl, or aryloxy.

In another embodiment, the present invention provides a further sub-group of compounds (Group C) represented by formula (I) or pharmaceutically acceptable salts thereof:

wherein $R^1$ is —H,
  $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;

$R^2$ is —$NH_2$, or
  —NH-Q-V-T, wherein
    Q is —C(O)—, —C(O)—NH—, —C(O)O—, or —$SO_2$—;
    V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or $SO_2C_{1-4}$alkyl; and
    T is H, halogen, aryl, aryl-$C_{1-4}$alkyl, or aryloxy unless V is H in which case T is absent, $R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

X is C;
W is C or N;
W' is C or N;
Y is C or N;
Y' is C or N;
provided that there are not more than two N atoms in the aryl ring and provided that at least one of W, W', Y or Y' is N;
A is optionally a CH=CH double bond, $(CH_2)_q$ or $(CH_2)O(CH_2)$;
m, n, o and p are independently 0, 1, 2 or 3;
q is optionally 1, 2 or 3;
r is 0, 1 or 2.

In a preferred embodiment of the compounds of Group C only one of W, W', Y and Y' is N.

In one embodiment of the compounds of Group C
W is C;
W' is C;
Y' is C; and
Y is N.

In another embodiment of the compounds of Group C
W is N;
W' is C;
Y' is C; and
Y is C.

In another embodiment of the compounds of Group C, $R^2$ is —$NH_2$.

In another embodiment of the compounds of Group C $R^2$ is —NH-Q-V-T, wherein

Q is —C(O)—, —C(O)—NH—, —C(O)O—, or —$SO_2$—;
V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or $SO_2C_{1-4}$alkyl; and
T is H, halogen, aryl, aryl-$C_{1-4}$alkyl, or aryloxy unless V is H in which case T is absent.

Within Group C, when $R^2$ is —NH-Q-V-T, preferably Q is —$SO_2$— or —CO—.

In another embodiment, the present invention provides a further sub-group of compounds (Group D) represented by formula (I) or pharmaceutically acceptable salts thereof:
wherein $R^1$ is —H,
  $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;

$R^2$ is aryl, $R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH, $R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

X is C,
W is C or N;
W' is C or N;
Y is C or N;
Y' is C or N;
provided that there are no more than two N atoms in the aryl ring;
A is optionally a CH=CH double bond, $(CH_2)_q$ or $(CH_2)O(CH_2)$;
m, n, o and p are independently 0, 1, 2 or 3;
q is optionally 1, 2 or 3;
r is 0, 1 or 2.

Within Group D, $R^2$ is preferably a $C_3$ to $C_{12}$ aromatic or heteroaromatic group optionally substituted with one or more substituents selected from $C_{1-12}$alkyl, $C_{1-12}$alkoxy, thio, $C_{1-12}$alkylthio, carboxy, carboxy($C_{1-6}$alkyl), formyl, $C_{1-6}$alkylcarbonyl, $C_{1-6}$alkylsulfonyl, $C_{1-6}$alkylcarbonylalkoxy, nitro, trihalomethyl, trihaloalkoxy, trihalomethoxy, trihalomethyl($C_{1-6}$alkyl), hydroxy, hydroxy($C_{1-6}$)alkyl, ($C_{1-6}$ alkoxy)carbonyl, amino, $C_{1-6}$alkylamino, di($C_{1-6}$alkyl)amino, aminocarboxy, $C_{1-6}$alkylaminocarboxy, di($C_{1-6}$alkyl) aminocarboxy, aminocarboxy($C_{1-6}$)alkyl, $C_{1-6}$alkylaminocarboxy($C_{1-6}$alkyl), di($C_{1-6}$alkyl)aminocarboxy($C_{1-6}$alkyl), $C_{1-6}$alkylcarbonylamino, $C_{1-6}$alkylcarbonyl($C_{1-6}$alkyl)amino, halo, $C_{1-6}$alkylhalo, sulphamoyl, tetrazolyl and cyano.

Within Group D, $R^2$ is more preferably phenyl, naphthyl, fluorenyl, thienyl, furanyl, pyrrolyl, imidazolyl, pyrazolyl, thiazolyl, isothiazolyl, oxazolyl, isoxazolyl, oxadiazolyl, thiadiazolyl, diazolyl, triazolyl, tetrazolyl, benzothiazolyl, benzimidazolyl, pyrrolinyl, imidazolinyl, pyranyl, pyronyl, pyridyl, pyrazinyl, pyridazinyl, thianaphthyl, benzofuranyl, isobenzofuranyl, benzothienyl, isobenzothienyl, indolyl, oxyindolyl, isoindolyl, indazolyl, indolinyl, 7-azaindolyl, azabenzimidazolyl, carbazolyl benzopyranyl, coumarinyl, isocoumarinyl, quinolinyl, isoquinolinyl, quinazolinyl, benzoxazinyl, quinoxalinyl, chromenyl, chromanyl, isochromanyl, phthalazinyl, benzodioxolyl, benzodioxanyl, cinnolinyl or carbolinyl optionally substituted with one or more substituents selected from $C_{1-12}$alkyl, $C_{1-12}$alkoxy, thio, $C_{1-12}$alkylthio, carboxy, carboxy($C_{1-6}$alkyl), formyl, $C_{1-6}$alkylcarbonyl, $C_{1-6}$alkylsulfonyl, $C_{1-6}$alkylcarbonylalkoxy, nitro, trihalomethyl, trihaloalkoxy, trihalomethoxy, trihalomethyl($C_{1-6}$alkyl), hydroxy, hydroxy($C_{1-6}$)alkyl, ($C_{1-6}$ alkoxy)carbonyl, amino, $C_{1-6}$alkylamino, di($C_{1-6}$alkyl) amino, aminocarboxy, $C_{1-6}$alkylaminocarboxy, di($C_{1-6}$ alkyl) aminocarboxy, aminocarboxy($C_{1-6}$)alkyl, $C_{1-6}$alkylaminocarboxy($C_{1-6}$alkyl), di($C_{1-6}$alkyl)aminocarboxy($C_{1-6}$ alkyl), $C_{1-6}$alkylcarbonylamino, $C_{1-6}$alkylcarbonyl($C_{1-6}$ alkyl)amino, halo, $C_{1-6}$alkylhalo, sulphamoyl, tetrazolyl and cyano.

Within Group D, $R^2$ is even more preferably phenyl, thienyl, imidazolyl, oxazolyl, isoxazolyl, oxadiazolyl, thiadiazolyl, diazolyl, triazolyl, tetrazolyl, benzothiazolyl, benzimidazolyl, pyridyl, pyrazinyl, pyridazinyl, benzofuranyl, benzothienyl, or quinolinyl optionally substituted with one or more substituents selected from $C_{1-12}$alkyl, $C_{1-12}$alkoxy, thio, $C_{1-12}$alkylthio, carboxy, carboxy($C_{1-6}$alkyl), formyl, $C_{1-6}$alkylcarbonyl, $C_{1-6}$alkylsulfonyl, $C_{1-6}$alkylcarbonylalkoxy, nitro, trihalomethyl, trihaloalkoxy, trihalomethoxy, trihalomethyl($C_{1-6}$alkyl), hydroxy, hydroxy($C_{1-6}$)alkyl, ($C_{1-6}$ alkoxy)carbonyl, amino, $C_{1-6}$alkylamino, di($C_{1-6}$alkyl) amino, aminocarboxy, $C_{1-6}$alkylaminocarboxy, di($C_{1-6}$ alkyl) aminocarboxy, aminocarboxy($C_{1-6}$)alkyl, $C_{1-6}$alkylaminocarboxy($C_{1-6}$alkyl), di($C_{1-6}$alkyl)aminocarboxy($C_{1-6}$ alkyl), $C_{1-6}$alkylcarbonylamino, $C_{1-6}$alkylcarbonyl($C_{1-6}$ alkyl)amino, halo, $C_{1-6}$alkylhalo, sulphamoyl, tetrazolyl and cyano.

Within Group D, $R^2$ is even more preferably phenyl, pyridyl, or benzofuranyl, optionally substituted with one or more substituents selected from $C_{1-12}$alkyl, $C_{1-12}$alkoxy, thio, $C_{1-12}$alkylthio, carboxy, carboxy($C_{1-6}$alkyl), formyl, $C_{1-6}$alkylcarbonyl, $C_{1-6}$alkylsulfonyl, $C_{1-6}$alkylcarbonylalkoxy, nitro, trihalomethyl, trihaloalkoxy, trihalomethoxy, trihalomethyl($C_{1-6}$alkyl), hydroxy, hydroxy($C_{1-6}$)alkyl, ($C_{1-6}$ alkoxy)carbonyl, amino, $C_{1-6}$alkylamino, di($C_{1-6}$alkyl) amino, aminocarboxy, $C_{1-6}$alkylaininocarboxy, di($C_{1-6}$ alkyl) aminocarboxy, aminocarboxy($C_{1-6}$)alkyl, $C_{1-6}$alkylaminocarboxy($C_{1-6}$alkyl), di($C_{1-6}$alkyl)aminocarboxy($C_{1-6}$ alkyl), $C_{1-6}$alkylcarbonylamino, $C_{1-6}$alkylcarbonyl($C_{1-6}$ alkyl)amino, halo, $C_{1-6}$alkylhalo, sulphamoyl, tetrazolyl and cyano.

In another embodiment, the present invention provides a further sub-group of compounds (Group E) represented by formula (I) or pharmaceutically acceptable salts thereof: wherein:
$R^1$ is —H,
  $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
$R^2$ is
  $(L)_a$-Z, wherein
    L is O; CO, $CH_2$, NH or N($C_{1-4}$alkyl) and a is 0 or 1; and
    Z is $C_{1-3}$alkyl-F, $C_{0-3}$alkyl-aryl-$R^6$, $C_{0-3}$alkyl-CO—$R^6$, $C_{0-3}$alkyl-CO—$NR^6_2$, $C_{0-3}$alkyl-$CO_2$—$R^6$, $C_{0-3}$alkyl-$SO_2$—$R^6$, $C_{0-3}$alkyl-$SO_2$—$NR^6_2$, $C_{1-3}$alkyl-$OR^6$, $C_{1-3}$alkyl-CN or $C_{1-3}$alkyl-$NR^6_2$ wherein each $C_{0-3}$alkyl or $C_{1-3}$alkyl portion is optionally substituted with from 1 to 6 groups selected from F and $C_{1-5}$alkyl, $R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$ alkyl, aryl, hydroxy, —$SO_2NH_2$, —$SO_2NHC_{1-4}$alkyl, or —$C_{1-4}$alkyl-OH;
$R^4$ is H, halogen, $C_{1-4}$alkyl optionally substituted with from 1 to 3 fluorine atoms, cyano, $CF_3$, $OC_{1-4}$allyl, aryloxy, aryl$C_{1-4}$alkyl, aryl$C_{1-4}$alkoxy, $C_{3-10}$cycloalkoxy, carboxy, carbonamido, —CO—NH—$C_{1-4}$ alkyl, aryl, hydroxy, —$SO_2NH_2$, —$SO_2NHC_{1-4}$alkyl, or —$C_{1-4}$alkyl-OH;
$R^6$ is each independently H, $C_{1-6}$alkyl, aryl, or aryl$C_{1-4}$alkyl, each of which (except H) may be optionally substituted with from 1 to 3 fluorine atoms;
X is C;
W is C or N,
Y is C or N,
W' is C or N,
Y' is C or N,
provided that there are no more than two N atoms in the aryl ring,
A is optionally a double bond, $(CH_2)_q$ or $(CH_2)O(CH_2)$;
m, n, o and p are independently 0, 1, 2 or 3;
q is optionally 1, 2 or 3;
r is 0, 1 or 2.

In one preferred embodiment of sub-group E, L is CO.
In another preferred embodiment of sub-group E, L is $CH_2$.
In another preferred embodiment of sub-group E, L is O.
In another preferred embodiment of sub-group E, L is NH or N($C_{1-4}$alkyl).
In another preferred embodiment of sub-group E, Z is $C_{0-3}$alkyl-aryl-$R^6$, $C_{0-3}$alkyl-CO—$NR^6_2$, $C_{0-3}$alkyl-$CO_2$—$R^6$, $C_{1-3}$alkyl-$OR^6$ or $C_{1-3}$alkyl-$NR^6_2$ wherein each $C_{0-3}$alkyl or $C_{1-5}$alkyl portion is optionally substituted with from 1 to 6 groups selected from F and $C_{1-5}$alkyl.

In another preferred embodiment of sub-group E, Z is $C^{0-3}$alkyl-aryl-$R^6$ wherein aryl is selected from phenyl, naphthyl, fluorenyl, thienyl, furanyl, pyrrolyl, imidazolyl, pyrazolyl, thiazolyl, isothiazolyl, oxazolyl, isoxazolyl, oxadiazolyl, thiadiazolyl, diazolyl, triazolyl, tetrazolyl, benzothiazolyl, benzimidazolyl, pyrrolinyl, imidazolinyl, pyranyl, pyronyl, pyridyl, pyrazinyl, pyridazinyl, thianaphthyl, benzofuranyl, isobenzofuranyl, benzothienyl, isobenzothienyl, indolyl, oxyindolyl, isoindolyl, indazolyl, indolinyl, 7-azaindolyl, azabenzimidazolyl, carbazolyl benzopyranyl, coumarinyl, isocoumarinyl, quinolinyl, isoquinolinyl, quinazolinyl, benzoxazinyl, quinoxalinyl, chromenyl, chromanyl, isochromanyl, phthalazinyl, benzodioxolyl, benzodioxanyl, cinnolinyl or carbolinyl optionally, be substituted with one or more substituents selected from $C_1$ to $C_{12}$ alkyl (preferably $C_1$ to $C_6$ alkyl), $C_1$ to $C_{12}$ alkoxy (preferably $C_1$ to $C_6$ alkoxy), thio, $C_1$ to $C_{12}$ alkylthio (preferably $C_1$ to $C_6$ alkylthio), carboxy, carboxy($C_1$ to $C_6$)alkyl, formyl, $C_1$ to $C_6$ alkylcarbonyl, $C_1$ to $C_6$ alkylsulfonyl, $C_1$ to $C_6$ alkylcarbonylalkoxy, nitro, trihalomethyl, trihalo($C_1$ to $C_6$ alkoxy), trihalomethoxy, trihalomethyl($C_1$ to $C_6$ alkyl), hydroxy, hydroxy($C_1$ to $C_6$)alkyl, ($C_1$ to $C_6$ alkoxy)carbonyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy($C_1$ to $C_6$)alkyl, di($C_1$ to $C_6$ alkyl)aminocarboxy($C_1$ to $C_6$)alkyl, $C_1$ to $C_6$ alkylcarbonylamino, $C_1$ to $C_6$ alkylcarbonyl($C_1$ to $C_6$ alkyl)amino, halo, $C_1$ to $C_6$ alkylhalo, sulphamoyl, tetrazolyl and cyano and wherein each $C_{0-3}$alkyl portion is optionally substituted with from 1 to 3 groups selected from F and $C_{1-3}$alkyl.

In another preferred embodiment of sub-group E, Z is $C_{1-3}$alkyl-CO—$NR^6{}_2$, wherein each $C_{1-3}$alkyl portion is optionally substituted with from 1 to 3 groups selected from F and $C_{1-3}$alkyl.

In another preferred embodiment of sub-group E, Z is $C_{1-3}$alkyl-$CO_2$—$R^6$, wherein each $C_{1-3}$alkyl portion is optionally substituted with from 1 to 3 groups selected from F and $C_{1-3}$alkyl.

In another preferred embodiment of sub-group E, Z is $C_{1-3}$alkyl-$OR^6$ wherein each $C_{1-3}$alkyl portion is optionally substituted with from 1 to 3 groups selected from F and $C_{1-3}$alkyl.

In another preferred embodiment of sub-group E, Z is $C_{1-3}$alkyl-$NR^6{}_2$ wherein each $C_{1-3}$alkyl portion is optionally substituted with from 1 to 3 groups selected from F and $C_{1-3}$alkyl.

Preferably, within Group E, $R^6$ is/are each independently H, C, alkyl, phenyl, or phenyl$C_{1-4}$alkyl, each of which (except H) may be optionally substituted with from 1 to 3 fluorine atoms. More preferably, within Group E, $R^6$ is/are each independently H, methyl, ethyl, propyl, cyclohexyl, or benzyl, each of which (except H) may be optionally substituted with 1, 2 or 3 fluorine atoms.

In another embodiment, the present invention provides a further sub-group of compounds (Group $F^1$) represented by formula (I) or pharmaceutically acceptable salts thereof:
wherein:
$R^1$ is —H,
  $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
$R^2$ is linked back to the aromatic ring so as to form a fused bicyclic compound represented by Formula (Ia)

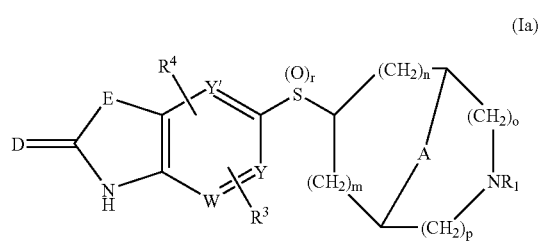

wherein
  D is O or S; and
  E is O, S, $NR^5$, or $C(R^5)_2$,
$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;
$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;
$R^5$ is each independently H, $C_{1-4}$alkyl;
X is C;
W is C or N;
Y is C or N;
Y' is C or N;
provided that there are no more than two N atoms in the aryl ring,
A is optionally a double bond, $(CH_2)_q$ or $(CH_2)O(CH_2)$;
m, n, o and p are independently 0, 1, 2 or 3;
q is optionally 1, 2 or 3;
r is 0, 1 or 2.

In one preferred embodiment of sub-group $F^1$, E is O or $NR^5$.

In another preferred embodiment of sub-group $F^1$, $R^5$ is/are each independently H or $C_{1-4}$alkyl.

In another embodiment, the present invention provides a further sub-group of compounds (Group $F^2$) represented by formula (I) or pharmaceutically acceptable salts thereof:
wherein:
$R^1$ is —H,
  $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
$R^2$ is linked back to the aromatic ring so as to form a fused bicyclic compound represented by Formula (Ia)

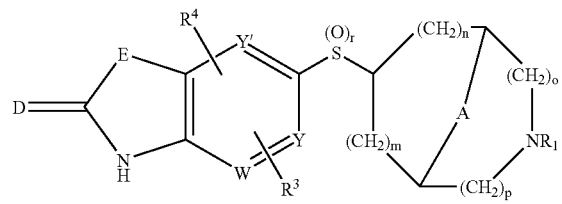

wherein D is O or S; and
  E is O—$CR^5{}_2$, $NR^5$—$CR^5{}_2$, $NR^5$—CO, $CR^5{}_2$—O, $CR^5{}_2$—$S(O)_r$, $CR^5{}_2$—$NR^5$, $CR^5{}_2$—$CR^5{}_2$, CO—$NR^5$, or $CR^5$=$CR^5$;
$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alky, or —$C_{1-4}$alkyl-OH;
$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-14}$alkyl, aryl, hydroxy, —$SO_2NH_2$, —$SO_2NHC_{1-4}$alkyl, or —$C_{1-4}$alkyl-OH;
$R^5$ is each independently H, $C_{1-4}$alkyl;
X is C;
W is C or N;
Y is C or N;
Y' is C or N;
provided that there are no more than two N atoms in the aryl ring;
A is optionally a double bond or $(CH_2)_q$ or $(CH_2)O(CH_2)$;
m,n,o and p are independently 0, 1, 2 or 3;
q is optionally 1, 2 or 3;
r is 0, 1 or 2.

In one preferred embodiment of sub-group $F^2$, E is O—$CR^5{}_2$, $NR^5$—$CR^5{}_2$, $NR^5$—CO, $CR^5{}_2$—$CR^5{}_2$, or $CR^5$=$CR^5$. More preferably, E is O—$CR^5{}_2$, $NR^5$—CO, or $CR^5$=$CR^5$.

In another preferred embodiment of sub-group $F^2$, $R^5$ is/are each independently H or $C_{1-4}$alkyl.

In another embodiment, the present invention provides a further sub-group of compounds (Group G) represented by formula (I) or pharmaceutically acceptable salts thereof: wherein:

R¹ is —H,
C$_{1-12}$alkyl optionally substituted with 1, 2 or 3 groups independently selected from halogen, hydroxyl, thiol, C$_{1-4}$alkoxy or C$_{1-4}$alkylthio, or aryl-C$_{1-4}$alkyl;
R² is linked back to the aromatic ring so as to form a fused bicyclic compound represented by Formula (Ib)

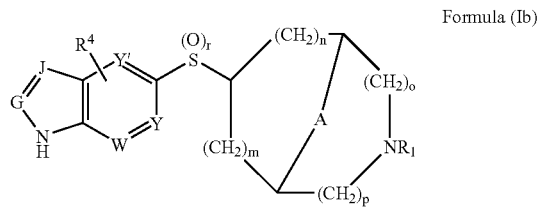

Formula (Ib)

wherein G is CR⁵ or N; and
J is CR⁵ or N;
R³ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R⁴ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R⁵ is each independently H or C$_{1-4}$alkyl;
X is C;
W is C or N;
Y is C or N;
Y' is C or N
provided that there are no more than two N atoms in the aryl ring;
A is optionally a double bond or (CH$_2$)$_q$ or (CH$_2$)O(CH$_2$);
m, n, o and p are independently 0, 1, 2 or 3;
q is optionally 1, 2 or 3;
r is 0, 1 or 2.

In a preferred embodiment of sub-group G, each R⁵ is H.
Within Group A, the sum of m, n, o and p is preferably 2. More preferably, m and n are 1; o and p are 0.
Within Group A, q is preferably 2.
Within Group A, X, Y and Z are preferably C.
For all embodiments of the present invention (except Group A, for which r is 0) r is preferably 0 or 2, and most preferably 0.
For all embodiments of the present invention, R¹ is preferably H or C$_{1-3}$alkyl, more preferably methyl.
For all embodiments of the present invention, A is preferably CH$_2$, CH$_2$CH$_2$ or CH=CH. More preferably, for all embodiments A is CH$_2$CH$_2$. Also preferred, for all embodiments is when A is CH=CH.
For all embodiments of the present invention, the sum of m, n, o and p is preferably 2. More preferably, m and n are 1; o and p are 0.
For all embodiments of the present invention it is preferred that m and n are 1, o and p are 0 and A is CH$_2$CH$_2$ or CH=CH.

For all embodiments of the present invention, R³ is preferably H, halogen, C$_{1-4}$alkyl, cyano, CF$_3$, or OC$_{1-4}$alkyl, and R⁴ is preferably H, halogen, C$_{1-4}$alkyl, cyano, CF$_3$, or OC$_{1-4}$alkyl.
For all embodiments of the present invention, one or both of R³ and R⁴ are preferably positioned ortho to the S(O)$_r$ moiety.
For all embodiments of the present invention, one or both of R³ and R⁴ are preferably halogen, C$_{1-4}$alkyl, cyano, CF$_3$, or OC$_{1-4}$alkyl, more preferably halogen, cyano, or C$_{1-4}$alkyl, most preferably halogen, positioned ortho to the S(O)$_r$ moiety.

As used herein, the term "alkyl" means a branched or unbranched, cyclic and/or acyclic, saturated or unsaturated (e.g. alkenyl or alkynyl), monovalent or divalent hydrocarbyl radical. Examples of branched alkyl groups are isopropyl, isobutyl, tert-butyl etc. Examples of cyclic alkyl groups are cyclopropyl, cyclobutyl, cyclopentyl, cycohexyl, adamantyl etc. Examples of groups containing both cyclic and acyclic alkyl moieties are cyclopropylmethyl, cyclohexylpropyl, adamantylethyl etc.

As used herein, the term "aryl" means a C$_3$ to C$_{26}$, preferably C$_3$ to C$_{12}$ aromatic or heteroaromatic group which may, optionally, be substituted with one or more substituents. Aryl substituents are preferably selected from C$_1$ to C$_{12}$ alkyl (preferably C$_1$ to C$_6$ alkyl), C$_1$ to C$_{12}$ alkoxy (preferably C$_1$ to C$_6$ alkoxy), thio, C$_1$ to C$_{12}$ alkylthio (preferably C$_1$ to C$_6$ alkylthio), carboxy, carboxy(C$_1$ to C$_6$)alkyl, formyl, C$_1$ to C$_6$ alkylcarbonyl, C$_1$ to C$_6$ alkylsulfonyl, C$_1$ to C$_6$ alkylcarbonylalkoxy, nitro, trihalomethyl, trihalo(C$_1$ to C$_6$ alkoxy), trihalomethoxy, trihalomethyl(C$_1$ to C$_6$ alkyl), hydroxy, hydroxy(C$_1$ to C$_6$)alkyl, (C$_1$ to C$_6$ alkoxy)carbonyl, amino, C$_1$ to C$_6$ alkylamino, di(C$_1$ to C$_6$ alkyl)amino, aminocarboxy, C$_1$ to C$_6$ alkylaminocarboxy, di(C$_1$ to C$_6$ alkyl) aminocarboxy, aminocarboxy(C$_1$ to C$_6$)alkyl, C$_1$ to C$_6$ alkylaminocarboxy(C$_1$ to C$_6$)alkyl, di(C$_1$ to C$_6$ alkyl) aminocarboxy(C$_1$ to C$_6$)alkyl, C$_1$ to C$_6$ alkylcarbonylamino, C$_1$ to C$_6$ alkylcarbonyl(C$_1$ to C$_6$ alkyl)amino, halo, C$_1$ to C$_6$ alkylhalo, sulphamoyl, tetrazolyl and cyano.

Examples of aromatic groups are phenyl, naphthyl, fluorenyl, thienyl, furanyl, pyrrolyl, imidazolyl, pyrazolyl, thiazolyl, isothiazolyl, oxazolyl, isoxazolyl, oxadiazolyl, thiadiazolyl, diazolyl, triazolyl, tetrazolyl, benzothiazolyl, benzimidazolyl, pyrrolinyl, imidazolinyl, pyranyl, pyronyl, pyridyl, pyrazinyl, pyridazinyl, thianaphthyl, benzofuranyl, isobenzofuranyl, benzothienyl, isobenzothienyl, indolyl, oxyindolyl, isoindolyl, indazolyl, indolinyl, 7-azaindolyl, azabenzimidazolyl, carbazolyl benzopyranyl, coumarinyl, isocoumarinyl, quinolinyl, isoquinolinyl, quinazolinyl, benzoxazinyl, quinoxalinyl, chromenyl, chromanyl, isochromanyl, phthalazinyl, benzodioxolyl, benzodioxanyl, cinnolinyl and carbolinyl.

Terms such as "aryl-C$_{1-12}$ alkyl group" include groups such as benzyl, 4-chlorobenzyl, phenylpropyl, thienylethyl etc. Further, the alkyl moiety in, for example, aryl-C$_{1-12}$ alkyl groups may optionally be substituted with 1, 2 or 3 substituents selected from halogen, hydroxyl, C$_{1-4}$ alkoxy or C$_{1-4}$ alkylthio.

As used herein the term "lactonyl" means any C$_{1-18}$ cyclic ester. The lactonyl group may be monocyclic or polycyclic.

As used herein, the terms "halogen" or "halo" refer to any one of F, Cl, Br or I.

Compounds of Group A wherein
R²=OH; and
R³=methyl, CF$_3$, halogen or H; may be prepared by a procedure exemplified in Reaction Scheme 1.

While Reaction Scheme 1 exemplifies compounds of the present invention wherein m=n=1, it will be readily apparent to the skilled person that the same procedures may be applied to other ring sizes (i.e. when the sum of m, n, o and p is 3 or more).

Reaction Scheme 1

L = suitable leaving group

Thiophenol (1) [commercial or prepared according to Kita Y.; Takeda, Y.; Okuno, T.; Egi, M.; Ito, K.; Kawaguchi, K; Akai, S. *Chem. Pharm. Bull.* 1997, 45(12), 1887–1890 or Zheng, J.; Hanzlik, R. P. *Drug Metab. Dispos.* 1992, 20(5), 688–694], is coupled with carbamate (2) by displacement of the leaving group L. Suitable leaving groups will be readily apparent to the person skilled in the art. Typical leaving groups include iodo, chloro, bromo, mesyl or tosyl. The coupling reaction is preferably performed in a dipolar solvent such as methanol, THF or DMF. More preferably, the coupling reaction is performed in a 50/50 mixture of THF and DMF. The coupling reaction is preferably promoted by a suitable base such as potassium hydroxide, sodium hydride, sodium ethoxide, potassium carbonate or DBU. More preferably, the coupling reaction is performed in the presence of potassium carbonate or sodium hydride. Typically the coupling reaction may be carried out over a temperature range of from −78 to 150° C. Preferably, the reaction is carried out at a temperature in the range of from room temperature to 70° C. Reaction times for the coupling reaction are typically from 10 minutes to 24 hours. Preferred reaction times are in the range of 30 minutes to 12 hours.

Thioether (3) is subsequently converted into compounds of the present invention corresponding to the thioether of formula (4). When $R^1$ is methyl, compounds of formula (4) may be prepared by reduction using, for example, lithium aluminium hydride. When $R^1$ is other than methyl, compounds of formula (4) may be prepared by deprotection of the carbamate group (usually under acidic conditions) followed by reaction with a suitable aldehyde or allyl halide.

Reduction with lithium aluminium hydride is typically carried out in ether or TBF (preferably TBF). Preferably, the reduction is carried out at room temperature. Reaction times vary from 10 minutes to up to several days. Preferred reaction times are in the range of 12 to 48 hours.

Alternatively, when $R^1$ is other than methyl, the carbamate derivative (3) is deprotected under standard conditions. Typical carbamate deprotection conditions involve using either protic acids (e.g. trifluoroacetic acid, HCl, HBr) or Lewis acids (e.g. acid chlorides/bromides, tri(m)ethylsilyl triflate). The solvent used is typically water, dichloromethane, dioxane, THF or ether. Preferably, an acid chloride in dioxane is used when the protecting group is tert-butyl carbamate (Boc). Preferably, HBr in water is used when the protecting group is ethyl carbamate. Preferably, deprotection is carried out at room temperature (in the case of Boc-deprotection) or at reflux (in the case of ethyl carbamate).

Once a free amine has been realised following deprotection, procedures for introducing various $R^1$ groups (wherein $R^1$ is optionally substituted $C_{1-12}$ alkyl or aryl-$C_{1-4}$ alkyl) will be readily apparent to the skilled person. Generally, displacement of an alkyl halide (or reductive alkylation with an aldehyde) furnishes the desired tertiary amine (4).

Compounds of Group A wherein:
$R^1$=methyl;
$R^2$=—$NH_2$ or —NH-Q-V-T; and
$R^3$=H May be prepared by a procedure exemplified in Reaction Scheme 2.

While Reaction Scheme 2 exemplifies compounds of the present invention wherein m=n=1, it will be readily apparent to the skilled person that the same procedures may be applied to other ring sizes (i.e. when the sum of m, n, o and p is 3 or more).

Reaction Scheme 2

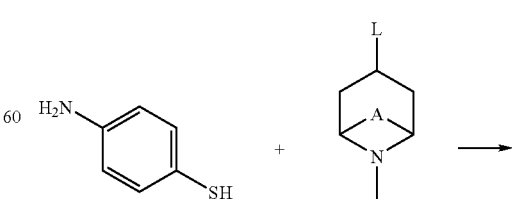

L = suitable leaving group

-continued

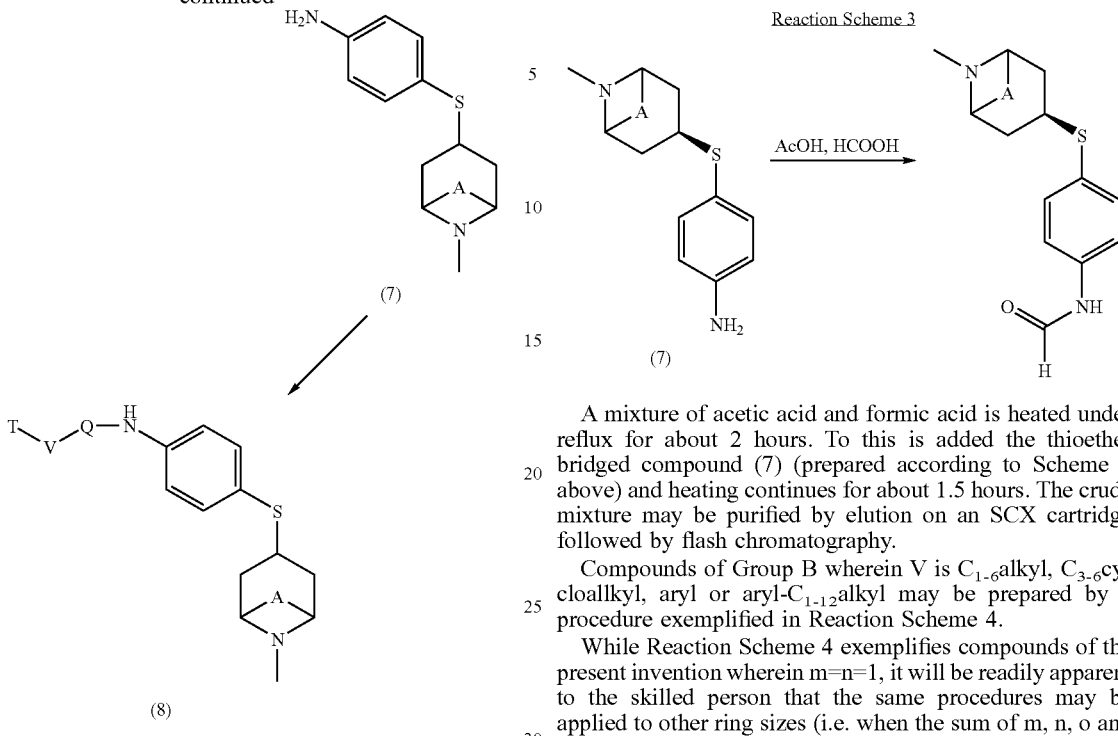

Commercially available 4-aminothiophenol (5) is coupled with amine (6) by displacement of a suitable leaving group L, as outlined above in Reaction Scheme 1. The resultant thioether bridged compound (7) is a key intermediate in the synthesis of compounds of the present invention. It will be readily apparent to the person skilled in the art that various $R^2$ groups of general type —NH-Q-V-T may be prepared from compound (7) by standard procedures known in the art. For example, when:

(a) Q is —SO$_2$—, by coupling with a compound of general formula T-V—SO$_2$-L';

(b) Q is —CO—, by coupling with a compound of general formula T-V—CO-L';

(c) Q is —NH—C(O)—, by coupling with a compound of general formula T-V—N=C=O;

(d) Q is —OC(O)—, by coupling with a compound of general formula T-V—OC(O)—L' wherein L' is any suitable leaving group, such as Cl, Br, or I.

Typically, the coupling reaction which affords compounds of formula (8) is performed in pyridine or an aprotic solvent such as dichloromethane in the presence of a base such as sodium hydride, pyridine, triethylamine or diisopropylamine. Preferably, the coupling is performed at room temperature with reaction times varying from 10 minutes to 24 hours, preferably 30 minutes to 12 hours.

Compounds of Group B wherein V is H may be prepared by a procedure exemplified in Reaction Scheme 3.

While Reaction Scheme 3 exemplifies compounds of the present invention wherein m=n=1, it will be readily apparent to the skilled person that the same procedures may be applied to other ring sizes (i.e. when the sum of m, n, o and p is 3 or more).

A mixture of acetic acid and formic acid is heated under reflux for about 2 hours. To this is added the thioether bridged compound (7) (prepared according to Scheme 2 above) and heating continues for about 1.5 hours. The crude mixture may be purified by elution on an SCX cartridge followed by flash chromatography.

Compounds of Group B wherein V is $C_{1-6}$alkyl, $C_{3-6}$cycloalkyl, aryl or aryl-$C_{1-12}$alkyl may be prepared by a procedure exemplified in Reaction Scheme 4.

While Reaction Scheme 4 exemplifies compounds of the present invention wherein m=n=1, it will be readily apparent to the skilled person that the same procedures may be applied to other ring sizes (i.e. when the sum of m, n, o and p is 3 or more).

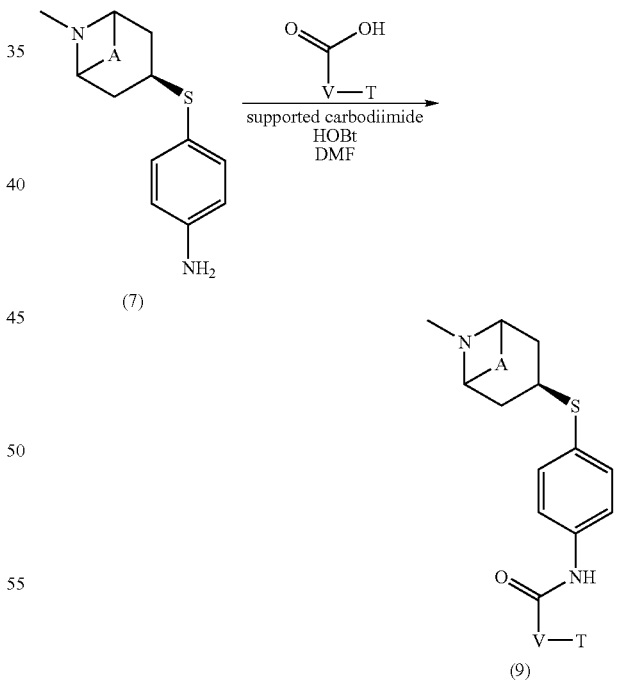

A mixture of the thioether bridged compound (7) (prepared according to Scheme 2 above), T-V—CO$_2$H, 1-hydroxybenzotriazole and carbodiimide resin in DMF is stirred at room temperature for about 3 days. The mixture is filtered then passed through an SCX cartridge to provide the product (9).

Compounds of Group C wherein $R^2$ is NH$_2$ may be prepared by a procedure exemplified in Reaction Scheme 5.

While Reaction Scheme 5 exemplifies compounds of the present invention wherein m=n=1, and W is N, it will be readily apparent to the skilled person that the same procedures may be applied to other ring sizes (i.e. when the sum of m, n, o and p is 3 or more) or where Y is N.

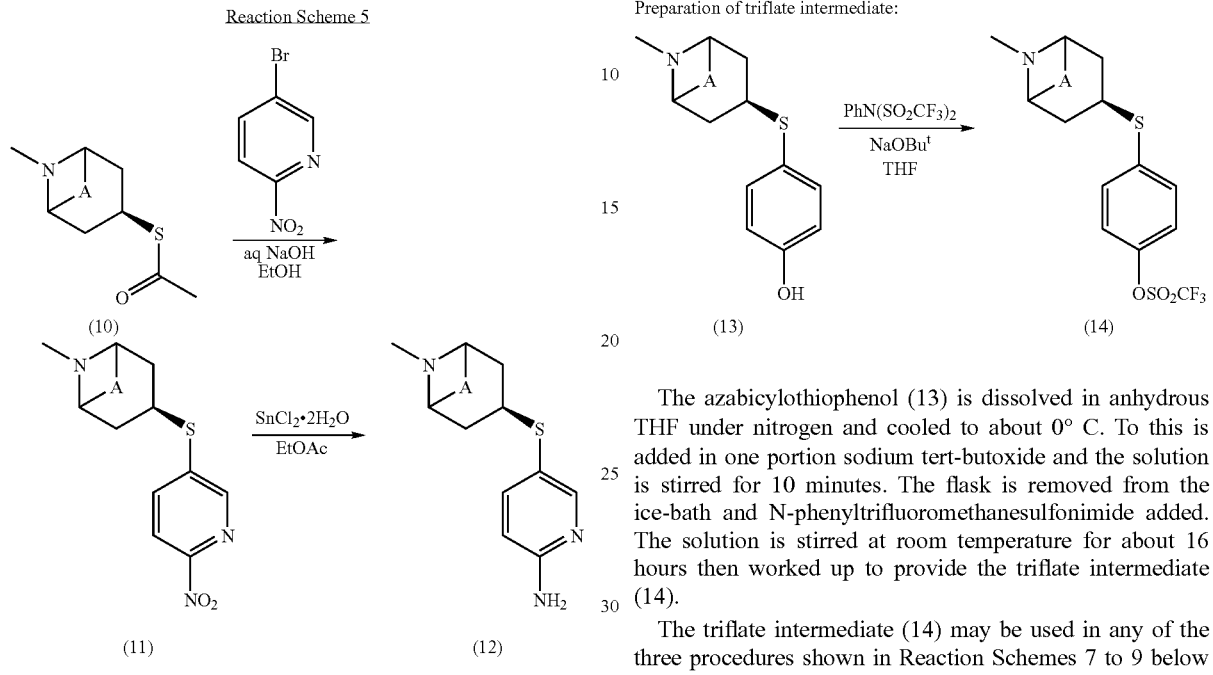

Step 1:
A mixture of the ethanethioate (10) and 2-nitro-5-bromopyridine in ethanol and aqueous sodium hydroxide is stirred at room temperature for about 18 hours. The mixture is applied directly to an SCX cartridge and eluted to yield the crude product which may be purified by preparative LC-MS to provide the nitro-pyridinyl-thio-azabicyclo compound (11).

Step 2:
A mixture of the nitro-pyridinyl-thio-azabicyclo compound (11) and tin (II) chloride dihydrate in ethyl acetate is heated under reflux for about 4 days and then worked up by quenching with aqueous sodium hydrogen carbonate solution to provide the aminopyridine product (12). Step 2 may also be achieved by Pd/C catalysed $H_2$ reduction It will be readily apparent to the person skilled in the art that compounds of Group C wherein $R^2$ is —NH-Q-V-T may be prepared from compound (12) by standard procedures known in the art. For example, when:

(e) Q is —$SO_2$—, by coupling with a compound of general formula T-V—$SO_2$-L';
(f) Q is —CO—, by coupling with a compound of general formula T-V—CO-L';
(g) Q is —NH—C(O)—, by coupling with a compound of general formula T-V—N=C=O;
(h) Q is —OC(O)—, by coupling with a compound of general formula T-V—OC(O)—L' wherein L' is any suitable leaving group, such as Cl, Br, or I.

Compounds of Group D ($R^2$ is aryl) may be prepared by a procedure exemplified in Reaction Schemes 6 to 9

While Reaction Schemes 6 to 9 exemplify compounds of the present invention wherein m=n=1, it will be readily apparent to the skilled person that the same procedures may be applied to other ring sizes (i.e. when the sum of m, n, o and p is 3 or more).

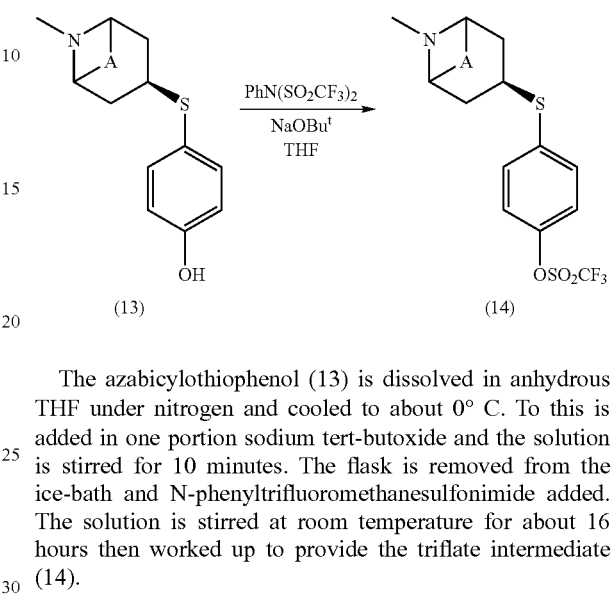

The azabicylothiophenol (13) is dissolved in anhydrous THF under nitrogen and cooled to about 0° C. To this is added in one portion sodium tert-butoxide and the solution is stirred for 10 minutes. The flask is removed from the ice-bath and N-phenyltrifluoromethanesulfonimide added. The solution is stirred at room temperature for about 16 hours then worked up to provide the triflate intermediate (14).

The triflate intermediate (14) may be used in any of the three procedures shown in Reaction Schemes 7 to 9 below to provide compounds of Group D.

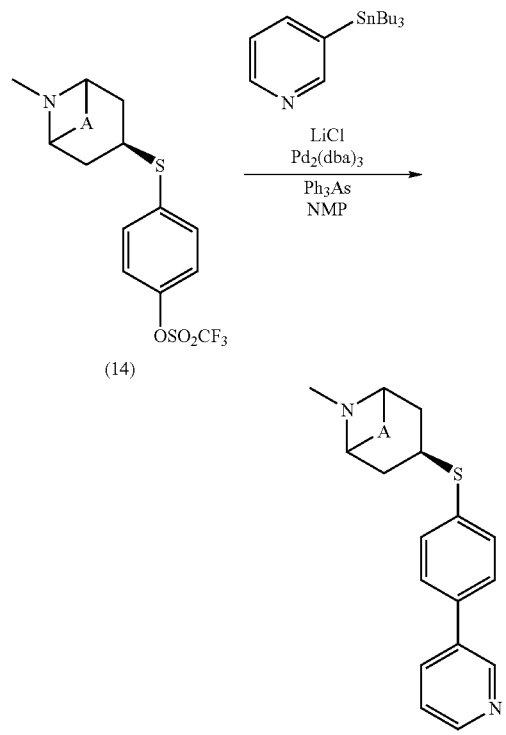

A mixture of the triflate (14), lithium chloride, triphenylarsine and tris(dibenzylideneacetone)-dipalladium (0) is stirred in N-methylpyrrolidinone under nitrogen. To this is added 3-tributylstannylpyridine and the solution heated to 100° C. The solution is cooled to room temperature and aqueous sodium hydroxide added to quench the reaction. The mixture is worked up and purified to yield a Group D compound wherein $R^2$ is pyridinyl.

Representative example of a Stille coupling with microwave assistance

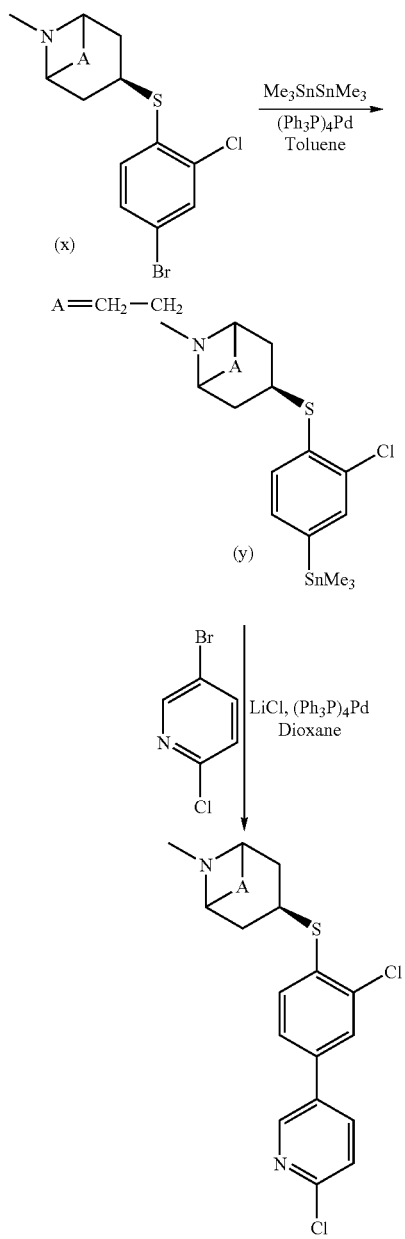

Step 1:

A mixture of 3-[(4-bromo-2-chlorophenyl)thio]-8-methyl-8-azabicyclo[3.2.1]octane (x) (670 mg), hexamethylditin (696 mg) and tetrakis(triphenylphosphine) palladium (0) (112 mg) in dry toluene (5 ml) under nitrogen is subjected to microwave irradiation (200 W, 110° C.) in a sealed vessel. After evaporation, the crude material was purified on an Isco CombiFlash device to yield 3-{[2-chloro-4-(trimethylstannyl)phenyl]thio}-8-methyl-8-azabicyclo[3.2.1]octane (570 mg).

Step 2:

A mixture of 3-{[2-chloro-4-(trimethylstannyl)phenyl]thio}-8-methyl-8-azabicyclo[3.2.]octane (y) (153 mg), 2-chloro-5-bromopyridine (67 mg), lithium chloride (45 mg) and tetrakis(triphenylphosphine) palladium (0) (20 mg) in dioxane (1 ml is subjected to microwave irradiation (200W, 105° C.) in a sealed vessel. After evaporation, the material is purified by passage through an SCX cartridge followed by preparative LC-MS to yield 3-{[2-chloro-4-(6-chloropyridin-3-yl)phenyl]thio}-8-methyl-8-azabicyclo[3.2.1]octane (27 mg)

Reaction Scheme 8

Representative example of an "in situ" Stille coupling:

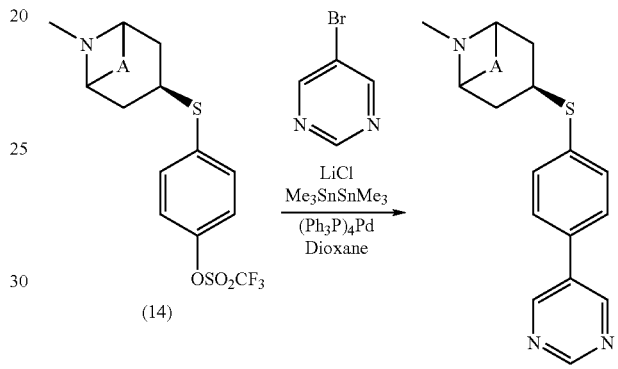

To a mixture of the triflate (14), 5-bromopyrimidine, lithium chloride and tetrakis(triphenylphosphine) palladium (0) under nitrogen is added hexamethylditin and dioxane. The mixture is heated under reflux and then poured into a mixture of aqueous potassium fluoride and ethyl acetate. This mixture is stirred vigorously, passed through a sintered funnel and the layers separated. The organic phase is worked up and purified to yield a Group D compound wherein $R^2$ is pyrimidinyl.

Reaction Scheme 9

Representative example of a Suzuki coupling:

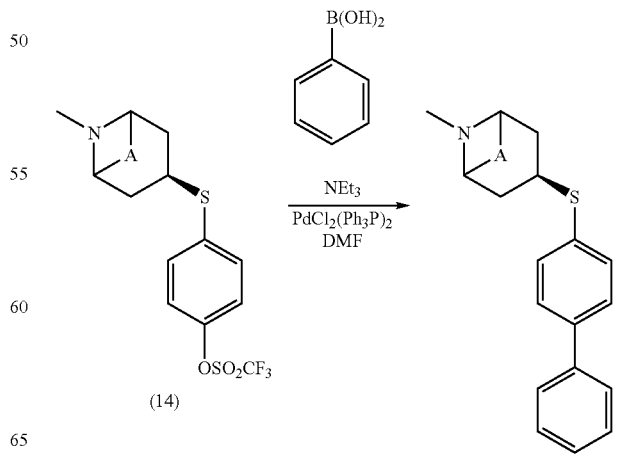

To a mixture of the triflate (14) and phenylboronic acid in DMF is added followed by dichlorobis(triphenylphosphine) palladium (II). The solution is heated at about 90° C. for about 4 hours, cooled to room temperature and diluted with ethyl acetate. The reaction mixture is worked up and purified to a Group D compound wherein $R^2$ is phenyl.

Compounds of Group E ($R^2$ is $(L)_a$-Z) may be prepared by a procedure exemplified in Reaction Schemes 10 to 13.

While Reaction Schemes 10 to 13 exemplify compounds of the present invention wherein m=n=1, it will be readily apparent to the skilled person that the same procedures may be applied to other ring sizes (i.e. when the sum of m, n, o and p is 3 or more).

Reaction Scheme 10

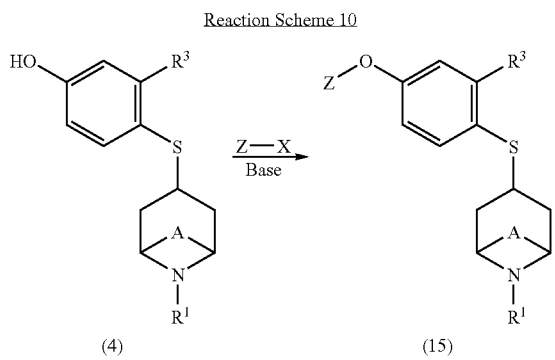

Reaction Scheme 11

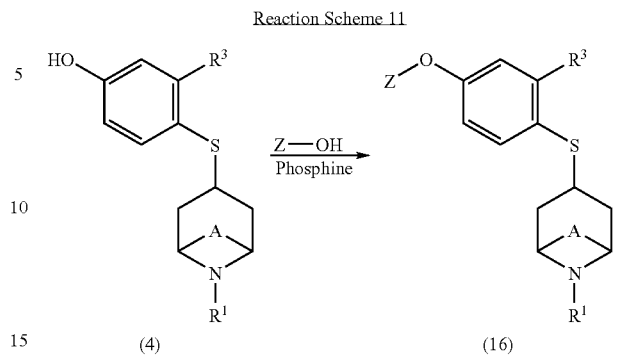

Phenol (4) is coupled with a compound of formula Z-X wherein X is a suitable leaving group such halogen, trifluoromethanesulfonyl, tosyl or mesyl and Z is $C_{1-3}$alkyl-F, $C_{0-3}$alkyl-aryl-$R^6$, $C_{1-3}$alkyl-CN, $C_{0-3}$alkyl-CO—$R^6$, $C_{0-3}$alkyl-CO—$NR^6{}_2$, $C_{0-3}$alkyl-$CO_2$—$R^6$, $C_{0-3}$alkyl-$SO_2$—$R^6$, $C_{0-3}$alkyl-$SO_2$—$NR^6{}_2$, $C_{1-3}$alkyl-$OR^6$ or $C_{1-3}$alkyl-$NR^6{}_2$, wherein each $C_{0-3}$alkyl or $C_{1-3}$alkyl portion is optionally substituted with from 1 to 6 groups selected from F and $C_{1-5}$alkyl.

The coupling reaction is preferably performed in a dipolar solvent such as ethanol, THF, DMSO, acetonitrile or DMF. More preferably the reaction is performed in DMF or DMSO. The coupling reaction is preferably promoted by a suitable base such as potassium hydroxide, sodium hydride, sodium ethoxide, cesium carbonate, potassium carbonate, potassium fluoride, BEMP, polystyrene-supported BEMP or DBU. More preferably, the coupling reaction is performed in the presence of cesium carbonate, potassium fluoride, sodium hydride or polystyrene-supported BEMP. Typically the coupling reaction may be carried out over a temperature range of from −78 to 150° C. Preferably, the reaction is carried out at a temperature in the range of from room temperature to 70° C. Reaction times for the coupling reaction are typically from 10 minutes to 24 hours. Preferred reaction times are in the range of 30 minutes to 12 hours. In some cases microwaves were applied.

Alternatively, some of the above compounds may be used as key intermediates for other compounds of the subgroup E with methods known by those skilled in the art.

Phenol (4) is coupled with a compound of formula Z-OH wherein Z is $C_{1-3}$alkyl-F, $C_{1-3}$alkyl-aryl-$R^6$ wherein the $C_{1-3}$alkyl portion is optionally substituted with from 1 to 6 groups selected from F and $C_{1-5}$alkyl.

A mixture solution of the phenol (4) was treated with the corresponding alcohol derivative, a phosphine derivative and a diazacarboxylate derivative under microwaves conditions in a polar solvent such as DMF at 150° C. over 1–4 hours. The reaction mixtures were passed through SCX cartridge eluting with methanol and then 2M ammonia in methanol and concentrated to dryness. The materials were then further purified by preparative LC-MS.

Reaction Scheme 12

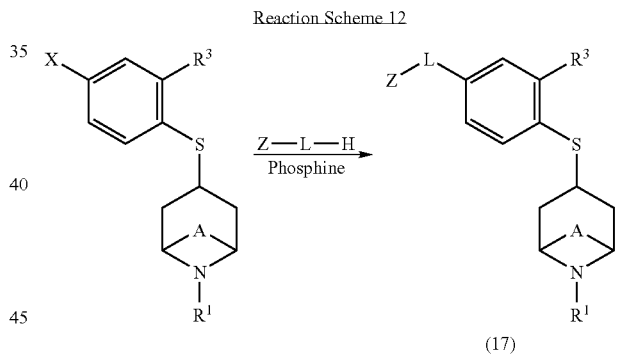

Phenol derivative, wherein X is trifluoromethanesulfonyl, iodo, chloro or bromo, is coupled with a compound of formula Z-L-H wherein L is NH or N($C_{1-4}$alkyl), Z is $C_{1-3}$alkyl-F, $C_{0-3}$alkyl-aryl-$R^6$, $C_{0-3}$alkyl-CN, $C_{0-3}$alkyl-CO—$R^6$, $C_{0-3}$alkyl-CO—$NR^6{}_2$, $C_{0-3}$alkyl-$CO_2$—$R^6$, $C_{0-3}$alkyl-$SO_2$—$R^6$, $C_{0-3}$alkyl-$SO_2$—$NR^6{}_2$, $C_{1-3}$alkyl-$OR^6$ or $C_{1-3}$alkyl-$NR^6{}_2$ wherein each $C_{0-3}$alkyl or $C_{1-3}$alkyl portion is optionally substituted with from 1 to 6 groups selected from F and $C_{1-5}$alkyl.

A derivative of Pd (0), a phosphine ligand and a suitable base such $CsCO_3$ were charged in a schlenk flask evacuated and filled with argon. Then the corresponding aryl derivative, more preferably (13), with the desired amine were added under argon. The reaction was carry out in an organic solvent such as THF or toluene and the mixture was heating at 100° C. overnight. The reaction was concentrated in vacuo and purified in $SiO_2$ to obtain the final compounds.

Reaction Scheme 13

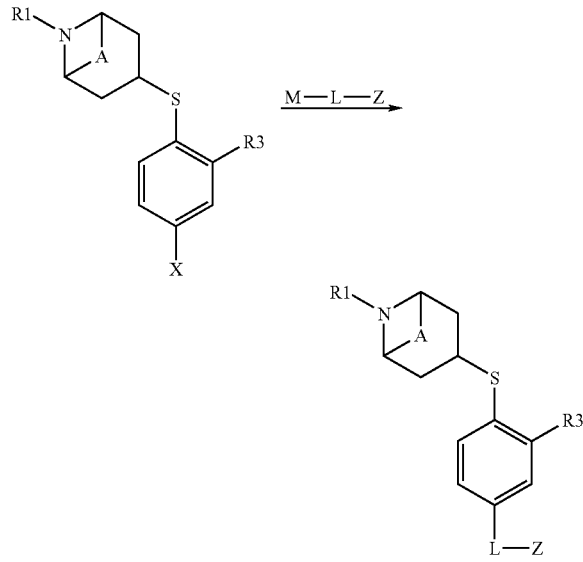

The intermediate thiobenzene, more preferably triflate (14), is coupled with compounds M-L-Z by displacement of M using palladium (II) salts as a catalyst and in the presence of phosphines. Suitable palladium (II) salts will be readily apparent to the person skilled in the art. The coupling reaction is performed in an organic solvent such as methanol, dioxane, acetonitrile, THF or DMF. Typically the coupling reaction may be carried out over a temperature range of from 0 to 150° C. Preferably, the reaction is carried out at a temperature in the range of from room temperature to 100° C. Reaction times for the coupling reaction are from 3 hours to 48 hours.

In this scheme, M is H or metal, X is Cl, Br, I, or trifluoromethanesulfonyl, L is $C_1$alkyl and Z is $C_{1-3}$alkyl-F, $C_3$alkyl-aryl-$R^6$, $C_{1-3}$alkyl-CN, $C_{1-3}$alkyl-CO—$R^6$, $C_{1-3}$alkyl-CO—$NR^6{}_2$, $C_{1-3}$alkyl-$CO_2$—$R^6$, $C_{1-3}$alkyl-$SO_2$—$R^6$, $C_{1-3}$alkyl-$SO_2$—$NR^6{}_2$, $C_{1-3}$alkyl-$OR^6$ or $C_{1-3}$alkyl-$NR^6{}_2$ wherein the $C_{1-3}$alkyl portion is optionally substituted with from 1 to 6 groups selected from F and $C_{1-5}$alkyl.

The intermediate thiobenzene, more preferably triflate (14), is coupled with compounds M-L-Z by displacement of M using palladium (II) salts as a catalyst and in the presence of phosphines. Suitable palladium (II) salts will be readily apparent to the person skilled in the art. The coupling reaction is performed in an organic solvent such as methanol, dioxane, acetonitrile, THF or DMF. Typically the coupling reaction may be carried out over a temperature range of from 0 to 150° C. Preferably, the reaction is carried out at a temperature in the range of from room temperature to 100° C. Reaction times for the coupling reaction are from 3 hours to 48 hours.

Alternatively, some of the above compounds may be used as key intermediates for other compounds of the subgroup E with methods known by those skilled in the art.

Compounds of Group $F^1$ and $F^2$ may be prepared by procedures exemplified in Reaction Schemes 14 to 17. While the Schemes exemplify compounds of the present invention wherein m=n=1, it will be readily apparent to the skilled person that the same procedures may be applied to other ring sizes (i.e. when the sum of m, n, o and p is 3 or more).

Reaction Scheme 14

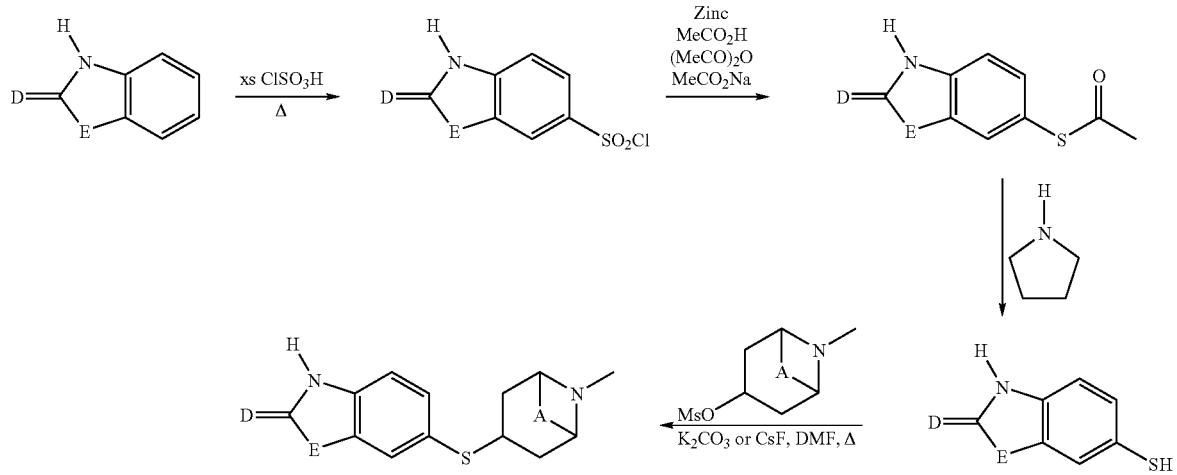

Unsubstituted precursors to compounds of group $F^1$ and $F^2$ (wherein $R^3$=H, $R^4$=H, D=O or S and E=O, S, NH, O—$CR^5{}_2$, $NR^5$—$CR^5{}_2$, $NR^5$—CO, $CR^5{}_2$—O, $CR^5{}_2$—S, $CR^5{}_2$—$NR^5$, $CR^5{}_2$—$CR^5{}_2$, CO—$NR^5$, or $CR^5$=$CR^5$) may be treated with excess chlorosulphonic acid to selectively introduce a chlorosulphonyl group para to the N—H. The chlorosulphonic acid may be used neat or in a solvent such as chloroform or dichloromethane at a temperature between 0 and 100° C. Reduction to the acetylthio compound may be effected with zinc, acetic anhydride and acetic acid at a temperature between 0° C. and ambient temperature. Removal of the acetyl group may be effected by a secondary amine such as pyrollidine and subsequent alkylation of the free thiol with an appropriate mesylate may be mediated by a base such as potassium carbonate or cesium fluoride in an aprotic solvent such as dimethylformamide. This reaction is performed between ambient temperature and 100° C. It will be appreciated by those skilled in the art that exo and endo isomers may be obtained and these can be separated by crystallisation or chromatography.

An alternative route to aryl thiols is shown in scheme 15 for D=E=O and $R^3$=Me. This utilises 1 equivalent of chlorosulphonic acid at 0° C. and ambient temperature to give a sulphonic acid derivative which may be reduced directly to a thiol using iodine and triphenylphosphine in a solvent such as benzene at reflux under Dean and Stark conditions.

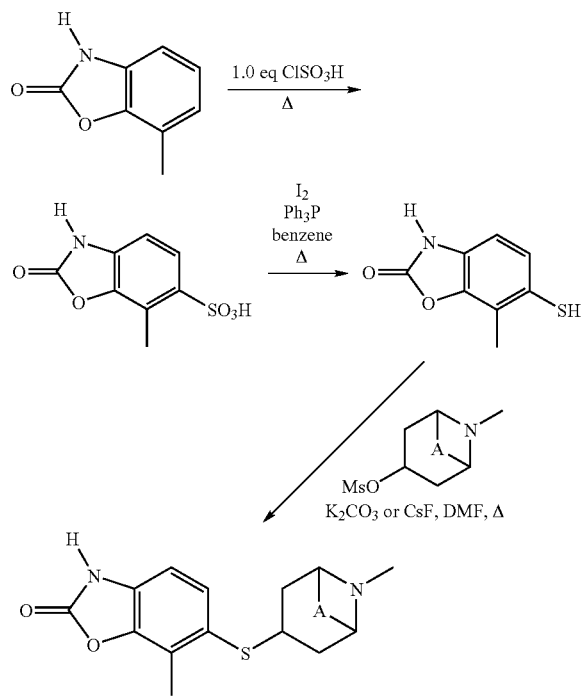

Substituted compounds of group $F^1$ and $F^2$ ($R^3$=H, Cl, $R^4$=H, D=O, S and E=O, S, $NR^5$, O—$CR^5_2$, $NR^5$—$CR^5_2$, $NR^5$—CO) may be prepared by a route exemplified in Scheme 16.

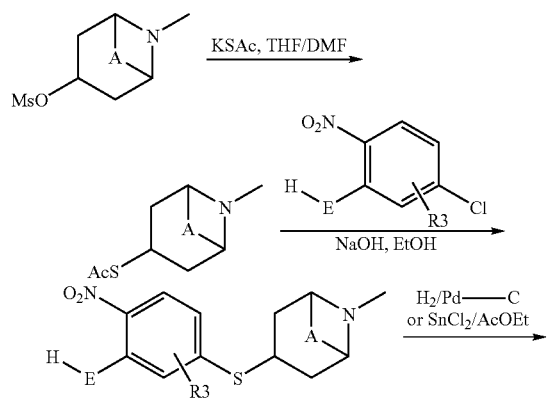

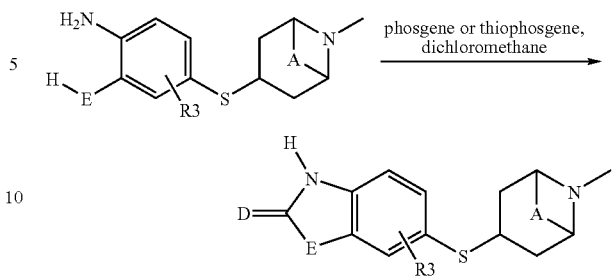

Reaction of a mesylate with potassium thioacetate in an aprotic solvent such as a mixture of dimethylformamide and tetrahydrofuran at temperatures between ambient and 80° C. gives rise to an acetylthio derivative. It will be appreciated by those skilled in the art that exo and endo isomers may be obtained and these can be separated by chromatography. These compounds may be used to displace a halo atom (eg chlorine) from an appropriately substituted nitrophenyl derivative in a reaction mediated by a nucleophilic base such as hydroxide at ambient temperature. The resultant nitro derivative may be reduced by catalytic hydrogenation in a protic solvent such as ethanol or by tin chloride in ethyl acetate at reflux temperature. Finally reaction with phosgene (or a synthetic equivalent eg triphosgene) or thiophosgene in a solvent such a s dichloromethane or chloroform at a temperature between ambient and reflux temperature gives rise to the compounds of group $F^1$ and $F^2$ specified.

Compounds of Group $F^2$ where D=O, E=$CR^5$=$CR^5$ and $R^3$=$R^4$ may be prepared by a procedure exemplified in Reaction Scheme 17.

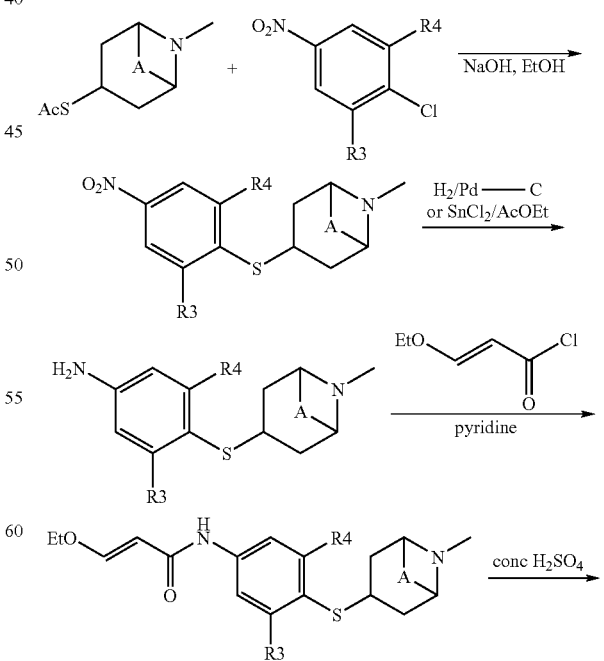

-continued

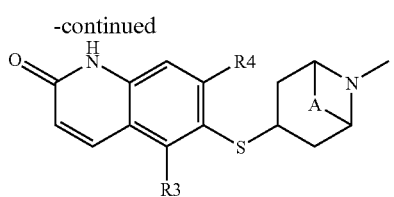

An acetylthio compound may be used to displace a halo atom (eg chlorine) from an appropriately substituted nitrophenyl derivative in a reaction mediated by a nucleophilic base such as hydroxide at ambient temperature. The resultant nitro derivative may be reduced by catalytic hydrogenation in a protic solvent such as ethanol or by tin chloride in ethyl acetate at reflux temperature. The aniline derivative so obtained is acylated with (E)-3-ethoxy-2-propenoyl chloride in a solvent such as dichloromethane in the presence of a non-nucleophilic base such as pyridine at a temperature between 0° C. and ambient temperature. The resultant amide may be cyclized with a concentrated mineral acid such sulphuric acid at a temperature between 0° C. and ambient temperature.

Compounds of Group G may be prepared by procedures exemplified in Reaction Schemes 18 to 19. While the Schemes exemplify compounds of the present invention wherein m=n=1, it will be readily apparent to the skilled person that the same procedures may be applied to other ring sizes (i.e. when the sum of m, n, o and p is 3 or more).

Compounds of group G where G is $CR^5$ or N; and J is $CR^5$ or N may be prepared by the route exemplified in Scheme 18.

Reaction Scheme 18

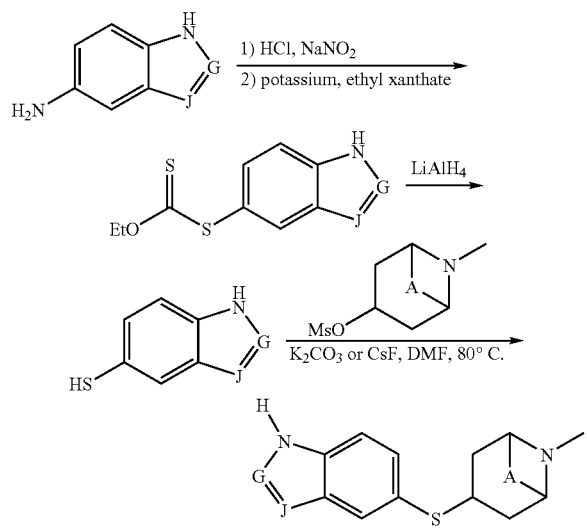

An appropriate amino derivative is diazotised under standard conditions (sodium nitrite, hydrochloric acid at or around 0° C.) and treated with potassium ethyl xanthate in water at or around 80° C. The resulting xanthate may be converted to a thiol using a reducing agent such as lithium aluminium hydride in an aprotic solvent such as diethyl ether or tetrahydrofuran at a temperature between 0° C. and ambient temperature. Subsequent alkylation of the thiol with an appropriate mesylate may be mediated by a base such as potassium carbonate or cesium fluoride in an aprotic solvent such as dimethylformamide. This reaction is performed between ambient temperature and 100° C. It will be appreciated by those skilled in the art that exo and endo isomers may be obtained and these can be separated by crystallisation or chromatography.

A subgroup of compounds of the type G where $J=CR^5$, $G=N$ and $R^3=Cl$ may be prepared by a route shown in Scheme 19.

Reaction Scheme 19

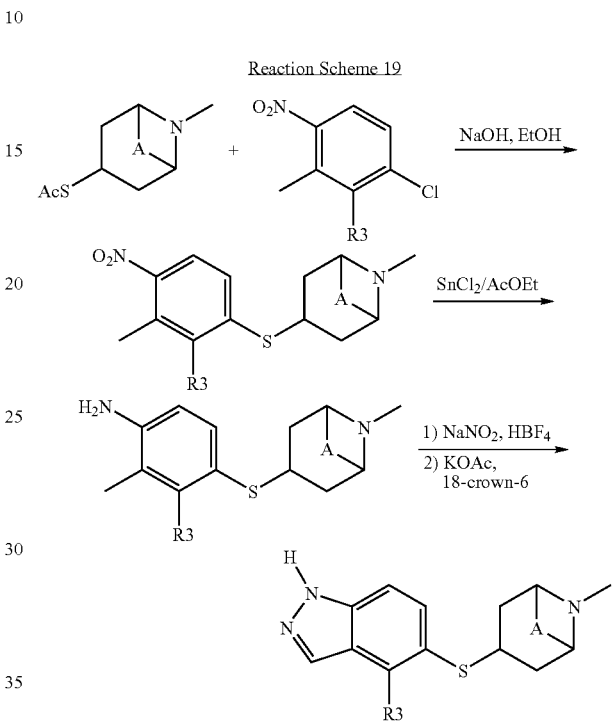

An acetylthio compound may be used to displace a halo atom (eg chlorine) from an appropriately substituted ortho-nitrotoluene derivative in a reaction mediated by a nucleophilic base such as hydroxide at ambient temperature. The resultant nitro derivative may be reduced by tin chloride in ethyl acetate at reflux temperature. This is followed by reaction with sodium nitrate in aqueous fluorboric acid at a temperature between 0° C. and ambient temperature. Treatment of the subsequent diazonium tetrafluoroborate salt with potassium acetate and 18-crown-6 in a solvent such as chloroform at ambient temperature gives the appropriate indazole derivatives.

The oxidation of sulfides to sulfones may be achieved by reaction with oxone as shown in Reaction Scheme 20.

Reaction Scheme 20

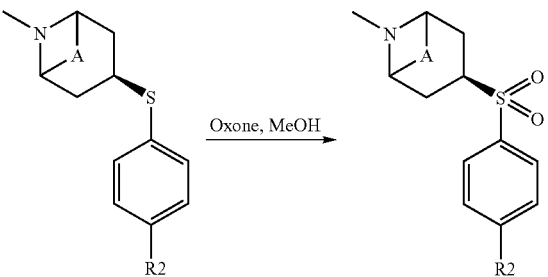

To a solution of the azabicylothiophenyl in methanol is added a solution of Oxone in water. The mixture is stirred at room temperature for about 30 minutes and then purified to yield the azabicylosulfonylphenyl.

The conversion of C=O moieties to C=S may be achieved by reaction with Lawesson's reagent [2,4-bis(4-methoxyphenyl)-1,3-dithia-2,4-diphosphetane-2,4-disulfide)] in a solvent such as toluene at refluxing temperature as shown in Scheme 21.

Reaction Scheme 21

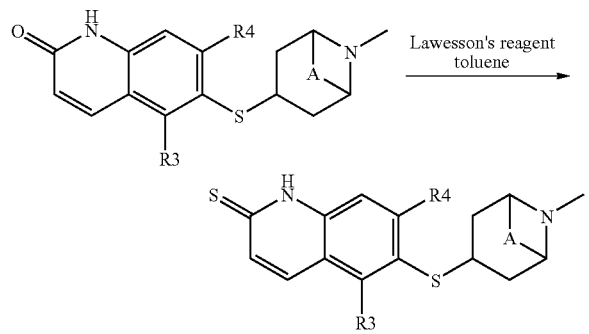

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al, "Prodrugs", *Drug Delivery Systems,* 1985, pp. 112–176, and *Drugs,* 1985, 29, pp. 455–473.

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

Another aspect of the present invention is a pharmaceutical composition comprising a compound of formula (I) substantially as described hereinbefore with a pharmaceutically acceptable diluent or carrier.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Compounds of the invention have been demonstrated to be active at the neuronal nicotinic, beta 4 receptor. Their functional agonist activity has been demonstrated in the test described below.

Functional Ca-Flux Assay

HEK 293 cell lines expressing different nicotinic receptor β4 subtypes are plated at a density of 50,000 cells/well into poly-D-lysine coated 96 well microtitre plates. Twenty-four hours later the cells are washed with buffer and loaded with Fluo-3 dye (10 M) at room temperature for 1 h. The dye is removed and 180 μl of buffer containing atropine at 3 μM added.

The plates are loaded into a FLIPR (Molecular Devices) and 20 μl of experimental compound are added in a concentration gradient across the plate. The stimulation of the nicotinic receptor response to compound addition is measured as a rise in fluorescence which correlates to the entry of calcium into the cell. Acetylcholine is added 10 min later to all wells to investigate whether the compounds can block the acetylcholine stimulated nicotine response.

The effects of compounds as nicotinic agonists and antagonists are calculated using an OMM (Oxford matrix management) curve fit package.

The present invention further provides compounds of formula (I) or compositions as hereinabove described for use in therapy.

The present invention further provides the use of a compound as hereinbefore described for the manufacture of a medicament for the treatment of a condition indicating treatment with a beta 4 subtype selective nicotinic acetylcholine receptor modulator.

The present invention further provides a method of treatment of a condition indicating treatment with a beta 4 subtype selective nicotinic acetylcholine receptor modulator comprising administering an effective amount of a compound or a composition as hereinbefore described to a patient in need thereof.

The present invention further provides the use of compounds of formula (I) in the manufacture of a medicament for the treatment of dysfunctions of the central and autonomic nervous systems. Such dysfunctions included, for example, dementia, cognitive disorders, neurodegenerative disorders, extrapyramidal disorders, convulsive disorders, cardiovascular disorders, endocrine disorders, eating disorders, affective disorders, and drug abuse.

The present invention further provides a method of treatment of dysfunctions of the central and autonomic nervous systems comprising administering an effective amount of a compound of formula (I) or a composition as hereinabove described to a patient in need thereof.

The present invention is now further illustrated by means of the following Examples.

EXAMPLE 1 a) Exo-3-(3-methoxyphenylthio)-8-methyl-8-azabicyclo[3.2.1]octane

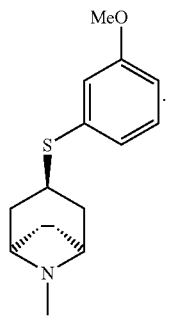

NaH (60% dispersion in mineral oil, 101 mg, 2.55 mmol) was washed with petroleum ether 40–60 (2×20 ml) under a flow of nitrogen, then treated with THF (~40 ml) generating a grey cloudy mixture. This mixture was treated with 3-methoxybenzenethiol (0.30 ml, 2.32 mmol), causing the evolution of gas and the reaction to become clear. After ten minutes the reaction was treated with 8-methyl-8-azabicyclo[3.2.1]oct-3-yl methanesulphonate (500 mg, 2.32 mmol) as a solution in THF (3×15 ml). The reaction was stirred at reflux under a flow of nitrogen overnight then concentrated in vacuo to a white sticky solid. This solid was dissolved in a mixture of $H_2O$ (40 ml) and $CHCl_3$ (40 ml) then acidified using 2N $HCl_{(aq)}$ to pH=2. The organic layer was removed and the aqueous washed with more $CHCl_3$ (2×40 ml). The aqueous layer was basified using 2N NaOH (pH ~10) then extracted using $CHCl_3$ (45 ml) and ethyl acetate (40 ml). The organic extractions were combined, dried ($MgSO_4$) and concentrated in vacuo to yield the title compound as a clear colourless oil (250 mg, 41%).

$\delta_H$ (300MHz; $CDCl_3$) 1.53–1.60 (2H, m, $CH_2$), 1.77–1.82 (4H, m, 2×$CH_2$), 1.99–2.04 (2H, m, $CH_2$), 2.27 (3H, s, $NCH_3$), 3.15–3.17 (2H, m, 2×$NCHCH_2$), 3.28–3.36 (1H, m, HCS), 3.78 (3H, s, Ar—$OCH_3$), 6.74–6.77 (1H, m, Ar—H), 6.93–6.98 (2H, m, 2×Ar—H) and 7.16–7.21 (1H, m, Ar—H); LCMS retention time ~2.62 min, m/z (FIAPOSES) 264.1 [(M+H)$^+$, 100%].

By proceeding in a similar manner to Example 1(a) but using the appropriate mercaptobenzene derivative, there were prepared the following compounds:

b) Exo-3-(4-methoxyphenylthio)-8-methyl-8-azabicyclo[3.2.1]octane $\delta_H$ (300 MHz; $CDCl_3$) 1.50 (2H, m, $CH_2$), 1.65–1.75 (4H, m, 2×$CH_2$), 1.98 (2H, m, $CH_2$), 2.22 (3H, s, $NCH_3$), 3.05 (1H, m, HCS), 3.18 (2H, m, 2×$NCHCH_2$), 3.78 (3H, s, Ar—$OCH_3$), 6.78 (2H, m, Ar—H); 7.38 (2H, m, Ar—H); m/z (FIAPOSES) 264.1 [(M+H)$^+$, 100%].

c) Exo-3-(2-chlorophenylthio)-8-methyl-8-azabicyclo[3.2.1]octane $\delta_H$ (300 MHz; DMSO) 1.65 (2H, m, $CH_2$), 1.75–1.85 (4H, m, 2×$CH_2$), 1.95 (2H, m, $CH_2$), 2.30 (3H, s, $NCH_3$), 3.10 (2H, m, 2×$NCHCH_2$), 3.60 (1H, m, HCS), 7.22 (1H, m, Ar—H), 7.40 (1H, m, Ar—H), 7.50 (2H, m, Ar—H); m/z (FIAPOSES) 268 [(M+H)$^+$, 100%].

d) Exo-3-(phenylthio)-8-methyl-8-azabicyclo[3.2.1]octane $\delta_H$ (300 MHz; DMSO) 1.63 (2H, m, $CH_2$), 1.75–1.85 (4H, m, 2×$CH_2$), 2.00 (2H, m, $CH_2$), 2.30 (3H, s, $NCH_3$), 3.10 (2H, m, 2×$NCHCH_2$), 3.30 (1H, m, HCS), 7.22 (3H, m, Ar—H),), 7.38 (2H, m, Ar—H),); m/z (FIAPOSES) 234 [(M+H)$^+$, 100%].

EXAMPLE 2

Exo-3-(8-methyl-8-azabicyclo[3.2.1]oct-3-ylthio)-benzamide

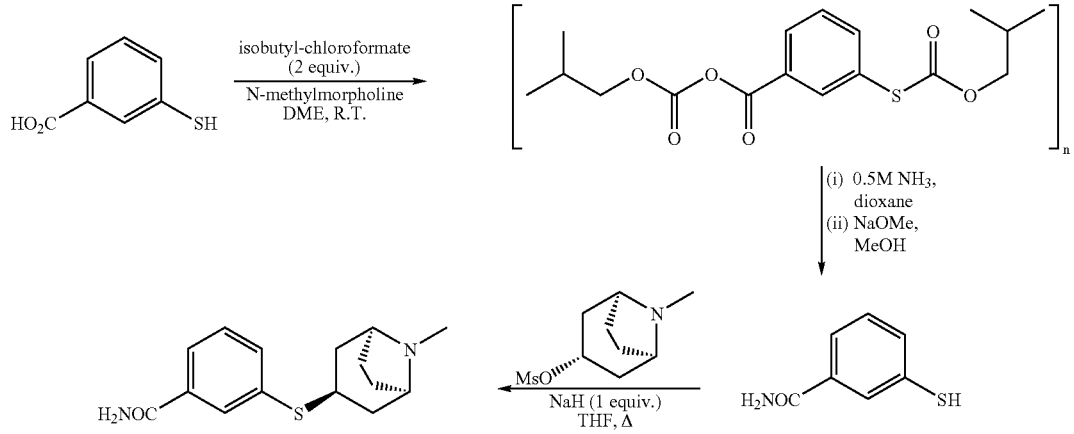

(i) 3-mercaptobenzamide

To a solution of 3-mercaptobenzoic acid (1.00 g, 6.49 mmol) in DME (ethyleneglycol-dimethylether, ~15 ml) was added N-methylmorpholine (1.5 ml, 13.6 mmol) and isobutylchloroformate (1.77 ml, 13.6 mmol) under a flow of nitrogen. The clear solution quickly became a cloudy mixture and the temperature started to rise. After stirring for half an hour the reaction was filtered and then treated with 0.5M $NH_3$ in dioxane (27 ml, 13.5 mmol). The reaction was treated with sodium methoxide in methanol, then quenched with 2N HCl until pH=4 and then concentrated in vacuo to a white paste. This was partitioned between $CHCl_3$ and $H_2O$ (3×100 ml) and the organic layer dried ($MgSO_4$) and concentrated in vacuo to a white solid (1.6 g). This was dissolved in $H_2O$, basified (2N NaOH, pH=10) and the aqueous washed with $CHCl_3$. The aqueous was acidified (2N HCl, pH=2) then extracted with $CHCl_3$ (2×50 ml). The organic extracts were dried ($MgSO_4$) then concentrated in vacuo to give 3-mercaptobenzamide as a white solid (501 mg).

(ii) Exo-3-(8-methyl-8-azabicyclo[3.2.1]oct-3-ylthio)-benzamide

NaH (60% dispersion in mineral oil, 154 mg, 3.84 mmol) was washed with petroleum ether 40–60 (3×20 ml) then treated with THF (60 ml) under a flow of nitrogen to give a white cloudy mixture. This mixture treated with 3-mercaptobenzamide (490 mg, ~3mmol) as a solution in THF (3×10 ml), then with 8-methyl-8-azabicyclo[3.2.1]oct-3-yl methanesulphonate (490 mg, 2.24 mmol) as a solution in THF (3×5 ml) then slowly warmed to reflux. The reaction was maintained at reflux under a flow of nitrogen for two days then concentrated in vacuo to a pale yellow solid. This was dissolved in $H_2O$ (50 ml), acidified (2N HCl, pH=2), washed with $CHCl_3$ (50 ml) and ethyl acetate (50 ml), basified (2N NaOH, pH=10) and extracted with $CHCl_3$ (50 ml) and ethyl acetate (50 ml). The organic extracts were combined, dried ($MgSO_4$) and concentrated in vacuo to yield the title compound as a colourless crystalline solid (240 mg, 39%), m.p. ~147° C.; $\delta_H$ (300 MHz; $CDCl_3$) 1.49–1.61 (2H, m, $CH_2$), 1.74–1.83 (4H, m, 2×$CH_2$), 2.00–2.05 (2H, m, $CH_2$), 2.27 (3H, s, $NCH_3$), 3.16–3.18 (2H, m, 2×$NCHCH_2$), 3.30–3.37 (1H, m, HCS), 5.96–6.24 (2H, m, $CONH_2$), 7.28–7.43 (2H, m, 2×Ar—H), 7.52–7.55 (1H, m, Ar—H), 7.64–7.66 (1H, m, Ar—H) and 7.84–7.85 (1H, m, Ar—H); LCMS retention time ~1.4 min, m/z (FIAPOSES) 277.1 [(M+H)$^+$, 100%].

EXAMPLE 3 a) Exo-3-(4-aminophenylthio)-8-methyl-8-azabicyclo[3.2.1]octane

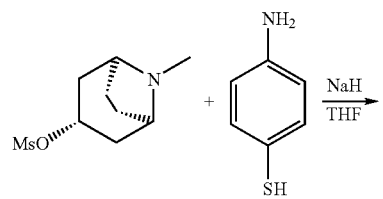

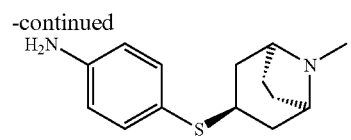

NaH (60% dispersion in mineral oil, 1.59 g, 39.8 mmol) was washed with petroleum ether 40–60 (2×40 ml) under a flow of nitrogen, then treated with THF (~120 ml) generating a grey cloudy mixture. This mixture was cooled to 0° C. then treated with 4-aminothiophenol (4.77 g, 38.2 mmol) as a solution in THF (4×15 ml), gas could be seen evolving throughout the addition. After ten minutes the reaction was treated with 8-methyl-8-azabicyclo[3.2.1]oct-3-yl methanesulphonate (6.87 g, 31.8 mmol) as a solution in THF (3×20 ml) then slowly warmed to reflux. The reaction was refluxed for 5 hours then stirred at room temperature for two days. The reaction was filtered then concentrated in vacuo to a brown oil (~9 g) which was added to acidified water (HCl, pH=1,250 ml) then washed with $CHCl_3$ (2×100 ml). The aqueous layer was basified using 2N NaOH (pH~13) then extracted using $CHCl_3$ (3×75 ml). The organic extractions were combined, dried ($MgSO_4$) and concentrated in vacuo to a yellow oil (~7 g). Flash chromatography ($SiO_2$ 100 g, gradient elution; $CHCl_3$: MeOH; 100:0 to 90:10) afforded one major fraction. Evaporation gave the title compound as a pale yellow crystalline solid (3.69 g, 47%); (m.p. 79–81° C.); $\delta_H$ (300 MHz; $CDCl_3$) 1.48–1.53 (2H, m, $CH_2$), 1.63–1.75 (4H, m, 2×$CH_2$), 1.94–1.98 (2H, m, $CH_2$), 2.24 (3H, s, $NCH_3$), 2.98–3.04 (1H, m, HCS), 3.11–3.13 (2H, m, 2×$NCHCH_2$), 3.74 (2H, br. s, Ar—$NH_2$), 6.58–6.61 (2H, m, 2×Ar—H) and 7.23–7.26 (2H, m, 2×Ar—H); LCMS retention time ~1.57 min, m/z (FIAPOSES) 249.1 [(M+H)$^+$, 60%] and 125.2 (100%).

b) Exo-3-(3-aminophenylthio)-8-methyl-8-azabicyclo[3.2.1]octane

By proceeding in a similar manner to Example 3(a) but using 3-aminothiophenol, there was prepared the title compound as a yellow solid. $\delta_H$ (300 MHz; $CDCl_3$) 1.50 (2H, m, $CH_2$), 1.75–1.85 (4H, m, 2×$CH_2$), 2.20 (2H, m, $CH_2$), 2.25 (3H, s, $NCH_3$), 3.10 (2H, m, 2×$NCHCH_2$), 3.25 (1H, m, HCS), 3.60 (2H, br. s, Ar—$NH_2$), 6.50 (1H, m, Ar—H),), 6.70 (1H, m, Ar—H),), 6.77 (1H, m, Ar—H),), 7.05 (1H, m, Ar—H); m/z (FIAPOSES) 249.1 [(M+H)$^+$, 100%].

EXAMPLE 4 a) Exo-3-(4-methanesulphonylaminophenylthio)-8-methyl-8-azabicyclo[3.2.1]octane

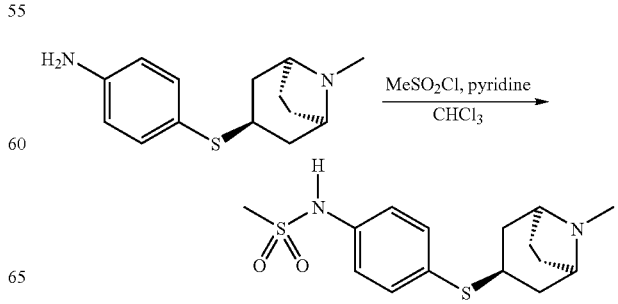

To a solution of Exo-3-(4-aminophenylthio)-8-methyl-8-azabicyclo[3.2.1]octane (Example 3(a), 250 mg, 1.01 mmol) in CHCl$_3$ (~75 ml) was added pyridine (79 mg, 1.01 mmol) followed by methanesulphonyl chloride (115 mg, 1.01 mmol) both as solutions in CHCl$_3$ (2×1 ml). The pale yellow solution was stirred at room temperature under a flow of nitrogen for two days. Once LCMS showed no more starting material the reaction was quenched with 35% NH$_4$OH$_{(aq)}$ (~25 ml) then extracted with more CHCl$_3$ (25 ml). The two organic extracts were combined and washed with NH$_4$OH$_{(aq)}$ then dried (MgSO$_4$) and concentrated in vacuo to a yellow oil. Excess pyridine which was removed under vacuum, the remaining oil was purified using preparative LCMS, yielding the title compound as a thick sticky paste (117 mg, 36%); $\delta_H$ (300 MHz; CDCl$_3$) 1.88–1.93 (4H, m, 2×CH$_2$), 2.22–2.30 (4H, m, 2×CH$_2$), 2.60 (3H, s, $^+$NCH$_3$), 3.00 (3H, s, SO$_2$CH$_3$), 3.11–3.18 (1H, m, HCS), 3.76 (2H, br. s, 2×$^+$NCHCH$_2$), 4.5–5.5 (1H, br. s, Ar—NH), 7.20–7.23 (2H, m, 2×Ar—H), 7.40–7.43 (2H, m, 2×Ar—H) and 8.40 (1H, s, HCO$_2^-$); LCMS retention time ~2.02 min, m/z (FIAPOSES) 327.1 [(M+H)$^+$, 100%].

b) Exo-3-(4-acetylaminophenylthio)-8-methyl-8-azabicyclol3.2.1]octane

By proceeding in a manner similar to example 4(a) but using acetic anhydride in place of methanesulphonyl chloride there was prepared the title compound as a pale yellow solid. $\delta_H$ (300 MHz; CDCl$_3$) 1.90–2.00 (4H, m, 2×CH$_2$), 2.05–2.20 (4H, m, 2×CH$_2$), 2.50 (3H, s, COCH$_3$), 2.60 (3H, s, NCH$_3$), 3.50 (1H, m, HCS), 3.75 (2H, br. s, 2×NCHCH$_2$), 7.40 (2H, m, 2×Ar—H), 7.65 (2H, m, 2×Ar—H); m/z (FIAPOSES) 291 [(M+H)$^+$, 100%].

c) Exo-3-(3-acetylaminophenylthio)-8-methyl-8-azabicyclo[3.2.1]octane

By proceeding in a manner similar to example 4(a) but using acetic anhydride in place of methanesulphonyl chloride and exo-3-(3-aminophenylthio)-8-methyl-8-azabicyclo [3.2.1]octane [Example 3(b)] there was prepared the title compound as a pale yellow solid. $\delta_H$ (300 MHz; CDCl$_3$) 1.90–2.10 (4H, m, 2×CH$_2$), 2.15–2.20 (4H, m, 2×CH$_2$), 2.60 (3H, s, COCH$_3$), 2.65 (3H, s, NCH$_3$), 3.38 (2H, br. s, 2×NCHCH$_2$), 3.60 (1H, m, HCS), 7.10 (1H, m, Ar—H),), 7.23 (1H, m, Ar—H),), 7.42 (1H, m, Ar—H),), 7.81 (1H, m, Ar—H); m/z (FIAPOSES) 291 [(M+H)$^+$, 100%].

EXAMPLE 5

Exo4-(8-methyl-8-azabicyclo[3.2.1]oct-3-ylthio)-benzamide

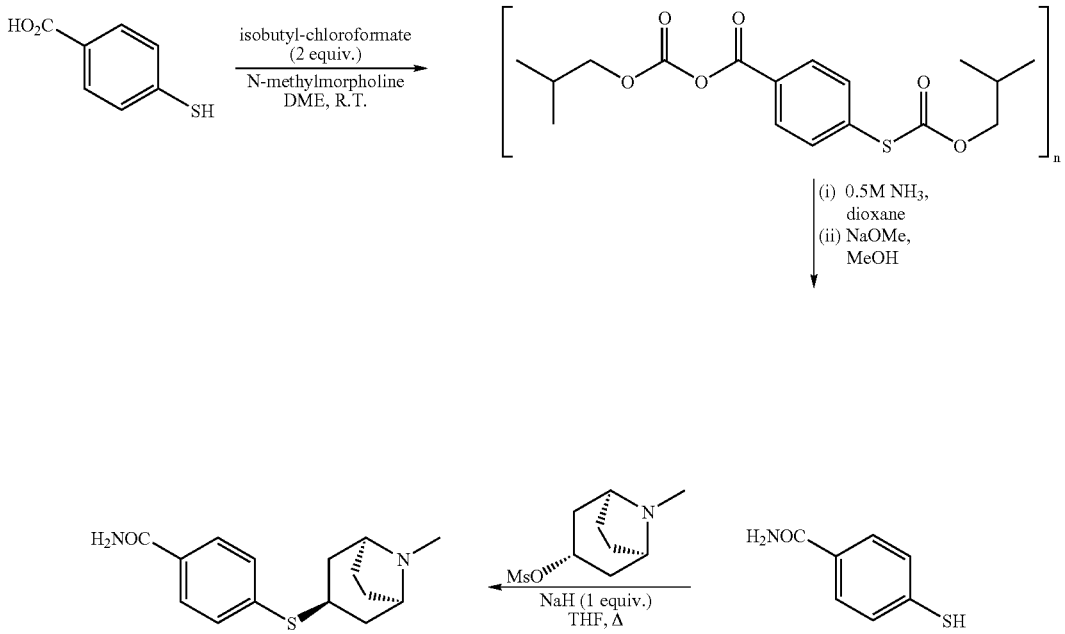

(i) 4-mercaptobenzamide

To a stirred solution of 4-mercaptobenzoic acid (1.00 g, 6.49 mmol) and N-methylmorpholine (0.78 ml, 7.14 mmol) in ethyleneglycol dimethylether (20 ml) was added isobutylchloroformate (0.92 ml, 7.14 mmol). The reaction was stirred at ambient temperature overnight and filtered to a clear pale yellow solution which was treated with excess ammonia as a solution in dioxane (0.5M, ~15 ml). This solution was stirred for two hours at room temperature, and concentrated in vacuo to a white solid. The solid was dissolved in a mixture of $H_2O$ (10 ml) and $CHCl_3$ (30 ml), the aqueous was basified using 2N $NaOH_{(aq)}$ and the organic layer separated and dried ($MgSO_4$) before being concentrated in vacuo to a white solid (679 mg). The solid was treated with a solution of sodium methoxide in methanol (10 ml) and when TLC showed no more starting material, the reaction was acidified using 2N $HCl_{(aq)}$ to pH=4, then concentrated in vacuo. The residue was treated with water and extracted with $CHCl_3$, then concentrated in vacuo to give the title compound as an off white solid (376 mg).

(ii) Exo-4-(8-methyl-8-azabicyclo[3.2.1]oct-3-ylthio)-benzamide

NaH (60% dispersion in mineral oil, 96 mg, 2.40 mmol) was washed with petroleum ether 40–60 (3×20 ml) under a flow of nitrogen, then treated with THF (~40 ml) generating a grey cloudy mixture. This mixture treated with a solution of 4-mercaptobenzamide (~376 mg, ~2 mmol) in THF (3×10 ml) then 8-methyl-8-azabicyclo[3.2.1]oct-3-yl methanesulphonate (432 mg, 2.0 mmol) as a solution in THF (3×5 ml). The reaction was stirred at reflux under a flow of nitrogen overnight then concentrated in vacuo to a fine yellow solid. The solid was treated with a mixture of $H_2O$ (20 ml) and $CHCl_3$ (20 ml) then acidified using 2N $HCl_{(aq)}$ to pH=2. The organic layer was removed and the aqueous washed with ethyl acetate (20 ml). The aqueous layer was basified using 2N NaOH (pH ~10) then extracted using $CHCl_3$ (20 ml) and ethyl acetate (20 ml). The combined organic extractions were dried ($MgSO_4$) and concentrated in vacuo to an orange oil (392 mg). The oil was purified by preparative LCMS, yielding the title compound as a colourless oil (148 mg); $\delta_H$ (300 MHz; $CDCl_3$) 1.85–1.97 (4H, m, 2×$CH_2$), 2.15–2.59 (4H, m, 2×$CH_2$), 2.59 (3H, s, $^+NCH_3$), 3.33–3.45 (1H, m, HCS), 3.66 (2H, br. s, 2×$^+NCHCH_2$), 7.43–7.46 (2H, m, 2×Ar—H), 7.74–7.76 (2H, m, 2×Ar—H) and 8.39 (1H, s, $HCO_2^-$); LCMS retention time ~1.55 min, m/z (FIAPOSES) 277.1 [(M+H)$^+$, 100%].

EXAMPLE 6

Exo-N-methyl 4-(8-methyl-8-azabicyclo[3.2.1]oct-3-ylthio)-benzamide

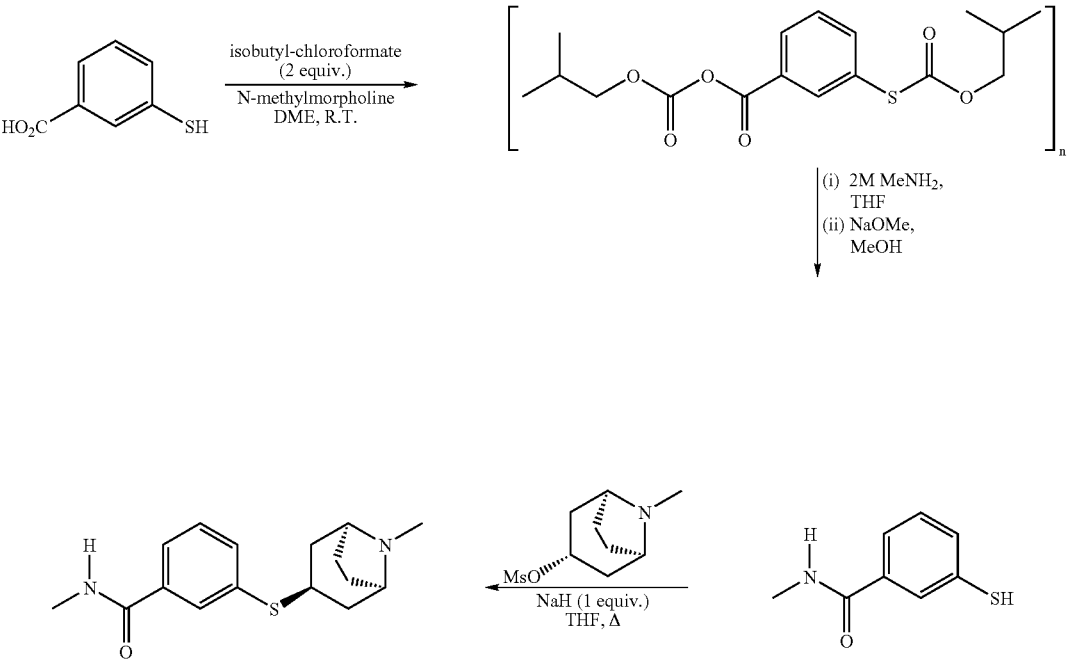

(i) N-Methyl 3-mercaptobenzamide

To a solution of 3-mercaptobenzoic acid (1.00 g, 6.49 mmol) in ethyleneglycol-dimethylether (10 ml) was added N-methylmorpholine (1.5 ml, 13.6 mmol) and iso-butylchloroformate (1.77 ml, 13.6 mmol) under a flow of nitrogen at 0° C. The clear solution quickly became a thick paste. After stirring for one hour the reaction was filtered and then treated with 2M methylamine in THF (7 ml, 14 mmol). The reaction was stirred for two days at room temperature and then treated with 0.5M sodium methoxide in methanol (14 ml). The reaction was stirred for three hours, then quenched with 2N HCl until pH=4 and concentrated in vacuo to a semi solid. This was dissolved in $H_2O$ (50 ml), basified (2N NaOH, pH=10), washed with $CHCl_3$ (2×50 ml), acidified (2N HCl, pH=2) then extracted with $CHCl_3$ (50 ml) and ethyl acetate (50 ml). The organic extracts were combined, dried ($MgSO_4$) then concentrated in vacuo to a colourless oil (570 mg).

(ii) Exo-N-methyl4-(8-methyl-8-azabicyclo[3.2.1] oct-3-ylthio)-benzamide

NaH (60% dispersion in mineral oil, 179 mg, 4.48 mmol) was washed with petroleum ether 40–60 (2×20 ml) then treated with THF (40 ml) under a flow of nitrogen to give a white cloudy mixture. This mixture treated with N-methyl 3-mercaptobenzamide(570 mg, ~3.7 mmol) as a solution in THF (2×10 ml), then with 8-methyl-8-azabicyclo[3.2.1]oct-3-yl methanesulphonate (572 mg, 2.61 mmol) as a solution in THF (3×5 ml). The reaction was heated at reflux under a flow of nitrogen overnight then concentrated in vacuo to a pale yellow solid. This was dissolved in $H_2O$ (50 ml), acidified (2N HCl, pH=2) and washed with $CHCl_3$ (50 ml) and ethyl acetate (50 ml). The aqueous was basified (2N NaOH, pH=10) and extracted with $CHCl_3$ (50 ml) and ethyl acetate (50 ml). The organic extracts were combined, dried ($MgSO_4$) and concentrated in vacuo to a pale yellow oil (402 mg). Purification by preparative LCMS yielded the title compound as a colourless crystalline solid (300 mg, 40%); m.p. ~87–89° C.; $\delta_H$ (300 MHz; $CDCl_3$) 1.82–1.99 (4H, m, 2×$CH_2$), 2.17–2.36 (4H, m, 2×$CH_2$), 2.60 (3H, s, $^+NCH_3$), 2.99–3.01 (3H, d, J=4.5 Hz, $CONCH_3$), 3.20–3.32 (1H, m, HCS), 3.68 (2H, br. s, 2×$NCHCH_2$), 7.33–7.38 (1H, m, Ar—H), 7.49–7.52 (1H, m, Ar—H), 7.70–7.73 (1H, m, Ar—H), 7.79–7.80 (1H, m, Ar—H) and 8.70 (1H, s, $HCO_2^-$); LCMS retention time ~2.0 min, m/z (FIAPOSES) 291.1 [(M+H)+, 100%].

EXAMPLE 7

Exo-3-(8-methyl-8-azabicyclo[3.2.1]oct-3-ylthio)-benzoic acid

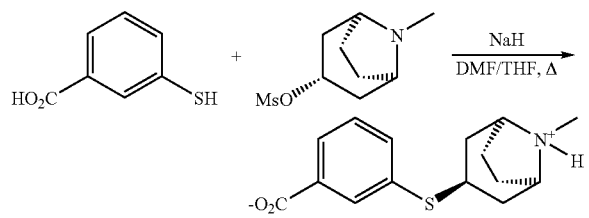

NaH (60% dispersion in mineral oil, 2.18 g, 54.5 mmol) treated with THF (~210 ml) and DMF (70 ml), under a flow of nitrogen to give a white cloudy mixture. This mixture treated with 3-mercapto-benzoic acid (4.00 g, 25.9 mmol) as a solution in THF (6×5 ml) dropwise over 20 minutes, gas could be seen evolving throughout the addition. Large amounts of a sticky solid began to form in the solution so more DMF (70 ml) was added to help solvation. After 30 minutes the reaction was treated with 8-methyl-8-azabicyclo [3.2.1]oct-3-yl methanesulphonate (5.6 g, 25.9 mmol) as a solution in THF (2×10 ml) then slowly warmed to reflux for 4 hours. The reaction was stirred at room temperature overnight to give a yellow cloudy mixture which was concentrated in vacuo to a thick yellow oil, which could be purified by recrystallising from 10:1 $H_2O$:$CH_3CN$ to yield the title compound as a crystalline solid (1.65 g, 23%); (m.p. 249–251° C.); $\delta_H$ (300 MHz; $D_2O$) 1.81–2.21 (8H, m, 4×$CH_2$), 2.64 (3H, s, $^+NCH_3$), 3.41–3.54 (1H, m, HCS), 3.80 (2H br. s, 2×$^+NCHCH_2$), 7.32–7.41 (1H, m, Ar—H), 7.47–7.54 (1H, m, Ar—H), 7.74–7.76 (1H, m, Ar—H) and 7.87 (1H, br. s, Ar—H); $\delta_H$ (300 MHz; methanol d4) 2.01–2.18 (6H, m, 3×$CH_2$), 2.29–2.32 (2H, m, $CH_2$), 2.75 (3H, s, $^+NCH_3$), 3.57–3.60 (1H, m, HCS), 3.88 (2H br. s, 2×$^+NCHCH_2$), 7.35–7.54 (1H, m, Ar—H), 7.55–7.57 (1H, m, Ar—H), 7.86–7.89 (1H, m, Ar—H) and 8.04–8.05 (1H, m, Ar—H); LCMS retention time ~1.9 min, m/z (FIAPOSES) 278.1 [(M+H)+, 100%].

EXAMPLE 8

Exo-3-(8-methyl-8-azabicyclo[3.2.1]oct-3-ylthio)-benzyl alcohol

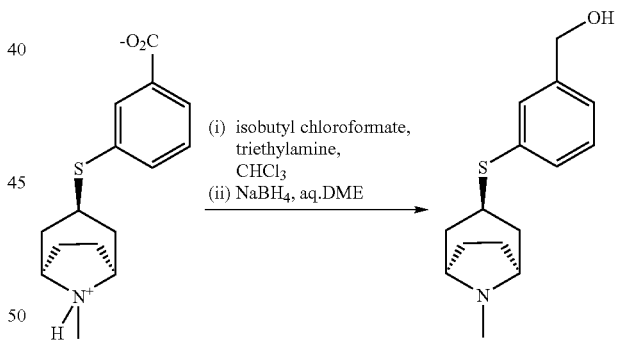

A solution of exo-3-(8-methyl-8-azabicyclo[3.2.1]oct-3-ylthio)-benzoic acid (Example 7, 230 mg) in chloroform (50 ml) was treated with triethylamine (90 mg) and isobutyl chloroformate (119 mg). After stirring at ambient temperature for 2 hours, the reaction mixture was concentrated in vacuo. The residue was dissolved in ethylene glycol dimethyl ether (40 ml) and treated dropwise with a solution of sodium borohydride (34 mg) in water (2 ml) over 30 minutes. After stirring a further 1 hour at ambient temperature, the reaction mixture was partitioned between ethyl acetate (30 ml) and water (10 ml). The organic layer was dried over magnesium sulphate and and concentrated to dryness. The residue was purified by preparative HPLC to give the title compound (60 mg) as a white solid.

EXAMPLE 9

3-Bromo4-(8-methyl-8-aza-bicyclo[3.2.1]oct-3(exo)-ylsulfanyl)-phenol

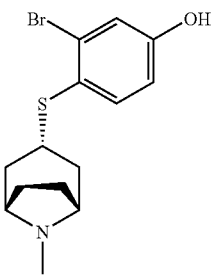

(i) 3-Bromo-4-thiocyanato-phenol

To an ice-cooled suspension of Pb(SCN)$_2$ (1.81 g, 5.6 mmol) in dry methylene chloride (27 mL) PhICl$_2$ (0.97 g, 3.54 mmol, (prepared according to D. Koyuncu et al., *J. Chem. Res. (S)* 1990, 21) was added and the resulting mixture was stirred for 30 min at 0° C. under nitrogen. A solution of 3-bromophenol (250 mg, 1.44 mmol) in dry methylene chloride (3 mL) was added, the mixture was stirred for 2 h at 0° C. and filtered in cold through a celite® pad washing extensively with ethyl acetate. After addition of silicagel to the filtrate and evaporation of solvents, the mixture was purified by flash chromatography (30% ethyl acetate/hexanes) to afford 0.32 g (47%) of the title compound as a brown solid. m.p. 91–92° C.

(ii) 3-Bromo4-mercaptophenol

To a hot (85° C.) solution of 3-bromo-4-thiocyanato-phenol (315 mg, 1.37 mmol) in absolute ethanol (10 mL) under nitrogen, sodium sulfide nonahydrate (403 mg, 2.05 mmol) was added. The resulting mixture was stirred at 85° C. for 20 min. More sodium sulfide nonahydrate (230 mg) was added and heating was continued for 15 min. The mixture was cooled down, made acidic with 5N acetic acid (10 mL) and extracted with methylene chloride (×1). The organic layer was washed once with water, dried and concentrated in vacuo to give the title compound as a yellow solid (259 mg, 92%) which was quickly submitted to the next reaction without further treatment. EIMS M−1: 203.

(iii) 3-Bromo-4-(8-methyl-8-aza-bicyclo[3.2.1]oct-3(exo)-ylsulfanyl)-phenol To a solution of 3-bromo-4-mercaptophenol (259 mg, 1.3 mmol) and methanesulfonic acid 8-methyl-8-aza-bicyclo[3.2.1]oct-3-yl ester (240 mg, 1.1 mmol) in dry dimethylformamide (10 mL) under nitrogen, potassium carbonate (407 mg, 2.75 mmol) was added. The resulting mixture was vigorously stirred at room temperature for 18 h under nitrogen and 10% hydrochloric acid was added. The mixture was washed with ethyl acetate (×3), the aqueous layer made basic (pH=8) with solid sodium bicarbonate and extracted with ethyl acetate (×4). The combined organic phase was concentrated in vacuo and purified by flash chromatography (10% Methanol/1% ammonia/methylene chloride) to give the title compound, 170 mg (47%).

EIMS M+1: 328. $^1$H NMR (200 MHz, CD$_3$OD) δ7.37 (d, J=8.6 Hz, 1 H), 7.07 (d, J=2.7 Hz, 1 H), 6.69 (dd, J=8.4, 2.7 Hz, 1 H), 3.19 (br m, 3 H), 2.25 (s, 3H), 2.05 (m, 2 H), 1.77–1.71 (m, 4 H), 1.60 (d, J=8.0 Hz, 2H). $^{13}$C NMR (300 MHz, CD$_3$OD) δ 160.9, 139.0, 131.9, 124.4, 122.0, 116.9, 63.3, 40.2, 39.8, 39.2, 27.1.

EXAMPLE 10

5-Hydroxy-2-(8-methyl-8-aza-bicyclo[3.2.1]oct-3-ylsulfanyl)-benzonitrile

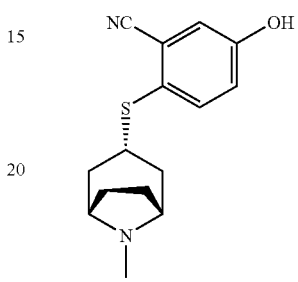

3-Bromo4-(8-methyl-8-aza-bicyclo[3.2.1]oct-3(exo)-ylsulfanyl)-phenol (35 mg, 0.1 mmol), zinc cyanide (23 mg, 0.2 mmol) and DPPF (28 mg, 0.05 mmol) were dissolved in degassed and dry DMF (0.2 mL). To the above mixture, Pd$_2$(dba)$_3$ (18 mg, 0.02 mmol) was added and the resulting mixture was stirred at 120° C. for 6 h, cooled down, diluted with ethyl acetate and filtered through a celite® pad. The filtrate was washed once with a saturated sodium bicarbonate solution and extracted with 10% hydrochloric acid (×2). The aqueous phase was concentrated in vacuo and purified by SCX to afford 5.5 mg (20%) of the title compound.

EIMS M+1: 275. $^1$H NMR (200 MHz, CD$_3$OD) δ 7.45 (d, J=8.3 Hz, 1 H), 7.05 (d, J=2.7 Hz, 1 H), 6.96 (dd, J=8.6, 2.7 Hz, 1 H), 3.30 (br m, 3 H), 2.30 (s, 3H), 2.08 (m, 2 H), 1.83–1.78 (m, 4H), 1.67 (d, J=8.3 Hz, 2H). $^{13}$C NMR (300 MHz, CD$_3$OD) δ 160.8, 138.4, 124.0, 121.6, 120.9, 119.7, 117.9, 62.1, 39.5, 38.6, 37.6, 25.6.

EXAMPLE 11

4-(8-methyl-8-aza-bicyclo[3.2.1]oct-6-en-3(exo)-ylsulfanyl)-phenol

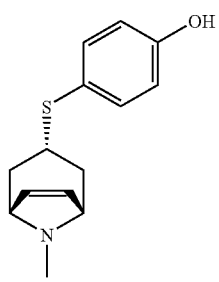

(i) Methanesulfonic acid 8-methyl-8-aza-bicyclo[3.2.1]oct-6-en-3(endo)-yl ester To a solution of 8-methyl-8-aza-bicyclo[3.2.1]oct-6-en-3-ol hydrochloride (from E-Merck, 3.0 g, 17.08 mmol) in CH$_2$Cl$_2$ (30 mL) pyridine (2.7 mL, 2.64 g, 34.16 mmol) and methanesulfonyl chloride (1.6 mL, 2.37 g, 20.50 mmol) were added and the mixture was stirred at 23° C. for 72 h. Then the reaction was diluted with CH$_2$Cl$_2$ and washed successively with aq NH$_4$OH 32% and brine. The combined aqueous phase was extracted with CH$_2$Cl$_2$ and the organic phase was dried and concentrated in vacuo to afford the mesylate as a pale yellow solid (2.2 g, 59%) that was used without further purification. m. p. 64–65° C.

$^1$H NMR (200 MHz, CDCl$_3$) δ 6.02 (br s, 2 H), 4.88 (t, J=5.8 Hz, 1 H), 3.39 (br s, 2 H), 2.9 (s, 3 H), 2.36–2.26 (m, 2 H), 2.26 (s, 3 H), 1.98–1.90 (m, 2 H).

(ii) 4-(8-methyl-8-aza-bicyclo[3.2.1]oct-6-en-3 (exo)-ylsulfanyl)-phenol

To a mixture of the compound from step A (500 mg, 2.3 mmol) and 4-mercaptophenol (380 mg, 3.0 mnmol) in dry DMF (15 mL), potassium carbonate (920 mg, 6.22 mmol) was added. The resulting mixture was vigorously stirred at room temperature for 16 h. The mixture was diluted with ethyl acetate and extracted with 10% hydrochloric acid (x2). The combined aqueous phase was neutralised with sodium carbonate, extracted with ethyl acetate (×6), dried (Na$_2$SO$_4$) and evaporated. The crude was purified by flash chromatography (5% Methanol/1% ammonia/methylene chloride) to give the title compound, 120 mg (21%) as a white solid.

EIMS M+1: 248. $^1$H NMR (200 MHz, CD$_3$OD) δ 7.23 (d, J=8.6 Hz, 2 H), 6.70 (d, J=8.6 Hz, 2 H), 5.89 (s, 2 H), 3.47 (br s, 2 H), 2.93 (m, 1 H), 2.15 (s, 3 H), 1.73 (d, J=3.0 Hz, 2 H), 1.68 (t, J=2.9 Hz, 2 H). $^{13}$CNMR (300 MHz, CD$_3$OD) δ 159.9, 138.2, 131.0, 124.6, 117.7, 69.1, 41.6, 41.5, 34.5.

EXAMPLE 12

4-(8-methyl-8-aza-bicyclo[3.2.1]oct-6-en-3(endo)-ylsulfanyl)-phenol

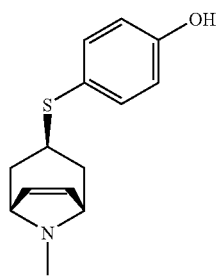

To a mixture of methanesulfonic acid 8-methyl-8-aza-bicyclo[3.2.1]oct-6-en-3(endo)-yl ester (326 mg, 1.5 mmol) and 4-mercaptophenol (210 mg, 1.65 mmol) in acetone (10 mL), K$_2$CO$_3$ (1.33 g, 9.0 mmol) was added. The resulting mixture was stirred at 65° C. for 16 h. The mixture was diluted with brine and extracted with CH$_2$Cl$_2$ (×5), dried (Na$_2$SO$_4$) and evaporated. The crude was purified by flash chromatography (8% Methanol/1% ammonia/methylene chloride) to give the title compound, 57 mg (15%) as a white solid.

EIMS M+1: 248. $^1$H NMR (200 MHz, CD$_3$OD) δ 7.16 (d, J=8.6 Hz, 2 H), 6.69 (d, J=8.8 Hz, 2 H), 6.05 (s, 2 H), 3.48 (br s, 2 H), 3.10 (t, J=7.2 Hz, 1 H), 2.36 (dd, J=7.3, 3.5 Hz, 1 H), 2.29 (dd, J=7.4, 3.5 Hz, 1 H), 2.26 (s, 3 H), 1.91 (d, J=14.2Hz, 2H). $^{13}$C NMR (300 MHz, CD$_3$OD) δ 159.3, 136.0, 133.9, 130.1, 117.8, 68.4, 44.1, 42.1, 36.4.

EXAMPLE 13

3-Chloro-4-(8-methyl-8-aza-bicyclo[3.2.1]oct6-en-3 (exo)-ylsulfanyl)-phenol, trifluoroacetate salt

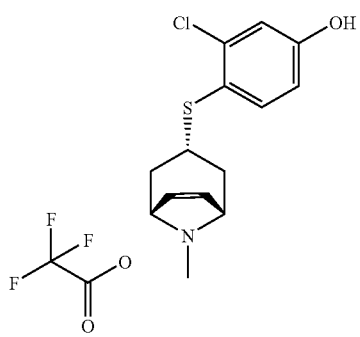

To a mixture of methanesulfonic acid 8-methyl-8-aza-bicyclo[3.2.1]oct-6-en-3 (endo)-yl ester (366 mg, 1.69 mmol) and 3-chloro-4-mercaptophenol (379 mg, 2.36 mmol) in dry DMF (11 mL), K$_2$CO$_3$ (675 mg, 4.6 mmol) was added. The resulting mixture was stirred at room temperature for 16 h. The mixture was diluted with ethyl acetate and extracted with 10% hydrochloric acid (×2). The combined aqueous phase was neutralised with sodium carbonate, extracted with ethyl acetate (×6), dried (Na$_2$SO$_4$) and evaporated. The crude was purified by flash chromatography (5% Methanol/1% ammonia/methylene chloride) and reverse phase HPLC to give the title compound as a white solid.

EIMS M+1: 282. $^1$H NMR (200 MHz, CDCl$_3$) δ 7.42 (d, J=8.6 Hz, 1 H), 6.92 (dd, J=2.4 Hz, 1H), 6.72 (dd, J=8.6, 2.4 Hz, 1 H), 6.13 (d, J=0.8 Hz, 2 H), 4.31 (br s, 2 H), 3.28 (m, 1 H), 2.77 (s, 3 H), 2.17–1.91 (m, 4 H).

$^{13}$C NMR (300 MHz, CDCl$_3$) δ 160.8, 141.0, 139.6, 128.3, 121.0, 118.2, 116.0, 69.9, 39.2, 38.1, 31.9.

EXAMPLE 14

2-Methyl-4-(8-methyl-8-aza-bicyclo[3.2.1]oct-3 (exo)-ylsulfanyl)-phenol, trifluoroacetate salt

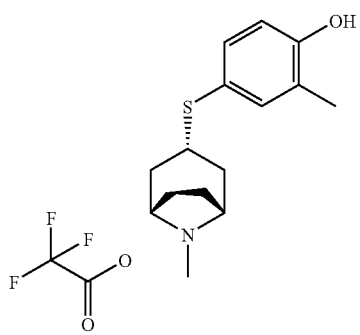

(i) 2-Methyl-4-thiocyanato-phenol

To an ice-cooled suspension of Pb(SCN)$_2$ (485 mg, 1.5 mmol) in dry methylene chloride (10 mL), PhICl$_2$ (330 mg, 1.2 mmol) was added and the resulting mixture was stirred for 25 min at 0° C. under nitrogen. A solution of o-cresol (108 mg, 1 mmol) in dry methylene chloride (2 mL) was added dropwise. The mixture was stirred for 1 h at 0° C. and filtered through a celite® pad washing extensively with methylene chloride. After addition of silicagel to the filtrate and evaporation of solvents, the mixture was purified by flash chromatography (10% ethyl acetate/hexane) to afford 164 mg (99%) of the title compound as a white solid.

m.p. 64–68° C. EIMS M+1: 166. IR (cm$^{-1}$): 3406, 1637, 1495, 1276, 1180, 814. $^1$H NMR δ (ppm) (200 MHz, CDCl$_3$): 7.31 (d, J=2.4 Hz, 1 H), 7.23 (dd, J=8.6 Hz, 2.4 Hz, 1 H), 6.79 (d, J=8.6 Hz, 1 H), 2.21 (s, 3 H). $^{13}$C NMR δ (ppm) (200 MHz, CDCl$_3$): 155.6 (C), 134.1 (CH), 130.5 (CH), 126.3 (C), 115.7 (CH), 111.9 (C), 111.0 (C), 14.8 (CH$_3$).

(ii) 2-Methyl4-(8-methyl-8-aza-bicyclo[3.2.1]oct-3 (exo)-ylsulfanyl)-phenol, trifluoroacetate salt To a solution of 2-methyl4-thiocyanato-phenol (160 mg, 0.97 mmol) in absolute ethanol (8 mL) under nitrogen, sodium sulfide nonahydrate (298 mg, 1.1 6 mmol) was added. The resulting mixture was stirred at 85° C. for 30 min and a solution of methanesulfonic acid 8-methyl-8-aza-bicyclo[3.2.1]oct-3-yl ester (254 mg, 1.16 mmol) in absolute ethanol (4 mL) was added dropwise at 85° C. The mixture was stirred for 2 h. The solvent was removed in vacuo and residue was submitted to a SCX collecting a mixture exo/endo. This mixture was purified by reverse phase HPLC to obtain the title compound (20 mg, 5%).

EIMS M+1: 264. $^1$H NMR δ (ppm) (200 MHz, CDCl$_3$): 7.20 (d, J=2 Hz, H-7, 1 H), 7.12 (dd, J=8 Hz, 2 Hz, H-11, 1 H), 6.74 (d, J=8 Hz, H-10, 1H), 4.87 (br s, ArOH, 1 H), 3.82 (br, H-2, 2 H), 3.02 (m, H-5, 1 H), 2.66 (d, J=4.8 Hz, CH$_3$-N$^+$H, 3 H), 2.23 (m, H-3, 4 H), 2.20 (s, CH$_3$Ar, 1 H), 1.97 (m, H 4, 2 H), 1.93 (m, H-4, 2 H). $^{13}$C NMR δ (ppm) (200 MHz, CDCl$_3$): 156.2 (C, C-9), 138.7 (CH, C-7), 135.0 (CH, C-11), 125.8 (C, C-8), 120.6 (C, C-6), 116.1 (CH, C-10), 63.9(2CH, C-2), 39.2 (CH$_3$, CH$_3$-N$^+$H, C-1), 36.9 (2CH$_2$, C-4), 36.6 (CH, C-5), 24.9 (2CH$_2$, C-3), 16.3 (CH$_3$, CH$_3$Ar).

EXAMPLE 15

5-(8-Methyl-8-aza-bicyclo[3.2.1]oct-3-ylsulfanyl)-biphenyl-2-ol, trifluoroacetate salt

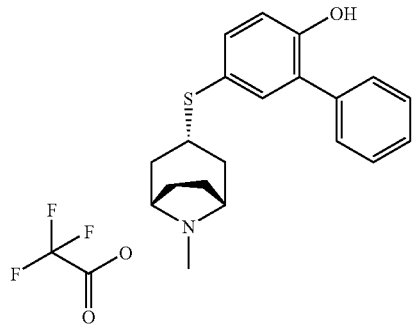

(i) 5-Thiocyanato-biphenyl-2-ol

To an ice-cooled suspension of Pb(SCN)$_2$ (569 mg, 1.76 mmol) in dry methylene chloride (10 mL), PhICl$_2$ (390 mg, 1.42 mmol) was added and the resulting mixture was stirred for 30 min at 0° C. under nitrogen. A solution of 2-phenyl-phenol (200 mg, 1.18 mmol) in dry methylene chloride (5 mL) was added dropwise. The mixture was stirred for 18 h at room temperature and filtered through a celite® pad washing extensively with methylene chloride. After addition of silica gel to the filtrate and evaporation of solvents, the mixture was purified by flash chromatography (10% ethyl acetate/hexane) to afford 171 mg (64%) of the title compound.

EIMS M+1: 228. IR (cm$^{-1}$): 3405, 1638, 1446, 1280, 1073. $^1$H NMR δ (ppm) (200 MHz, CDCl$_3$): 7.44–7.35 (m, 7 H), 6.98 (d, J=8.6 Hz, 1H). $^{13}$C NMR δ (ppm) (200 MHz, CDCl$_3$): 155.5 (C), 136.0 (C), 134.9 (CH), 133.4 (CH), 131.1 (C), 129.6 (2CH$_2$), 129.5 (2CH$_2$), 128.9 (CH), 118.5 (CH), 113.8 (C), 112.5 (C).

(ii) 5-Mercapto-biphenyl-2-ol

To a solution of 5-thiocyanato-biphenyl-2-ol (160 mg, 0.97 mmol) in absolute ethanol (8 mL) under nitrogen, sodium sulfide nonahydrate (298 mg, 1.1 6 mmol) was added. The resulting mixture was stirred at 85° C. for 20 min. The mixture was cooled down, made acidic with 10% aqueous HCl and extracted with ethyl acetate (×2). The combined organic layers were dried on MgSO$_4$ and concentrated in vacuo to give the title compound as a yellow solid (105 mg, 95%) which was quickly submitted to the next reaction without further purification.

EIMS M−1: 201.

(iii) 5-(8-Methyl-8-aza-bicyclo[3.2.1]oct-3-ylsulfanyl)-biphenyl-2-ol, trifluoroacetate salt To a solution of 5-mercapto-biphenyl-2-ol (105 mg, 0.52 mmol) in anhydrous acetone (3 ml), potassium carbonate (720 mg, 5.2 mmol) was added at room temperature. The mixture was stirred under nitrogen atmosphere and methanesulfonic acid 8-methyl-8-aza-bicyclo[3.2.1]oct-3-yl ester (103 mg, 0.47 mmol) in acetone (2 ml) was added dropwise. The resulting mixture was vigorously stirred at 70° C. for 18 h under nitrogen and was filtered and the solvent was removed in vacuo. The resulting residue was purified by reverse phase HPLC to afford the title compound (38 mg, 17%).

EIMS M+1: 264. $^1$H NMR δ (ppm) (500 MHz, DMSO): 9.94(brs, OH, 1 H), 9.31 (brs,NH, 1 H), 7.55 (d, J=7.3 Hz, H-13, 2 H), 7.41 (t, J=7.3 Hz, H-14, 2 H), 7.33 (m, H-7, 1 H), 7.32 (m, H-15, 1 H), 7.28 (dd, J=8.5, 2.6 Hz, H-11, 1 H), 6.96 (d, J=8.5 Hz, H-10, 1 H), 3.82 (br s, H-2, 2 H), 3.35 (m, H-5, 1 H), 2.59 (d, J=5.1 Hz, CH$_3$-N+H, 3 H), 2.14 (m, H-3, 2 H), 1.97 (m, H-4, 2 H), 1.86 (t, J=12.3Hz, H 4, 2 H), 1.92 (m, H-3, 2 H). $^{13}$C NMR δ (ppm) (125 MHz, DMSO): 154.9 (C, C-9), 137.6 (C, C-12), 136.9 (CH, C-7), 135.2 (CH, C-11), 129.0 (2CH, C-13), 128.4 (C, C-8), 127.9 (2CH, C-14), 126.8 (CH, C-15), 116.7 (CH, C-10), 63.1 (2CH, C-2), 38.0 (CH$_3$, CH$_3$-N$^+$, C-1), 36.2 (2CH$_2$, C-4), 35.3 (CH, C-5), 23.5 (2CH$_2$, C-3).

EXAMPLE 16

2,5-Dichloro-4-(8-methyl-8-aza-bicyclo[3.2.1]oct-3 (exo)-ylsulfanyl)-phenol

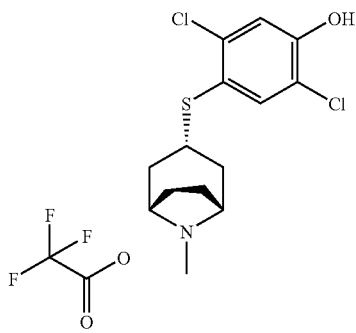

(i) 2,5-Dichloro-4-hydroxy-benzenesulfonyl chloride 2,5-Dichlorophenol (1.00 g, 6.17 mmol) was gradually added to chorosulfonic acid (2 mL, 30.85 mmol) at 0° C. Then it was heated at 80° C. for 1 hour. Then it was cooled at room temperature and poured onto crushed ice. Then ethyl acetate was added. The layers were separated and the aqueous phase was extracted with ethyl acetate. The combined organic phase was dried over MgSO$_4$, filtered and concentrated in vacuo to give 1.30 g (81%) of the title compound as a white solid, which was used in the next reaction without further purification.

EIMS M-1: 259.

(ii) 2,5-Dichloro-4-mercaptophenol

To a mixture of 2,5-dichloro-4-hydroxy-benzenesulfonyl chloride (1.28 g, 4.92 mmol) and a solution of 25% of H$_2$SO$_4$ (17 mL), Zinc dust (1.64 g, 24.56 mmol) was added slowly at room temperature. The reaction mixture was allowed to stir at 120° C. overnight. The mixture was then cooled at room temperature and toluene was added. The layers were separated and the aqueous phase was dried over, MgSO$_4$ filtered and concentrated in vacuo to give 514 mg (54%) of the title compound as a white solid, which was used in the next reaction without further purification.

EIMS: 193.

(iii) 2,5-Dichloro-4-(8-methyl-8-aza-bicyclo[3.2.1] oct-6-en-3(exo)-ylsulfanyl)-phenol To a solution of 2,5-dichloro-4-mercaptophenol (487 mg, 2.51 mmol) in acetone (5 mL), K$_2$CO$_3$ (3.20 g, 22.8 mmol) and a solution of methanesulfonic acid 8-methyl-8-aza-bicyclo[3.2.1]oct-3-yl ester (500 mg, 2.28 mmol) in acetone (5 mL) were added at room temperature. The resulting mixture was allowed to stir under reflux overnight. The mixture was concentrated in vacuo. The crude was purified first by Chromatography (Strong Cation Exchange, 2M ammonia in methyl alcohol) and then by reverse phase HPLC to afford the title compound (78 mg, 8%) as a white solid.

m. p. 193–194° C. EIMS+1: 318. $^1$H NMR δ (ppm) (200 MHz, MeOH-d4): 7.59 (s, 1 H), 7.06 (s, 1 H), 3.88 (s, 2 H), 3.49 (m, 1 H), 2.72 (s, 3 H), 2.31–1.88 (m, 8 H).

EXAMPLE 17

3,5-Dichloro-4-(8-methyl-8-aza-bicyclo[3.2.1]oct-3-(exo)-ylsulfanyl)-phenol

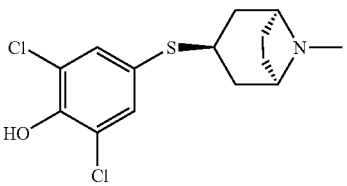

(i) 3,5-Dichloro-4-hydroxy-benzenesulfonyl chloride 3,5-Dichlorophenol (2.43 g, 14.9 mmol) was gradually added to chorosulfonic acid (4.9 mL, 74.6 mmol) at 0° C. Then it was heated at 80° C. for 1 hour. Then it was cooled at room temperature and poured onto crushed ice. The resulting white solid was filtered and washed with cool water. The solid was dissolved in EtOAc and dried over MgSO$_4$, filtered and and concentrated in vacuo (CIV) to give 2.24 g (58%) of the title compound as a white solid, which was used in the next reaction without further purification.

Ion Electrospray Mass Spectrum M-1: 259.

(ii) Acetic acid 2,6-dichloro-4-thiocyanato-phenyl ester

To compound from step (i) (1.00 g, 3.85 mmol), acetic acid (16 mL), acetic acid (16 mL), acetic anhydride (5.5 mL) and sodium acetate (1.60 g, 19.5 mmol) were added at room temperature. After stirring for 5 min., zinc dust (1.60 g) was added. The mixture was refluxed for 2 hours. Then it was cooled and the resulting solid was filtered, and the solvent was removed under vacuo. The residue was triturated with water, filtered and washed with water. The resulting solid was dissolved with CH$_2$Cl$_2$, dried over MgSO$_4$, filtered and CIV, affording 700 mg (65%) of the final compound as a white solid.

(iii) Acetic acid 2,6-dichloro-4-mercaptophenyl ester

To a suspension of compound from step (ii) (472 mg, 1.69 mmol) in MeOH (17 mL), a solution of sodium thiomethoxide (130 mg, 1.86 mmol) in MeOH (4 mL) was added at room temperature. The reaction mixture was allowed to stir at rt, under nitrogen atmosphere overnight. Then it was concentrated in vacuo and a 0.1 M solution of HCl (30 mL) and CH$_2$Cl$_2$ were added. The layers were separated and the aqueous phase was extracted with CH$_2$Cl$_2$. The combined organic phase was dried over MgSO$_4$ and CIV to afford 315 mg (79%) of the final compound as a white solid.

Ion Electrospray Mass Spectrum M+1: 237.

(iv) 3,5-Dichloro-4-(8-methyl-8-aza-bicyclo[3.2.1] oct-6-en-3-(exo)-ylsulfanyl)-phenol To a suspension of NaH (35 mg, 1.40 mmol) in dry THF (10 mL), under nitrogen atmosphere, a solution of compound from step (iii) (300 mg, 1.27 mmol) in dry THF (5 mL) was added at room temperature. The mixture was allowed to stir at this temperature for 15 min. Then a solution of methanesulfonic acid 8-methyl-8-aza-bicyclo[3.2.1]oct-3-yl ester (252 mg, 1.15 mmol) in dry THF (5 mL) was added. The reaction mixture was stirred under reflux for 2 days. Then it was cooled and concentrated in vacuo. The crude was purified first by chromatography (Strong Cation Exchange, 2M ammonia in methyl alcohol) giving an exo/endo mixture. This mixture was purified by reverse phase HPLC to obtain the title compound (5.6 mg, 1%) as a white solid.

Ion Electrospray Mass Spectrum M+1: 318

$^1$H NMR δ (ppm) (200 MHz, MeOH-d4): 7.45 (s, 2 H), 3.87 (br s, 2 H), 3.49–3.38 (m, 1 H), 2.72 (s, 3 H), 2.31–1.83 (m, 8 H).

EXAMPLE 18

2-Bromo4-(8-methyl-8-aza-bicyclo[3.2.1oct-3-(exo)-ylsulfanyl)-phenol

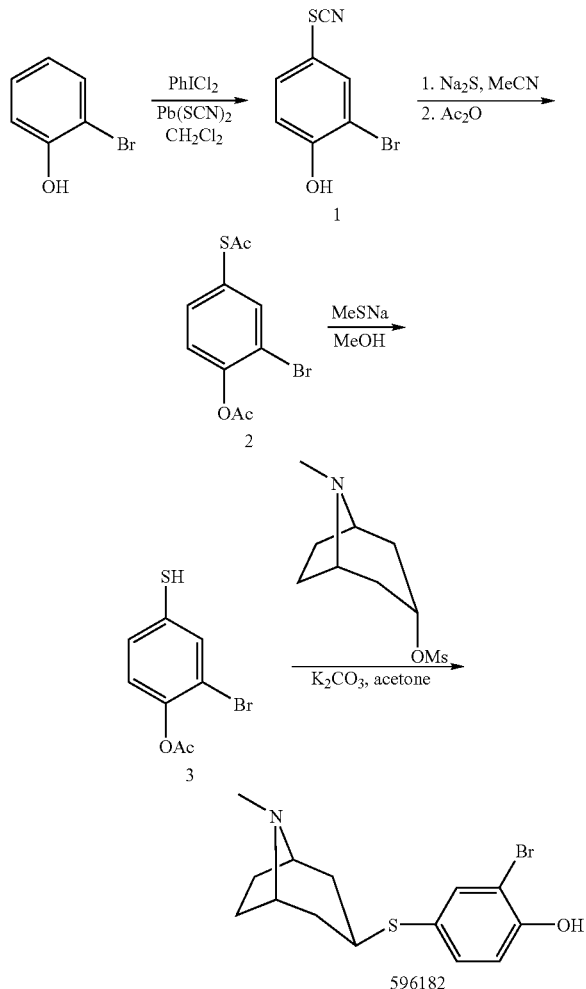

(i) 2-bromo-4-thiocyanatophenol

To a suspension of lead thiocyanate (6.49 g, 20.05 mmol) in CH$_2$Cl$_2$ (125 mL) under nitrogen at 0° C. PhICl$_2$ (4.41 g, 16.05 mmol) was added in one portion. After 20 min at 0° C. a solution of 2-bromophenol (2.31 g, 1.55 mL, 13.37 mmol) in CH$_2$Cl$_2$ (10 mL) was added. After stirring the mixture for 45 min at 0° C. the salts were filtered and the solvent evaporated. The crude mixture was purified by silica gel flash chromatography (hexane-EtOAc 5:1→2:1) to yield 1 (2-bromo4-thiocyanatophenol) (1031 mg, 33%) as a pale yellow oil.

$^1$H NMR (200 MHz, CDCl$_3$) δ (ppm) 7.72 (d, J=2.2 Hz, 1H), 7.45 (dd, J=8.6, 2.2 Hz, 1H), 7.08 (d, J=8.6 Hz, 1H), 5.78 (br s, 1H). $^{13}$C NMR (75 MHz, CDCl$_3$) δ (ppm) 158.4, 138.3, 134.4, 119.1, 115.3, 112.9, 112.6. MS m/z 229 (M−1).

(ii) Acetic acid 4-acetylsulfanyl-2-bromo-phenyl ester

A mixture of 1 (615 mg, 2.67 mnmol) and Na$_2$S.9H$_2$O (706 mg, 2.94 mmol) in MeCN (25 mL) was heated at 80° C. for 1 h. After cooling to 23° C. acetic anhydride (1.3 mL, 13.35 mmol) was added and the reaction stirred at 23° C. for 1 h. The solution was diluted with brine and extracted with CH$_2$Cl$_2$, dried (Na$_2$SO$_4$) and evaporated. Purification by silica gel flash chromatography afforded 2 (acetic acid 4-acetylsulfanyl-2-bromo-phenyl ester) (630 mg, 82%) as a yellow oil.

$^1$H NMR (200 MHz, CDCl$_3$) δ (ppm) 7.67 (d, J=2.0 Hz, 1H), 7.37 (dd, J=8.4, 2.0 Hz, 1H), 7.18 (d, J=8.4 Hz, 1H), 2.42 (s, 3H), 2.38 (s, 3H). $^{13}$C NMR (75 MHz, CDCl$_3$) δ (ppm) 193.3, 168.6, 149.6, 139.1, 134.9, 127.4, 124.7, 117.1. MS m/z 290 (M+1).

(iii) Acetic acid 4-thio-2-bromo-phenyl ester

To a solution of 2 (630 mg, 2.18 mmol) in MeOH (20 mL) sodium thiomethoxide (153 mg, 1M in MeOH, 2.18 mmol) was added at 23° C. After stirring for 1 h the reaction was poured over an aqueous solution of HCl 5% and extracted with CH$_2$Cl$_2$, dried (Na$_s$SO$_4$) and evaporated to yield 3. The crude 3 (530 mg) was used in the next reaction.

$^1$H NMR (200 MHz, CDCl$_3$) δ (ppm) 7.53 (d, J=2.2 Hz, 1H), 7.22 (dd, J=8.4, 2.2 Hz, 1H), 6.99 (d, J=8.4 Hz, 1H), 2.34 (s, 3H). MS m/z 246 (M−1).

(iv) 2-Bromo-4-(8-methyl-8-aza-bicyclo[3.2.1]oct-3-(exo)-ylsulfanyl)-phenol

A mixture of crude 3 (530 mg, 2.14 mmol), methanesulfonic acid 8-methyl-8-aza-bicyclo[3.2.1]oct-3-yl ester (470 mg, 2.14 mmol) and K$_2$CO$_3$ (593 mg, 4.36 mmol) in acetone (50 mL) was heated at 65° C. for 20 h the mixture was diluted with brine and extracted with CH$_2$Cl$_2$, dried (Na$_2$SO$_4$) and evaporated. The crude was purified first by C18 silica gel cartridges (H$_2$O→H$_2$O—MeOH→MeOH) and finally by reverse phase HPLC to yield 2-bromo-4-(8-methyl-8-aza-bicyclo[3.2.1]oct-3-ylsulfanyl)-phenol (174 mg, 22%) as a white solid.

$^1$H NMR (200 MHz, CDCl$_3$) δ (ppm) 7.62 (d, J=2.2 Hz, 1H), 7.31 (dd, J=8.4, 2.2 Hz, 1H), 6.89 (d, J=8.4 Hz, 1H), 3.87–3.84 (m, 2H), 3.31 (sp, J=5.1 Hz, 1H), 2.70 (s, 3H), 2.31–2.24 (m, 2H), 2.12–1.85(m, 7H). $^{13}$C NMR (75 MHz, CDCl$_3$) δ (ppm) 157.0, 141.2, 137.4, 123.9, 118.2, 111.5, 65.9, 39.7, 38.6, 37.7, 25.3. MS m/z 329 (M+1).

EXAMPLE 19

3-Methyl-4-(8-methyl-8-aza-bicyclo[3,2,1]oct-3-(exo)-ylsulfanyl)-phenol, trifluoroacetate salt

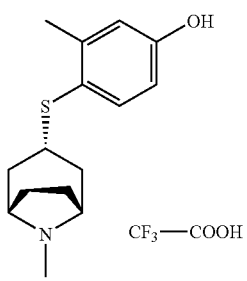

(i) 3-methyl-4-thiocyanato-phenol

To an ice-cooled suspension of Pb(SCN)$_2$ (4.48 g, 13.9 mmol) in dry methylene chloride (100 mL), PhICl$_2$ (3.04 g, 11.1 mmol), prepared according to D. Koyuncu et al., *J. Chem. Res.* (S) 1990, 21, was added and the resulting mixture was stirred for 40 min at 0° C. under nitrogen. M-cresol (1 g, 1 mL, 9.2 mmol) was added. The mixture was stirred at room temperature for 2 h, and filtered through a celite pad washing extensively with methylene chloride. After addition of silicagel to the filtrate and evaporation of solvents, the mixture was purified by flash chromatography (10% ethyl acetate/hexane) to afford 1.48 g (97%) of the title compound.

Ion Electrospray Mass Spectrum M-1: 164. $^1$H NMR (200 MHz, CDCl$_3$) δ (ppm): 7.50 (d, J=5.8 Hz, 1 H), 6.81 (d, J=1.8 Hz, 1 H), 6.72 (dd, J=5.8 Hz, 1.8 Hz, 1 H), 5.18 (br s, OH), 2.50 (s, 3 H); $^{13}$C NMR (50 MHz, CDCl$_3$) δ (ppm): 157.3, 142.3, 135.0, 117.6, 113.9, 111.8, 110.8.

(ii) 4-Mercapto-3-methyl-phenol

To a hot (85° C.) solution of the intermediate from step (i) (1.48 g, 8.97 mmol) in absolute ethanol (60 mL) under nitrogen, sodium sulfide nonahydrate (2.60 g, 10.76 mmol) was added. The resulting mixture was stirred at 85° C. for 2 h. The mixture was cooled down, made acidic with an aqueous solution of HCl (10%) and extracted with methylene chloride. The organic layer was washed once with water and brine, dried on MgSO$_4$ anhydrous and concentrated in vacuo to give the title compound impurified with its disulfide (1.23 g). The mixture was quickly submitted to the next reaction without further treatment.

Ion Electrospray Mass Spectrum M-1: 139.

(iii) 3-Methyl-4-(8-methyl-8-aza-bicyclo[3,2,1]oct-3-(exo)-ylsulfanyl)-phenol

To a solution of intermediate from step (ii) (1.23 g, 8.80 mmol) and methanesulfonic acid 8-methyl-8-aza-bicyclo[3.2.1]oct-3-yl ester (1.73 g, 7.92 mmol) in dry dimethylformamide (30 mL) under nitrogen, potassium carbonate anhydrous (6.10 g, 44.0 mmol) was added. The resulting mixture was vigorously stirred at room temperature for 18 h under nitrogen. The mixture was filtered and the solvent was removed in vacuo. The residue was was purified by reverse phase HPLC to obtain the title compound (10.2 mg, 0.5%).

Ion Electrospray Mass Spectrum M+1: 264. IR (cm$^{-1}$): 3200–3000, 1674, 1593, 1237, 799. $^1$H NMR (200 MHz, CD$_3$OD) δ (ppm): 7.32 (d, J=8.2 Hz, 1 H), 6.72 (d, J=2.8 Hz, 1 H), 6.60 (dd, J=8.2 Hz, 2.8Hz, 1 H), 3.82 (br m, 2 H), 3.20 (m, 1 H), 2.71 (s, 3 H), 2.41 (s, 3 H), 2.26 (m, 2 H), 2.10–1.85 (m, 6 H) $^{13}$C NMR (75 MHz, CD$_3$OD) δ (ppm): 160.5, 145.9, 139.9, 122.2, 119.3, 115.7, 66.4, 40.1, 39.3, 37.9, 25.7, 22.4

EXAMPLE 20

4-(9-Methyl-9-aza-bicyclo[3,3,1]non-3(exo)-ylsulfanyl)-phenol, trifluoroacetate salt

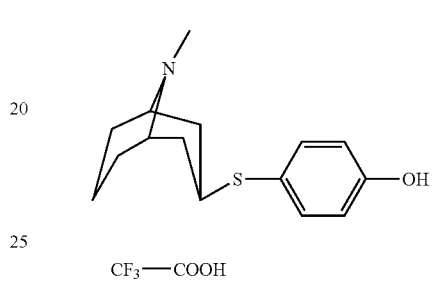

(i) 9-Methyl-9-aza-bicyclo[3,3,1]nonan-3-(endo)-ol

To a −78° C. cooled solution of pseudopelletierine (771 mg, 5.04 mmol), obtained from its chloro hydrate (pseudopelletierine chloride, commercially available) by treatment with saturated aqueous solution of NaHCO$_3$, extracted with methylene chloride, and dried; in THF anhydrous (20 mL), a solution 1.0 M of DIBAL-H in hexane or toluene (10.8 mL, 10.8 mmol) was added dropwise under N$_2$. The mixture was stirred and allowed to reach rt. for 3 h. The reaction was quenched with water (2 mL) and poured into diethyl ether (60 mL). NaHCO$_3$ anhydrous (20 g) and Na$_2$SO$_4$ anhydrous (20 g) were added. The mixture was stirred for 2 h at rt., and then, it was filtered and the filtrate was evaporated. The residue was the title compound pure, 684 mg, 88%.

Ion Electrospray Mass Spectrum M+1: 156. $^1$H NMR (200 MHz, CDCl$_3$) δ (ppm): 4.16 (m, 1 H), 2.95 (br m, 2 H), 2.40–2.20 (m, 2 H), 2.00–1.80 (m, 3 H), 1.40–1.25 (m, 3 H), 1.20–1.05 (m, 2H) $^{13}$C NMR (50 MHz, CDCl$_3$) δ (ppm): 62.9, 51.6, 40.4, 34.8, 24.9, 14.4

(ii) 3-(endo)-Hydroxy-9-aza-bicyclo[3,3,1]nonane-9-carboxylic acid methyl ester

To a solution of the intermediate from step (i) (615 mg, 3.97 mmol) in dry chloroform (115 mL), methyl chloroformate (1.8 mL, 23.8 mmol) followed by potassium carbonate (457 mg, 4.56 mmol) were added. The mixture was heated at 80° C. and stirred under N$_2$ overnight. The reaction was cooled down, quenched with water (10 mL) and extracted with chloroform. The organic layer was dried on MgSO$_4$ anhydrous, and the solvent was removed in vacuo. The residue (800 mg) was purified by flash chromatography (30% ethyl acetate/hexane) to give the title compound, 200 mg, 25%.

Ion Electrospray Mass Spectrum M+1: 200. $^1$H NMR (300 MHz, CDCl$_3$) δ (ppm): 4.34 (br d, 2 H), 3.56 (s, 3 H), 3.53 (m, 1 H), 2.21 (m, 2 H), 2.17 (m, 1 H), 1.50–1.30 (m, 7 H). $^{13}$C NMR (75 MHz, CDCl$_3$) δ (ppm): 62.9, 51.6, 40.4, 34.8, 24.9, 14.4

(iii) 3-(endo)-Methanesulfonyloxy-9-aza-bicyclo[3,3,1]nonane-9-carboxylic acid methyl ester To an ice-cooled solution of the intermediate from step (ii) (200 mg, 1.0 mmol) in methylene chloride anhydrous, pyridine anhydrous (0.073 mL, 0.9 mmol) followed by methanesulfonate chloride (0.085 mL, 1.1 mmol) were added under $N_2$. The mixture was stirred overnight and allowed to reach rt. The reaction was quenched with an aqueous solution of $NH_4OH$ (15%), and extracted with methylene chloride. The organic layer was washed with brine and dried. The solvent was removed in vacuo to give the title compound, 210 mg, 76%.

Ion Electrospray Mass Spectrum M+1: 278. $^1$H NMR (200 MHz, $CDCl_3$) δ (ppm): 4.63 (m, 1 H), 4.50 (br m, 2 H), 3.64 (s, 3 H), 2.99 (s, 3 H), 2.42 (m, 2 H), 1.80–1.60 (m, 8 H). $^{13}$C NMR (50 MHz, $CDCl_3$) δ (ppm): 156.0, 74.5, 52.5, 45.0, 38.5, 32.4, 29.6, 14.0

(iv) 3-(exo)-(4-Hydroxy-phenylsulfanyl)-9-aza-bicyclo[3,3,1]nonane-9-carboxylic acid methyl ester To a solution of the intermediate from step (iii) (107.1 mg, 0.39 mmol) and 4-mercaptophenol (98.3 mg, 0.78 mmol) in dry DMF (25 mL), ceasium fluoride (118.5 mg, 0.78 mmol) was added. The mixture was heated at 60° C. and stirred overnight under $N_2$. The reaction was quenched with water, and extracted with ethyl acetate. The organic layer was washed with water and dried. The solvent was removed in vacuo to give the title compound, which was submitted to the next reaction without further treatment.

Ion Electrospray Mass Spectrum M+1: 308, M−1: 306.

(v) 4-(9-Methyl-9-aza-bicyclo[3,3,1]non-3-(exo)-ylsulfanyl)-phenol, trifluoroacetate salt To an ice-cooled solution of the intermediate from step (iv) (119.7 mg, 0.39 mmol) in ethyl ether anhydrous (THF anhydrous can be used too) (2 mL), lithium aluminium hydride (LAH) (74 mg, 1.95 mmol) was added. The mixture was stirred overnight under $N_2$ and allowed to reach rt. The reaction was quenched with water and methanol at 0° C. (violent reaction), and filtered. The filtrate was evaporated and the residue was submitted to SCX collecting the desired product slightly impurified, which was purified by reverse phase HPLC to obtain the title compound, 30 mg, 21%.

The structural analysis was done with the ammonium salt and the free amine.

Ion Electrospray Mass Spectrum M+1: 264, M−1: 262 $^1$H NMR (500 MHz, $CD_3OD$) δ (ppm) for the free amine: 7.38 (d, J=8.6 Hz, 2 H), 6.75 (d, J=8.6 Hz, 2 H), 3.68 (m, 1 H), 3.50 (br s, 2 H), 2.82 (s, 3 H), 2.25–2.15 (m, 6 H), 2.03–1.85 (m, 3 H), 1.60 (m, 1 H). $^{13}$C NMR (150 MHz, $CD_3OD$) δ (ppm) for the ammonium salt. Two N-methyl invertomers were detected depending on the N-methyl position. Both are described:

A: 158.6, 137.2, 120.6, 115.9, 56.2, 38.8, 37.9, 36.9, 20.9, 17.8.

B: 158.5, 136.9, 120.3, 115.9, 55.7, 38.5, 36.9, 29.2, 28.8, 17.5.

EXAMPLE 21

5-[(8-methyl-8-azabicylo[3.2.1]oct-3-yl)thiol-2-pyridinylamine

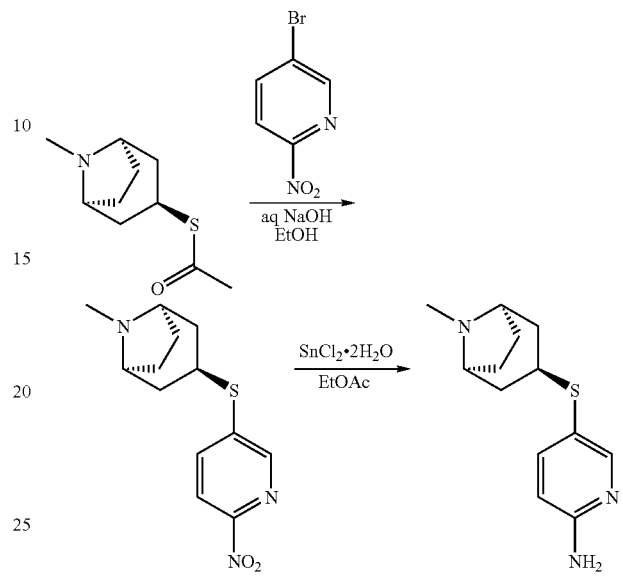

(i) 8-methyl-3-[(6-nitro-3-pyridinyl)thio]-8-azabicyclo[3.2.1]octane.

A mixture of (8-methyl-8-azabicylo[3.2.1]oct-3-yl)ethanethioate (1.24 g) and 2-nitro-5-bromopyridine (790 mg) in ethanol (15 ml) and aqueous sodium hydroxide (2M, 2 ml) was stirred at room temperature overnight. The mixture was applied directly to an SCX cartridge and eluted sequentially with methanol then 2M ammonia in methanol to yield the crude product (500 mg). This was purified by preparative LC-MS to yield 8-methyl-3-[(6-nitro-3-pyridinyl)thio]-8-azabicyclo[3.2.1]octane (50 mg).

(ii) 5-[(8-methyl-8-azabicylo[3.2.1]oct-3-yl)thio]-2-pyridinylamine.

A mixture of 8-methyl-3-[(6-nitro-3-pyridinyl)thio]-8-azabicyclo[3.2.1]octane (50 mg) and tin (II) chloride dihydrate (202 mg) in ethyl acetate was heated under reflux for 4 days and the worked up by quenching with aqueous sodium hydrogen carbonate solution. The product was extracted into ethyl acetate and the organic layer dried, filtered and concentrated to yield the crude aminopyridine (30 mg). The material was cleaned up on an SCX cartridge as above to yield 5-[(8-methyl-8-azabicylo[3.2.1]oct-3-yl)thio]-2-pyridinylamine (25 mg).

EXAMPLE 22 (Intermediate Preparation)

3-chloro-4-[(8-methyl-8-azabicylo[3.2.1]oct-3-yl)thio]phenyl trifluoromethanesulfonate

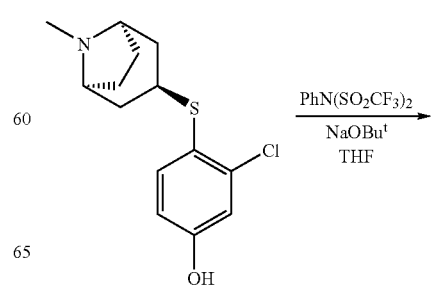

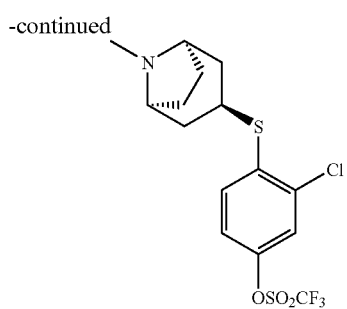

3-Chloro-4-[(8-methyl-8-azabicylo[3.2.1]oct-3-yl)thio] phenol (Example 72, 274 mg) was dissolved in anhydrous THF (10 ml) under nitrogen and cooled to 0° C. To this was added in one portion sodium tert-butoxide (97 mg) and the solution stirred for 10 minutes. The flask was removed from the ice-bath and N-phenyltrifluoromethanesulfonimide (750 mg) added. The solution was stirred at room temperature overnight. Water was added and the layers separated. The aqueous phase was extracted with ethyl acetate and the combined organics washed with saturated sodium hydrogen carbonate solution, dried (MgSO$_4$), filtered and evaporated to dryness. The material was purified on an SCX cartridge eluting sequentially with methanol then 2M ammonia in methanol to provide 3-chloro-4-[(8-methyl-8-azabicylo[3.2.1]oct-3-yl)thio]phenyl trifluoromethanesulfonate (192 mg).

EXAMPLE 23 a) 3-{[2-chloro-4-(3-pyridinyl)phenyl]thio}-8-methyl-8-azabicyclo[3.2.1]octane

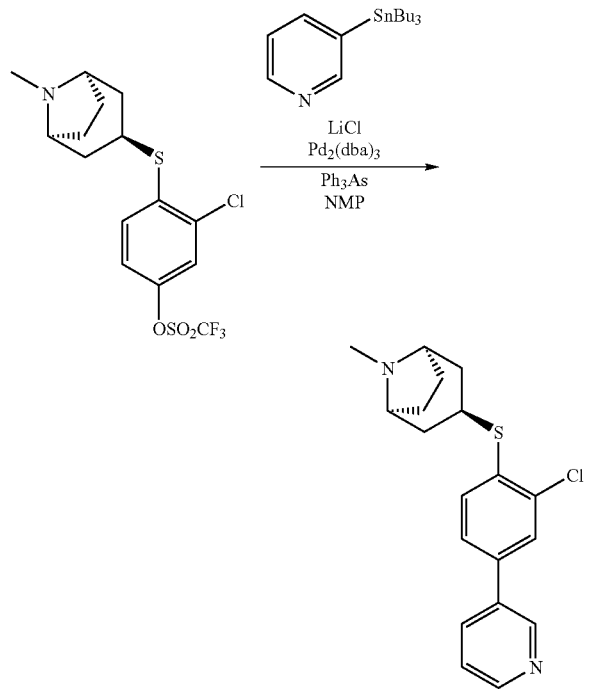

A mixture of 3-chloro-4-[(8-methyl-8-azabicylo[3.2.1] oct-3-yl)thio]phenyl trifluoromethanesulfonate (215 mg), lithium chloride (70 mg), triphenylarsine 32 mg) and tris(dibenzylideneacetone)-dipalladium (0) (20 mg) was stirred in N-methylpyrrolidinone (10 ml) under nitrogen for 5 minutes. To this was added 3-tributylstannylpyridine (200 mg) and the solution heated to 100° C. for 2 hours. The solution was cooled to room temperature and aqueous sodium hydroxide (10%) added to quench the reaction. The mixture was extracted three times with dichloromethane, the combined organics dried (MgSO$_4$), filtered and evaporated to dryness. The material was purified on an SCX cartridge eluting sequentially with methanol and 2M ammonia in methanol, followed by preparative LC-MS yielding 3-{[2-chloro-4-(3-pyridinyl)phenyl]thio}-8-methyl-8-azabicylo[3.2.1]octane (54 mg)

b) 8-methyl-3-{[4-(3-pyridinyl)phenyl]thio}-8-azabicyclo[3.2.1]octane

Also prepared by this procedure was 8-methyl-3-{[4-(3-pyridinyl)phenyl]thio}-8-azabicyclo[3.2.1]octane (from 4-[(8-methyl-8-azabicylo[3.2.1]oct-3-yl)thio]phenyl trifluoromethanesulfonate and 3-tributylstannylpyridine).

EXAMPLE 24

8-methyl-3-{[4-(5-pyrimidinyl)phenyl]thio}-8-azabicyclo[3.2.1]octane

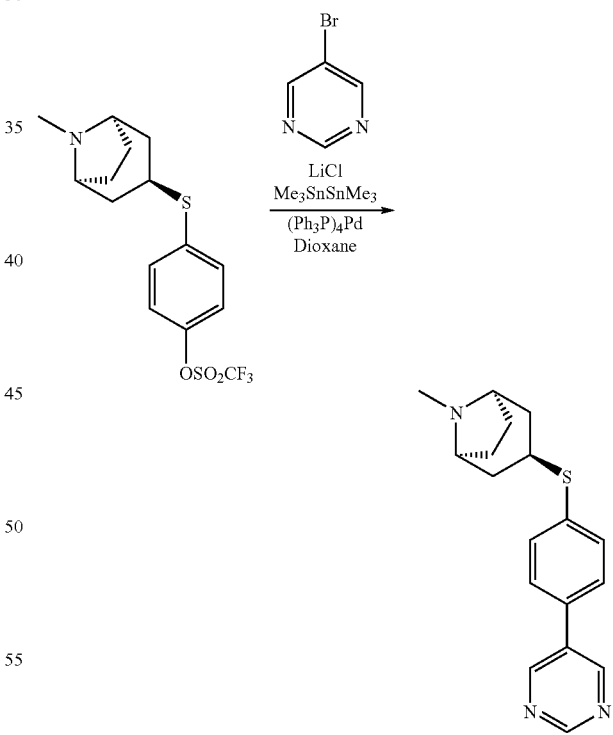

To a mixture of 4-[(8-methyl-8-azabicylo[3.2.1]oct-3-yl)thio]phenyl trifluoromethanesulfonate (450 mg), 5-bromopyrimidine (187 mg), lithium chloride (150 mg) and tetrakis(triphenylphosphine) palladium (0) (68 mg) under nitrogen were added hexamethylditin (386 mg) and dioxane (15 ml). The mixture was heated under reflux overnight and then poured into a mixture of aqueous potassium fluoride (1.9 g in 13 ml water) and ethyl acetate (13 ml). This mixture was stirred vigorously for 2 hours, passed through a sintered funnel and the layers separated. The organic phase was washed with brine, dried (MgSO$_4$), filtered and evaporated. The crude material was purified on an Isco CombiFlash device, followed by UV-guided LC to yield 8-methyl-3-{[4-(5-pyrimidinyl)phenyl]thio}-8-azabicyclo[3.2.1]octane (45 mg)

EXAMPLE 25 a) [1,1'-biphenyl]4-yl 8-methyl-8-azabicyclo[3.2.1]oct-3-yl sulfide

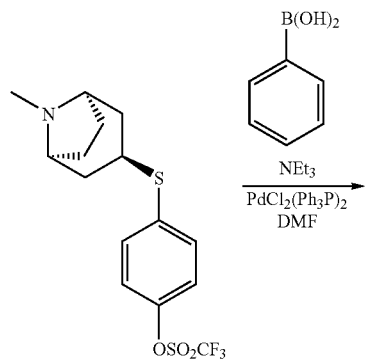

To a mixture of 4-[(8-methyl-8-azabicylo[3.2.1]oct-3-yl)thio]phenyl trifluoromethanesulfonate (0.4 g) and phenylboronic acid (0.25 g) in DMF (5 ml) were added triethylamine (0.58 ml) followed by dichlorobis(triphenylphosphine) palladium (II) (0.04 g). The solution was heated at 90° C. for 4 hours, cooled to room temperature and diluted with ethyl acetate. This was washed with saturated aqueous sodium hydrogen carbonate solution, then brine, dried (MgSO$_4$), filtered and evaporated. Partial clean up was achieved using preparative LC-MS. The mixture was stirred with aqueous sodium hydroxide solution (0.5M) to hydrolyse residual triflate to the phenol. The product was extracted into ethyl acetate, still however contaminated with some of the phenol. The material was loaded onto a PE-AX column and eluted with methanol with the final clean up by preparative LC-MS to yield [1,1'-biphenyl]4-yl 8-methyl-8-azabicyclo[3.2. 1]oct-3-yl sulfide.

Also prepared by this procedure from 4-[(8-methyl-8-azabicylo[3.2.1]oct-3-yl)thio]phenyl trifluoromethanesulfonate and the appropriate arylboronic acid were:

b) N-{4'-[(8-methyl-8-azabicylo[3.2.1]oct-3-yl)thio][1,1'-biphenyl]-3-yl}acetamide c) 8-methyl-3-{[4-(3-pyridinyl)phenyl]thio}-8-azabicyclo[3.2.1]octane d) 3-{[2',4'-dichloro(1,1'-biphenyl]4-yl]thio}-8-methyl-8-azabicyclo[3.2.1]octane e) 3-{[4-(1-benzofuran-2-yl)phenyl]thio}-8-methyl-8-azabicylo[3.2.1]octane f) 3-{[4-(5-carboxamido-3-pyridinyl)phenyl]thio}-8-methyl-8-azabicyclo[3.2.1]octane g) 3-{[4-(3carboxamido-phenyl)phenyl]thio}-8-methyl-8-azabicyclo[3.2.1]octane h) 3-{[4-(3,4,5,6-dehydro-2-oxo-piperidin-5-yl)phenyl]thio}-8-methyl-8-azabicyclo[3.2.1]octane

EXAMPLE 26 a) 3-chloro-4-[(8-methyl-8-azabicylo[3.2.1]oct-3-yl)thio]phenylformamide

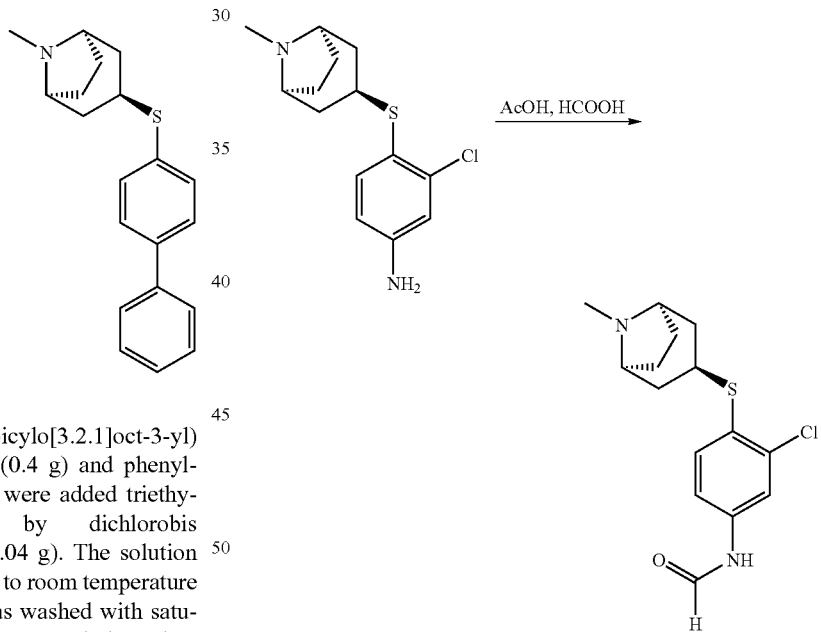

A mixture of acetic acid (0.96 g) and formic acid (0.53 g) was heated under reflux for 2 hours. To this was added 3-chloro-4-[(8-methyl-8-azabicylo[3.2.1]oct-3-yl)thio]phenylamine (265 mg) and heating continued for 1.5 hours. The crude mixture was placed on an SCX cartridge and eluted with methanol followed by 2M ammonia in methanol. The impure product was then subjected to flash chroamtography on silica gel (gradient elution with increasing percentage of methanol in chloroform) to yield material of 93% purity. Final clean up by preparative LC-MS gave 3-chloro-4-[(8-methyl-8-azabicylo[3.2.1]oct-3-yl)thio]phenylformamide (40 mg)

b) 4-[(8-methyl-8-azabicylo[3.2.1]oct-3-yl)thio]phenylformamide

Prepared in an analogous manner was 4-[(8-methyl-8-azabicylo[3.2.1]oct-3-yl)thio]phenylformamide.

EXAMPLE 27 a) N-{4-[(8-methyl-8-azabicylo[3.2.1]oct-3-yl)thio]phenyl]4-thiazolecarboxamide

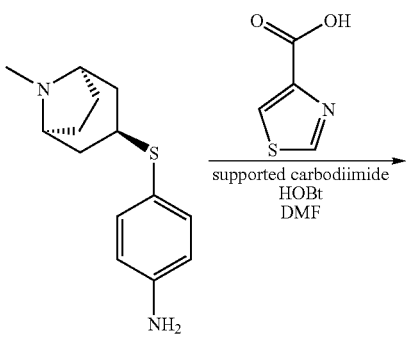

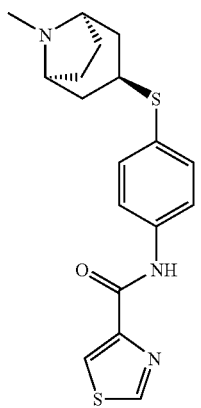

A mixture of 4-[(8-methyl-8-azabicylo[3.2.1]oct-3-yl)thio]phenylamine (50 mg), 4-carboxythiazole (52 mg), 1-hydroxybenzotriazole (61 mg) and carbodiimide resin (1.7 mmol/g, 470 mg) in DMF (7 ml) was stirred at room temperature for 3 days. The mixture was filtered then passed through an SCX cartridge, eluting with methanol followed by 2M ammonia in methanol, providing N-{4-[(8-methyl-8-azabicylo[3.2.1]oct-3-yl)thio]phenyl]-4-thiazolecarboxamide as a white solid (55 mg)

Prepared in a similar fashion were:
b) N-{4-[(8-methyl-8-azabicylo[3.2.]oct-3-yl)thio]phenyl]-1,2,3-thiadiazole-4-carboxamide
c) N-{4-[(8-methyl-8-azabicylo[3.2.1]oct-3-yl)thio]phenyl]-3-thiophenecarboxamide
d) N-{3-Chloro-4-[(8-methyl-8-azabicylo[3.2.1]oct-3-yl)thio]phenyl]-3-thiophenecarboxamide

EXAMPLE 28

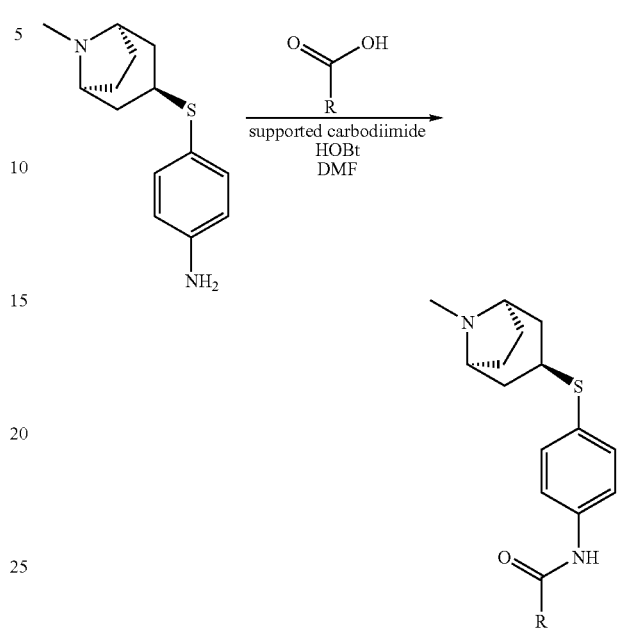

Stock solutions of 4-[(8-methyl-8-azabicylo[3.2.1]oct-3-yl)thio]phenylamine ("the substrate", 0.05M), 1-hydroxybenzotriazole ("the reagent", 0.1M) and a set of 24 carboxylic acids ("the monomers", 0.1M) were all prepared in DMF. Each well of a 24-well RPS plate was loaded with carbodiimide resin (loading 1.7 mmol/g, 59 mg) and then each treated with 0.5 ml of the substrate solution, the reagent solution and a monomer solution. These were stirred at room temperature for 72 hours, filtered from the resin, passed through SCX cartridges eluting with methanol then 2M ammonia in methanol and concentrated. The materials were then further purified by preparative LC-MS to provide the carboxamides in an average yield of 67%

By this method were prepared:
a) N-{4-[(8-methyl-8-azabicylo[3.2.1]oct-3-yl)thio]phenyl] benzamide
b) N-{4-[(8-methyl-8-azabicylo[3.2.1]oct-3-yl)thio]phenyl]-4-nitrobenzamide
c) 4-Methoxy-N-{4-[(8-methyl-8-azabicylo[3.2.1]oct-3-yl)thio]phenyl]benzamide
d) 4-Isopropyl-N-{4-[(8-methyl-8-azabicylo[3.2.1]oct-3-yl)thio]phenyl]benzamide
e) 4-Chloro-N-{4-[(8-methyl-8-azabicylo[3.2.1]oct-3-yl)thio]phenyl]benzamide
f) 4-Methyl-N-{4-[(8-methyl-8-azabicylo[3.2.1]oct-3-yl)thio]phenyl]benzamide
g) N-{4-[(8-methyl-8-azabicylo[3.2.1]oct-3-yl)thio]phenyl]-2-phenylacetamide
h) N-{4-[(8-methyl-8-azabicylo[3.2.1]oct-3-yl)thio]phenyl]-2-(4-methylphenyl)acetamide
i) N-{4-[(8-methyl-8-azabicylo[3.2.1]oct-3-yl)thio]phenyl]-2-(4-methoxyphenyl)acetamide
j) N-{4-[(8-methyl-8-azabicylo[3.2.1]oct-3-yl)thio]phenyl]-2-(4-fluorophenyl)acetamide
k) N-{4-[(8-methyl-8-azabicylo[3.2.1]oct-3-yl)thio]phenyl]-3-phenylpropanamide
l) N-{4-[(8-methyl-8-azabicylo[3.2.1]oct-3-yl)thio]phenyl] 4-phenylbutanamide m) N-{4-[(8-methyl-8-azabicylo[3.2.1]oct-3-yl)thio]phenyl]propanamide
n) 2-Methyl-N-{4-[(8-methyl-8-azabicylo[3.2.1]oct-3-yl)thio]phenyl]propanamide
o) 2,2-Dimethyl-N-{4-[(8-methyl-8-azabicylo[3.2.1]oct-3-yl)thio]phenyl]propanamide
p) N-{4-[(8-methyl-8-azabicylo[3.2.1]oct-3-yl)thio]phenyl]butanamide
q) 3,3-Dimethyl-N-{4-[(8-methyl-8-azabicylo[3.2.1]oct-3-yl)thio]phenyl]butanamide
r) N-{4-[(8-methyl-8-azabicylo[3.2.1]oct-3-yl)thio]phenyl]-3-butenamide
s) N-{4-[(8-methyl-8-azabicylo[3.2.1]oct-3-yl)thio]phenyl]cycohexanecarboxamide
t) N-{4-[(8-methyl-8-azabicylo[3.2.1]oct-3-yl)thio]phenyl]cyclopentanecarboxamide
u) N-{4-[(8-methyl-8-azabicylo[3.2.1]oct-3-yl)thio]phenyl]-2-pyridinecarboxamide
v) N-{4-[(8-methyl-8-azabicylo[3.2.1]oct-3-yl)thio]phenyl]-3-pyridinecarboxamide
x) N-{4-[(8-methyl-8-azabicylo[3.2.1]oct-3-yl)thio]phenyl]-3-thiophenecarboxamide
y) N-{4-[(8-methyl-8-azabicylo[3.2.1]oct-3-yl)thio]phenyl[-3-indolecarboxamide

EXAMPLE 29 a) N-{4-[(8-methyl-8-azabicylo[3.2.1]oct-3-yl)sulfonyl]phenyl]-3-thiophenecarboxamide

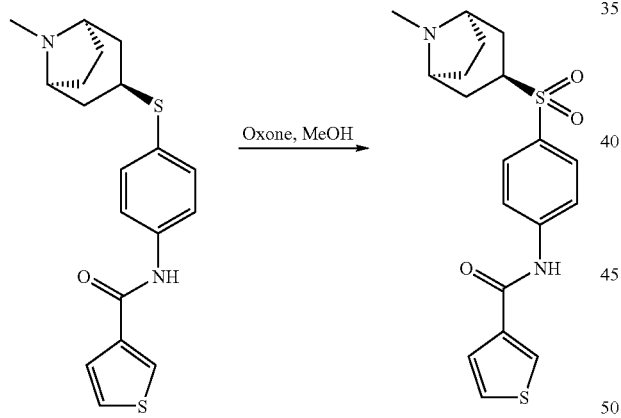

To a solution of N-{4-[(8-methyl-8-azabicylo[3.2.1]oct-3-yl)thio]phenyl]-3-thiophenecarboxamide (130 mg) in methanol (5 ml) was added a solution of Oxone (446 mg) in water. The mixture was stirred at room temperature for 30 minutes and then applied directly to an SCX cartridge. The impure product eluted with methanol and was subjected to further clean up by preparative LC-MS to yield N-{4-[(8-methyl-8-azabicylo[3.2.1]oct-3-yl)sulfonyl]phenyl]-3-thiophenecarboxamide (75 mg).

b) 4-[(8-methyl-8-azabicylo[3.2.1]oct-3-yl)sulfonyl] phenylformamide

Prepared in a similar manner was 4-[(8-methyl-8-azabicylo[3.2.1]oct-3-yl)sulfonyl]phenylformamide

EXAMPLE 30

3-(exo)-[2-Chloro-4-(pyridin-3-yloxy)-phenylsulfanyl]-8-methyl-8-azabicyclo[3.2.1]octane

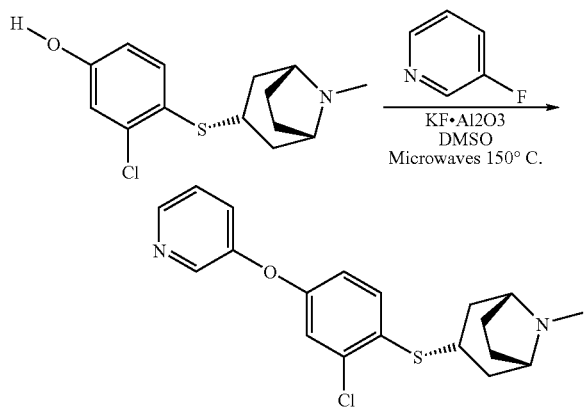

A mixture of 3-Chloro-4-(8-methyl-8-aza-bicyclo[3.2.1] oct-3-ylsulfanyl)-phenol (Example 72, 1.0 eq), 3-fluoropyridine (1.0 eq) 18-crown-6 (1 eq) and 37% w/w potassium-fluoride alumina in DMSO, was treated under microwaves conditions at 150° C. over 1 hour. Dichloromethane was added to the mixture reaction and then the organic layer was washed with water. Separated and dry over $Mg_2SO_4$ and concentrated to give a crude product which was purified by chromatroton silicagel rotors.
MS (ES)[M+H]$^+$: 361.1

EXAMPLE 31

3-(exo)-[2-Chloro-4-(pyridin-2-yloxy)-phenylsulfanyl]-8-methyl-8-aza-bicyclo[3.2.1]octane

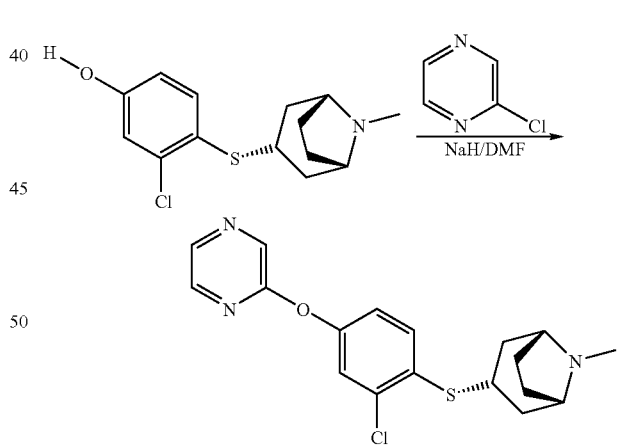

To a suspension of NaH 60% (0.020 g, 0.51 mmol) in DMF anh. (2.5 ml), 3-Chloro-4-(8-methyl-8-aza-bicyclo [3.2.1]oct-3-ylsulfanyl)-phenol (0.050 g, 0.17 mmol) was added and the mixture reaction stirred 15 min. Then 2-chloropyrazine (0.019 g, 0.17 mmol) was added and the mixture reaction was refluxed for 3 h. After cooling the mixture was treated with $CH_2Cl_2$ and washed with water and brine. The organic phase was dry over $MgSO_4$ and concentrated in vacuo. The crude was purified in silicagel to give the desired product.
MS (ES)[M+H]$^+$: 363

EXAMPLE 32

(a) 3-(exo)[2-Chloro-4-(1H-[1,2,4]triazol-3-yl-methoxy)-phenylsulfanyl]-8-methyl-8-aza-bicyclo[3.2.1]octane, bis trifluoroacetic acid salt

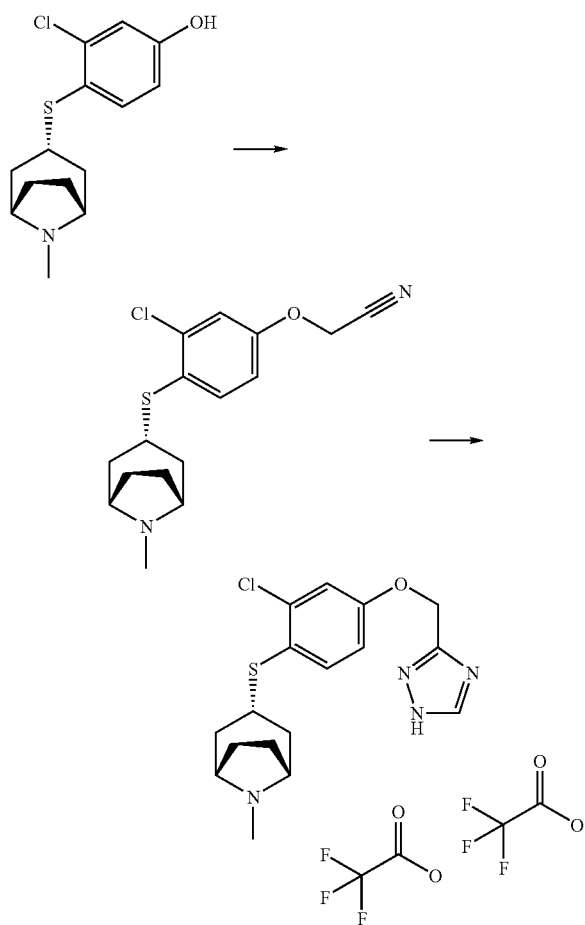

(i) [3-Chloro-4-(8-methyl-8-aza-bicyclo[3.2.1]oct-3-(exo)-ylsulfanyl)-phenoxy]-acetonitrile To a solution of phenol (XX) (1 g, 3.53 mmol) in dry dimethylformamide (34 mL) at r.t. under nitrogen, cesium carbonate (2.3 g, 7.06 mmol) was added. The mixture was stirred for 15 min and then chloroacetonitrile (0.225 mL, 3.6 mmol) was added dropwise. The reaction mixture was stirred at r.t. for 3 h and was diluted with methylene chloride. The resulting mixture was washed with water and the aqueous phase extracted with methylene chloride (×3). The combined organic phase was dried over sodium sulfate, filtered and evaporated to dryness to obtain 1.1 g (97%) of titled compound which was submitted directly to the next reaction.

EI-MS: 323 (M+1) $^1$H NMR (300 MHz, CD$_3$OD) δ (ppm) 7.55 (d, J=8.7 Hz, 1 H), 7.21 (d, J=2.8 Hz, 1 H), 7.00 (dd, J=8.7, 2.8 Hz, 1 H), 5.01 (s, 2H), 3.42 (sept, J=8.9 Hz, 1 H), 3.20 (br s, 2 H), 2.26 (s, 3H), 2.08 (m, 2 H), 1.79 (d, J=2.8 Hz, 2 H), 1.7 (d, J=2.0 Hz, 2 H), 1.64 (d, J=8.5 Hz, 2H). $^{13}$C NMR (300 MHz, CD$_3$OD) δ (ppm) 158.3, 139.6, 127.6, 117.8, 116.6, 115.2, 115.4, 62.8, 54.6, 39.8, 38.9, 38.6, 26.6.

(ii) 3-(exo)[2-Chloro-4-(1H-[1,2,4]triazol-3-yl-methoxy)-phenylsulfanyl]-8-methyl-8-aza-bicyclo[3.2.1]octane, bis trifluoroacetic acid salt To a solution of [3-Chloro-4-(exo)(8-methyl-8-aza-bicyclo[3.2.1]oct-3-ylsulfanyl)-phenoxy]-acetonitrile (0.4 g, 1.24 mmol) in methanol (0.5 mL) at 0° C. under nitrogen sodium methoxide (34 mg, 0.63 mmol) was added, the resulting mixture was stirred for 30 min at that temperature and acetic acid (0.035 mL, 0.63 mmol) and formylhydrazide (75 mg, 1.24 mmol) were successively added. The resulting mixture was stirred at r.t. for 15 min, evaporated, dissolved in dry dimethylformamide (2 mL) and heated at 115° C. for 90 min. The mixture was cooled down, diluted with methylene chloride. The resulting mixture was washed with water and the organic phase was dried over sodium sulfate, filtered and evaporated to dryness. The residue was purified by SPE to obtain 0.327 g (44%, 3 steps) of titled compound.

EI-MS: 365 (M+1) $^1$H NMR (200 MHz, CD$_3$OD) δ (ppm) 8.42 (s, 1 H), 7.55 (d, J=8.7 Hz, 1 H), 7.24 (d, J=2.6 Hz, 1 H), 7.00 (dd, J=8.7, 2.8 Hz, 1 H), 5.21 (s, 2H), 3.88 (br s, 2 H), 3.50 (sept, J=5.8 Hz, 1 H), 2.72 (s, 3H), 2.32–1.95 (m, 8 H). $^{13}$C NMR (300 MHz, CD$_3$OD)δ (ppm) 160.7, 158.4, 147.0, 140.5, 138.6, 124.1, 117.9, 115.4, 65.0, 64.0, 38.9, 37.8, 36.9, 25.1.

(b) 3-(exo)[2-chloro-4-(1H-[1,3,4]oxadiazol-2-yl-methoxy)-phenylsulfanyl]-8-methyl-8-aza-bicyclo[3.2.1]octane trifluoroacetic acid salt By proceeding in a similar manner to Example 32(a) but using ethyl bromoacetate in step (i), there was prepared 3-(exo)[2-chloro-4-(1H-[1,3,4]oxadiazol-2-ylmethoxy)-phenylsulfanyl]-8-methyl-8-aza-bicyclo[3.2.1]octane trifluoroacetic acid salt.

EXAMPLE 33

[3-Chloro-4-(8-methyl-8-aza-bicyclo[3.2.1oct-3-(exo)-ylsulfanyl)-phenoxy]-difluoro-acetic acid

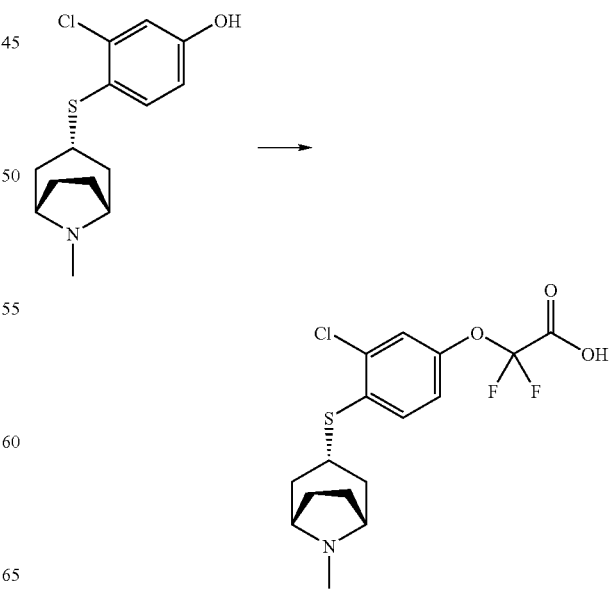

(i) [3-Chloro-4-(8-methyl-8-aza-bicyclo[3.2.1]oct-3-(exo)-ylsulfanyl)-phenoxy]-difluoro-acetic acid To a solution of phenol (XX) (1 g, 3.53 mmol) in dry dioxane (12 mL) at 0° C. under nitrogen sodium hydride (2.1 g, 88.25 mmol) and chlorodifluoroacetic acid (3 mL, 35.27 mmol) were successively added. The resulting mixture was heated at reflux for two days and cooled down to 0° C. To the cold mixture ice-water was added carefully, and the resulting mixture was evaporated in vacuo. diluted with a solution of hydrochloric acid (10%) and extracted with methylene chloride (×2). The organic phase was dried over sodium sulfate, filtered and evaporated to dryness. The residue was purified by SCX to obtain 0.433 g (32%) of titled compound.

EI-MS: 378 (M+1) $^1$H NMR (200 MHz, CD$_3$OD) δ (ppm) 7.58 (d, J=8.6 Hz, 1 H), 7.37 (d, J=2.4 Hz, 1 H), 7.19 (dd, J=8.6, 2.6 Hz, 1 H), 3.88 (br s, 2 H), 3.60 (sept, J=6.0 Hz, 1 H), 2.74 (s, 3H), 2.32–1.91 (m, 8 H). $^{13}$C NMR (300 MHz, CD$_3$OD) δ (ppm) 164.2 (d, J=34.2 Hz), 151.8, 137.9, 135.7, 128.2, 122.6, 120.2, 116.7 (t, J=450 Hz), 64.4, 38.2, 36.9, 35.2, 23.9.

EXAMPLE 34

2-[3-Chloro-4-(8-methyl-8-aza-bicyclo[3.2.1]oct-3-(exo)-ylsulfanyl)-phenoxy]-N-ethyl-acetamide, formic salt

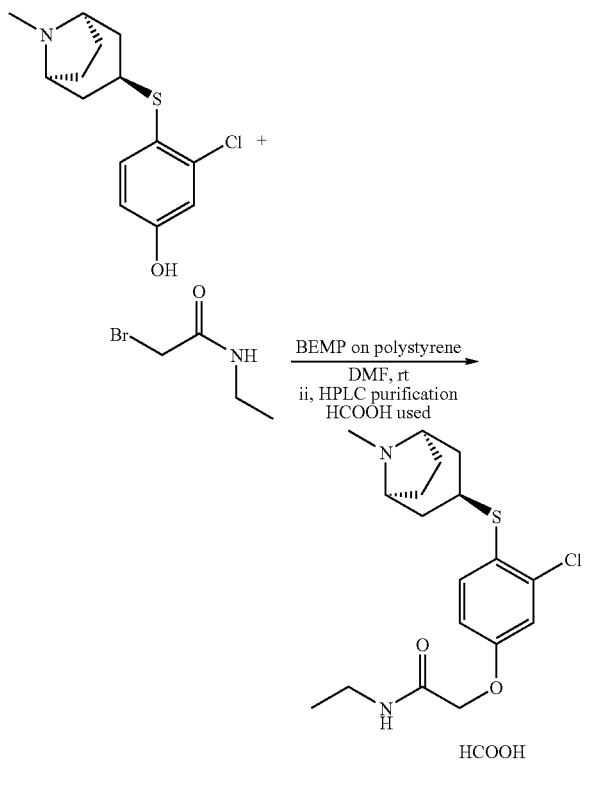

(i) 2-bromo-N-ethyl-acetamide

To a solution of ethylamide (0.056 mL, 1 mmol) plus triethylamine (0.4 mL, 2.9 mmol) in dry DCM (5 mL), bromoacetyl-bromide (0.2 mL, 2.3 mmol) was added at −78° C. under N$_2$ atmosphere (exothermic reaction). The mixture was stirred and allowed to reach room temperature until the starting material had disappeared by TLC (eluent: DCM/MeOH/NH$_4$OH drops, UV as developer, dark brown colour). The reaction was quenched with an aqueous solution of NaHCO$_3$ (5%). Both phases were stirred vigorously, and then they were separated with a column (empty cartridge) with hydrophobic resin 5 micros called FPTE (12 mL capacity). The organic layer was collected in a 13/100 tube and the solvent was evaporated in the N$_2$ stream. The residue was dissolved in dry DMF (2 mL) to have a solution of 2-bromo-N-ethyl-acetamide 0.5N to use in next step.

(ii) 2-[3-Chloro-4-(8-methyl-8-aza-bicyclo[3.2.1]oct-3-(exo)-ylsulfanyl)-phenoxy]-N-ethyl-acetamide, formic salt To a suspension of 3-Chloro-4-(8-methyl-8-aza-bicyclo[3.2.1]oct-3-ylsulfanyl)-phenol (50 mg, 0.18 mmol) plus 2-tert-butylimino-2-diethylamino-1,3-dimethylperhydro-1,3,2-diaza-phosphorine (BEMP) on polystyrene (2.2 mmol base/g) (509 mg, 1.08 mmol) in dry DMF (1 mL) in a glass vial charged with two caps and with a polystyrene frit., a solution of 2-bromo-N-ethyl-acetamide (0.5N in DMF) (0.36 mL, 0.18 mmol) made in the step i, was added at room temperature. The mixture was stirred for 16 h and checked by MS. The reaction solution was filtered and the resin was washed with MeOH several times. The combined organic fractions (DMF plus MeOH) were evaporated and the residue (45 mg) was submitted to HPLC purification (preparative LC-MS) collecting the title compound (10 mg)

MS (ES) [M+1]: 368 $^1$H NMR δ (ppm) (200 MHz, MeOD): 8.48 (br s, H—COOH, 1H), 7.55 (d, J=8.6 Hz, 1H), 7.17 (d, J=2.7 Hz, 1H), 6.93 (dd, J=2.9, 8.9 Hz, 1H), 4.49 (s, 2H), 3.82 (m, 2H), 3.49 (m, 1H), 3.28 (m, 2H), 2.69 (s, 3H), 2.30–1.90 (m, 8H), 1.12 (t, J=7.3 Hz, 3H)

Prepared in a similar fashion were prepared the formic salts of:

2-[3-Chloro-4-(8-methyl-8-aza-bicyclo[3.2.1]oct-3-(exo)-ylsulfanyl)-phenoxy]-N,N-diethyl-acetamide, 2-[3-Chloro-4-(8-methyl-8-aza-bicyclo[3.2.1]oct-3-(exo)-ylsulfanyl)-phenoxy]-N-isopropyl-acetamide, 2-[3-Chloro-4-(8-methyl-8-aza-bicyclo[3.2.1]oct-3-(exo)-ylsulfanyl)-phenoxy]-N-cyclohexyl-acetamide, N-Benzyl-2-[3-chloro-4-(8-methyl-8-aza-bicyclo[3.2.1]oct-3-(exo)-ylsulfanyl)-phenoxy]-acetamide, 2-[3-Chloro-4-(8-methyl-8-aza-bicyclo[3.2.1]oct-3-(exo)-ylsulfanyl)-phenoxy]-N-(4-fluoro-benzyl)-acetamide, 2-[3-Chloro-4-(8-methyl-8-aza-bicyclo[3.2.1]oct-3-(exo)-ylsulfanyl)-phenoxy]-N-(2,4-difluoro-benzyl)-acetamide,

EXAMPLE 35

3-(exo)-(4-Benzyloxy-2-chloro-phenylsulfanyl)-8-methyl-8-aza-bicyclo[3.2.1]octane

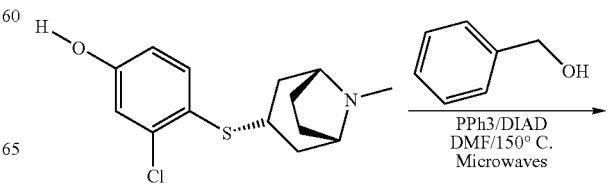

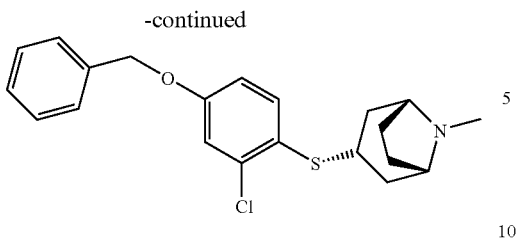

3-Chloro-4-(8-methyl-8-aza-bicyclo[3.2.1]oct-3-ylsulfanyl)-phenol (0.050 g, 0.17 mmol), PPh₃P (0.129 g, 0.49 mmol), and benzylic alcohol (0.026 ml, 0.25 mmol) were dissolved in DMF and to this solution DIAD was added (0.088 g, 0.44 mmol). The mixture reaction was treated at 150° C. under microwaves conditions over 3 hours. The mixture reaction dissolved in methanol was passed through a SCX cartridge then eluting 2M ammonia in methanol and concentrated. The material was then further purified by preparative LC-MS to provide the desired product.

MS (ES) [M+H]⁺: 374.

By this method were prepared:

3-(exo)-[2-Chloro-4-(2-trifuoromethyl-benzyloxy)-phenylsulfanyl]-8-methyl-8-aza-bicyclo[3.2.1]octane 3-(exo)-[2-Chloro-4-(3-trifuoromethyl-benzyloxy)-phenylsulfanyl]-8-methyl-8-aza-bicyclo[3.2.1]octane 3-(exo)-[2-Chloro-4-(2-methoxy-benzyloxy)-phenylsulfanyl]-8-methyl-8-aza-bicyclo[3.2.1]octane 3-(exo)-[2-Chloro-4-(3-methoxy-benzyloxy)-phenylsulfanyl]-8-methyl-8-aza-bicyclo[3.2.1]octane 3-(exo)-[2-Chloro-4-(3-fluoro-benzyloxy)-phenylsulfanyl]-8-methyl-8-aza-bicyclo[3.2.1]octane 3-(exo)-[2-Chloro-4-(3,5-difluoro-benzyloxy)-phenylsulfanyl]-8-methyl-8-aza-bicyclo[3.2.1]octane 3-(exo)-[4-(Benzo[1,3]dioxol-5-ylmethoxy)-2-chloro-phenylsulfanyl]-8-methyl-8-aza-bicyclo[3.2.1]octane 3-(exo)-[2-Chloro-4-(2,6-difluoro-benzyloxy)-phenylsulfanyl]-8-methyl-8-aza-bicyclo[3.2.1]octane 3-(exo)-[2-Chloro-4-(thiophen-2-ylmethoxy)-phenylsulfanyl]-8-methyl-8-aza-bicyclo[3.2.1]octane 3-(exo)-[2-Chloro-4-(imidazol-2-ylmethoxy)-phenylsulfanyl]-8-methyl-8-aza-bicyclo[3.2.1]octane

EXAMPLE 36

3-[3-Chloro-4-(8-methyl-8-aza-bicyclo[3.2.1]oct-3-(exo)-ylsulfanyl)-phenyl]-propionic acid, N-trifluoroacetic salt

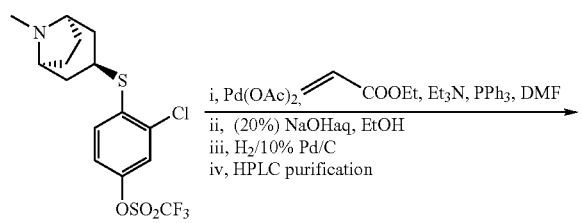

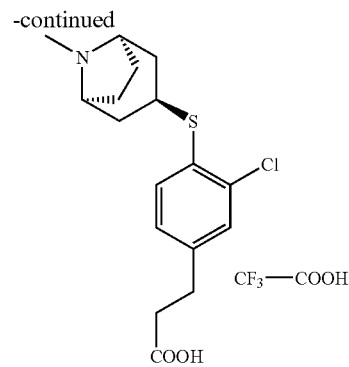

(i) 3-[3-Chloro-4-(8-methyl-8-aza-bicyclo[3.2.1]oct-3-(exo)-ylsulfanyl)-phenyl]-acrylic acid ethyl ester To a stirred solution of trifluoro-methanesulfonic acid 3-chloro-4-(8-methyl-8-aza-bicyclo[3.2.1]oct-3-ylsulfanyl)-phenyl ester (306 mg, 0.74 mmol) in dry DMF (2 mL) under N₂ atmosphere at room temperature, were secuentially added triethylamine (0.11 mL, 0.81 mmol), ethyl acrylate (0.16 mL, 1.48 mmol), triphenylphosphine (7.87 mg, 0.03 mmol) and palladium acetate (2.24 mg, 0.01 mmol). The mixture was degassed and stirred for 2 h at 100° C.

As the reaction hadn't been done by MS (ES), the duplicated quantities of the reactants were added to the reaction, degassed again, and stirred at 100° C. for 48 h. The reaction was quenched with water, and the solvent was removed in vacuo. The residue was dissolved in methanol and submitted to SCX cartridge. The ammonia fraction was submitted to a flash column chromatography on silica gel (using DCM/solution 2M NH₃ in MeOH) collecting the title compound mixed with starting material (150 mg) and 3-chloro-4-(8-methyl-8-aza-bicyclo[3.2.1]oct-3-ylsulfanyl)-phenol, product of the hydrolysis of the starting material. The mixture of starting material and the title compound was submitted to next reaction without further purification.

MS (ES) [M+1]=366

(ii) 3-[3-Chloro-4-(8-methyl-8-aza-bicyclo[3.2.1]oct-3-(exo)-ylsulfanyl)-phenyl]-acrylic acid To a solution of the intermediate from step (i) (150 mg) in ethanol (4 mL), an aqueous solution of sodium hydroxide (20%) was added at room temperature. The reaction was stirred for 16 h. The reaction was checked by MS (ES), and the starting material had been converted in the title compound. Then, the solvent was removed in vacuo, and the residue was submitted to SPE cartridge using 0.05% TFA in water/acetonitrile, collecting the title compound mixed with the 3-chloro-4-(8-methyl-8-aza-bicyclo[3.2.1]oct-3-ylsulfanyl)-phenol. (123 mg)

MS (ES) [M+1]=338

(iii) 3-[3-Chloro-4-(8-methyl-8-aza-bicyclo[3.2.1]oct-3-(exo)-ylsulfanyl)-phenyl]-propionic acid. N-trifluoroacetic salt To a solution of the intermediate from step (ii) (123 mg) in dry DMF, palladium in active carbon (10%) (820 mg) was added. The mixture was degassed and stirred under hydrogen atmosphere for 16 h. The solvent was removed in vacuo and the residue was submitted to SAX cartridge, and HPLC purification to get the title compound.

MS (ES) [M+1]: 339

EXAMPLE 37

[3-Chloro-4-(8-methyl-8-aza-bicyclo [3.2.1]oct-3-(exo)-ylsulfanyl)-phenyl]-pyridin-3-yl-amine

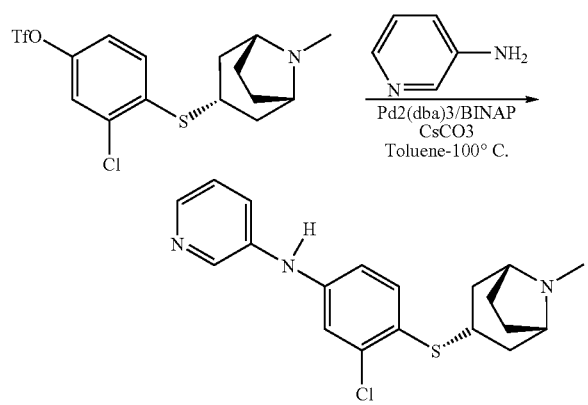

In a dry schlenk flask we charged $Pd_2(dba)_3$ (2.0 mmol/%), BINAP (2.0 mmol/%) and $CsCO_3$ (0.054 g, 0.168 mmol), evacuated and filled with Argon. Then trifluoromethanesulfonic acid 3-chloro-4-(8-methyl-8-aza-bicyclo[3.2.1]oct-3-ylsulfanyl)-phenyl ester (0.050 g, 0.12 mmol) and 3-aminopyridine (0.0135, 0.144 mmol) were added under Argon. Toulene was added to this mixture and the septum was replaced with a teflon screwcap heating the reaction at 100° C. overnight. The reaction was concentrated to dryness and purified by chromatography in $SiO_2$ ($CH_2Cl_2$/ 2M $NH_4OH$/MeOH: 9.5/0.5) to yield the desired product.

MS (ES) [M+H]⁺: 361

EXAMPLE 38

Exo-5-(8-methyl-8-aza-bicyclo[3.2.1]oct-3-ylsulfanyl)-1H-indazole

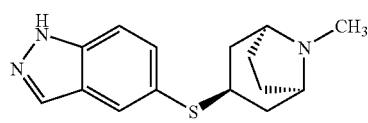

(i) 1-H-Indazole-5-thiol

5-Aminoindazole (10 g, 0.075 mol) was suspended in water (150 ml) and heated to 60° C. Concentrated HCl (26 ml) was added to form the HCl salt and the mixture stirred at 60° C. for 30 minutes before cooling to −3° C. in an ice/MeOH bath. Diazotization was performed by dropwise addition of a pre-chilled (~3° C.) solution of sodium nitrite (5.18 g, 0.075 mol) in water (75 ml), beneath the surface of the stirring solution. The temperature was maintained below 0° C. for 30 minutes. Meanwhile, potassium ethyl xanthate (18.03 g, 0.112 mol) was dissolved in water and heated to 70° C. The diazonium species was then added slowly to the hot solution and stirring continued at this temperature for 2 hours. The reaction mixture was allowed to cool then was extracted with diethyl ether (4×200 ml), washed with 2N NaOH (2×200 ml) then water (200 ml) and brine (200 ml). The organic extracts were dried ($MgSO_4$) and concentrated in vacuo to yield the xanthate as a viscous brown oil (4.96 g, 28%). The crude xanthate was slowly added as a solution in THF (125 ml) via cannula to a solution of $LiAlH_4$ (75 ml, 1M in THF, 0.075 mol) in THF (50 ml) at 0° C. Exhaust gases from this reaction were bubbled through bleach. When addition was complete, the reaction mixture was heated to reflux for 1 hour then re-cooled to 0° C. and quenched by careful addition of water (86 ml). The aluminium residues were then destroyed by addition of concentrated HCl (45 ml). The organic layer was separated and the aqueous phase was extracted with diethyl ether (3×150 ml) then the combined organic phases were dried ($MgSO_4$) and concentrated in vacuo to furnish the impure thiol as a yellow solid (2.55 g, 23% over two steps); this was used immediately without further purification; LCMS retention time ~3.09 min m/z 151.1 [(M+H)⁺, 54.6%] plus a small amount of disulfide; LCMS retention time ~4.5 min 299.0 [(M+H)⁺, 6.1%] and other impurities.

(ii) Exo-5-(8-methyl-8-aza-bicyclo[3.2.1]oct-3-ylsulfanyl)-1H-indazole

1-H-Indazole-5-thiol (1.27 g, 8.47 mmol) was stirred with CsF (1.29 g, 8.47 mmol) and ENDO-methanesulfonic acid 8-methyl-8-aza-bicyclo[3.2.1]oct-3-yl ester (2.04 g, 9.31 mmol) in DMF (15 ml) for 18 hours at room temperature. The mixture was then heated to 60° C. for a further 24 hours. The DMF was removed by washing the reaction mixture onto an SCX-2 cartridge, washing with MeOH, then eluting the product with $NH_3$/MeOH (~2M) and concentrating in vacuo. The crude material was purified by column chromatography (eluent; 5% MeOH in DCM) to furnish slightly impure product. This was further purified by trituration with $CHCl_3$/ether, which afforded the title compound as an off-white solid (77 mg, 3.3%);

$\delta_H$ (300 MHz, $CDCl_3$); 1.61–1.68 (2H, m), 1.78–1.84 (2H, m), 1.89–1.98 (2H, m), 2.02–2.10 (2H, m), 2.24 (3H, s, $NCH_3$), 3.09–3.21 (1H, m, CH), 3.25 (2H, br s, 2×CH), 7.20–7.23 (1H, m, Ar—H), 7.39–7.40 (1H, m, Ar—H), 7.89 (1H, s, Ar—H), 7.98 (1H, s, Ar—H), 11.57 (1H, br s, NH); LCMS retention time ~1.73, m/z 274.1 [(M+H)⁺, 100%].

EXAMPLE 39

Exo-5-(8-methyl-8-aza-bicyclo[3.2.1]oct-3-ylsulfanyl)-1H-indole

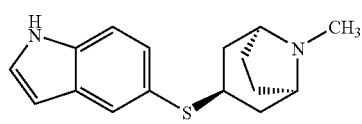

By proceeding in a similar manner to Example 38 but using 5-aminoindole there was prepared the title compound as a pale yellow solid.

$\delta_H$ (300 MHz, $CDCl_3$); 1.52–1.56 (2H, m), 1.70–1.79 (2H, m), 1.80–1.89 (2H, m), 1.95–2.05 (2H, m), 2.25 (3H, s, $NCH_3$), 3.12–3.21 (3H, m, 3×CH), 6.50 (1H, br s, Ar—H), 7.21–7.23 (1H, m, Ar—H), 7.30 (2H, s, 2×Ar—H), 7.81

(1H, s, Ar—H), 8.72 (1H, br s, NH); LCMS retention time ~2.5 min, m/z 273.1 [(M+H)$^+$, 100%].

EXAMPLE 40

Exo-5-(8-methyl-8-aza-bicyclo[3.2.1]oct-3-ylsulfanyl)-1H-benzotriazole

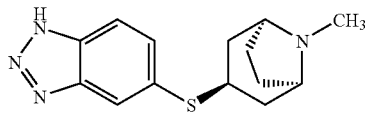

By proceeding in a similar manner to Example 38 but using 5-aminobenzotriazole there was prepared the title compound as a pale yellow solid.

$\delta_H$ (300 MHz, CDCl$_3$); 1.75–1.82 (2H, m), 1.89–2.00 (2H, m), 2.08–2.22 (4H, m), 2.37 (3H, s, NCH$_3$), 3.21–3.38 (1H, m, CH), 3.45 (2H, br s, 2×CH), 6.29 (br s, NH), 7.30–7.35 (1H, m, Ar—H), 7.60–7.64 (1H, m, Ar—H), 8.06 (1H, s, Ar—H); LCMS retention time ~1.15, m/z 275.1 [(M+H)$^+$, 100%].

EXAMPLE 41

7-Chloro-1-methyl-exo-6-(8-methyl-8-aza-bicyclo[3.2.1]oct-6-en-3-ylsulfanyl)-1,3-dihydro-benzoimidazole-2-thione

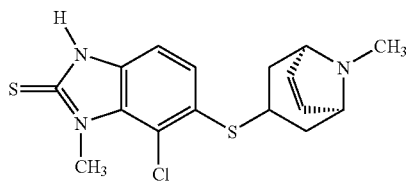

(i) ENDO-Methanesulfonic acid 8-methyl-8-aza-bicyclo[3.2.1]oct-6-en-3-yl ester Tropenol hydrochloride (15.03 g, 0.085 mol) and triethylamine (11.9 ml, 0.085 mol) in CHCl$_3$ (100 ml) were cooled to −10° C. then methanesulfonyl chloride (6.6 ml, 0.085 mol) in CHCl$_3$ (50 ml) was added dropwise. A second equivalent of MsCl (6.6 ml, 0.085 mol) was added after 2 hours and a third equivalent (6.6 ml, 0.085 mol) after 18 hours. The reaction mixture was stirred for 30 minutes after the last addition, then quenched with NH$_3$/water (2:1, 300 ml) and stirred for another 30 minutes. The solution was diluted with CHCl$_3$, then washed with water (150 ml) and brine (150 ml), dried (MgSO$_4$) and concentrated in vacuo to yield the product as a cream solid (13.48 g, 80%); $\delta_H$ (300 MHz, CDCl$_3$); 1.95–1.99 (1H, m, CH), 2.25–2.31 (5H, m, NCH$_3$, 2×CH), 2.33–2.36 (1H, m, CH), 2.94 (3H, s, SCH$_3$), 3.42 (2H, br s, 2×CH), 4.91–4.96 (1H, m, CH), 6.06 (2H, s, 2×CH);

(ii) Exo-thioacetic acid S-(8-methyl-8-aza-bicyclo[3.2.1]oct-6-en-3-yl) ester To a stirring solution of methanesulfonic acid 8-methyl-8-aza-bicyclo[3.2.1]oct-6-en-3-yl ester (7.95 g, 0.0366 mol) in THF/DMF (100 ml, 2% DMF in THF) was added potassium thioacetate (8.37 g, 0.0733 mol) and the reaction heated to reflux under nitrogen for 24 hours. Silica gel was added and the crude product was concentrated in vacuo. The resultant powder was purified by column chromatography (eluent; 5–15% MeOH in DCM). The undesired endo isomer was isolated as a brown oil (1.89 g) and the desired thioacetate was obtained as a 3:1 mix of exo:endo isomers (0.670 g), which was used without further purification; $\delta_H$ (300 MHz, CDCl$_3$) 1.62–1.67 (m, CH), 1.77–1.81 (4H, m), 2.24–2.28 (m, 4×CH$_3$), 2.47–2.57 (2H, m) 3.48 (2H, br s, 2×CH), 3.52 (2H, br s, 2×CH), 3.61–3.73 (1H, m, CH), 3.99–4.03 (1H, m, CH), 5.99 (2H, s, 2×CH), 6.03 (2H, s, 2×CH).

(iii) [2-Chloro-exo-3-(8-methyl-8-aza-bicyclo[3.2.1]oct-6-en-3-ylsulfanyl)-6-nitro-phenyl]-methylamine (2,3-Dichloro-6-nitro-phenyl)-methylamine (620 mg, 2.82 mmol) and exo-thioacetic acid S-(8-methyl-8-aza-bicyclo[3.2.1]oct-6-en-3-yl) ester (670 mg, 3.38 mmol) in ethanol (20 ml) were degassed then NaOH (2.8 ml) was added. After stirring for 1 hour the reaction mixture was separated into two portions and crudely purified by elution through an SCX-2 cartridge. The column was washed with MeOH then the product was eluted with NH$_3$/MeOH (~2M) and concentrated in vacuo. Purification of this crude material by column chromatography (eluent 0–10% MeOH in DCM) yielded the exo isomer as an orange oil (190 mg); $\delta_H$ (300 MHz, CDCl$_3$); 1.90–1.99 (4H, m, 2×CH$_2$), 2.25 (3H, s, NCH$_3$), 3.09–3.12 (3H, m, NHCH$_3$), 3.40–3.58 (3H, m, CH, 2×CH), 6.01 (2H, s, 2×CH), 6.55–6.61 (1H, m, Ar—H), 7.08 (1H, br s, NH), 7.88–7.92 (1H, m, Ar—H) and the endo isomer as an orange oil (170 mg).

(iv) 3-Chloro-N$^2$-methyl-exo-4-(8-methyl-8-aza-bicyclo[3.2.1]oct-6-en-3-ylsulfanyl)-benzene-1,2-diamine

[2-Chloro-3-(8-methyl-8-aza-bicyclo[3.2.1]oct-6-en-3-ylsulfanyl)-6-nitro-phenyl]-methyl-amine (190 mg, 0.560 mmol) and SnCl$_2$.2H$_2$O (630 mg, 2.80 mmol) were heated to between 60–70° C.; the colour of the reaction changed from orange to darker orange. Stirring was continued for 2 hours then the solution was filtered to remove a yellow precipitate, washed with NaHCO$_3$ (50 ml) and extracted with ethyl acetate (3×50 ml). The organic extracts were combined, dried (MgSO$_4$) and concentrated in vacuo to yield the crude diamine as an orange oil (86 mg, 50%) which was used without further purification; $\delta_H$ (300 MHz, CDCl$_3$); 1.62–1.74 (4H, m, 2×CH$_2$), 2.15 (3H, s, NCH$_3$), 2.61 (3H, s, NHCH$_3$), 2.92–3.06 (1H, m, CH), 3.38 (2H, br s, 2×CH), 5.81 (2H, s, 2×CH), 6.46–6.48 (1H, m, Ar—H), 7.00–7.05 (1H, m, Ar—H); LCMS retention time ~1.12 min, m/z 310.1 [(M+H)$^+$, 58%]

(v) 7-Chloro-1-methyl-exo-6-(8-methyl-8-aza-bicyclo[3.2.1]oct-6-en-3-ylsulfanyl)-1,3-dihydro-benzoimidazole-2-thione 3-Chloro-N$^2$-methyl-4-(8-methyl-8-aza-bicyclo[3.2.1]oct-6-en-3-ylsulfanyl)-benzene-1,2-diamine (86 mg, 0.278 mmol) and triethylamine (0.155 ml, 1.11 mmol) in THF (3 ml) were cooled to 0° C. and thiophosgene (0.023 ml, 0.306 mmol) was added. Stirred for 1 hour at 0° C. then the mixture was concentrated in vacuo. Purification by mass-guided preparative LCMS furnished the acetic acid salt of the product in solution. This was converted to the free base by application of this aqueous solution to an SCX-2 cartridge, washing with MeOH then elution of the product with NH$_3$/MeOH (~2M). The ammoniacal solution was concentrated in vacuo to yield the title compound as a yellow solid (42 mg, 43%); δ$_H$ (300 MHz, CDCl$_3$); 1.91–2.00 (2H, m, 2×CH), 2.10 (3H, s, NCH$_3$), 2.19–2.31 (2H, m, 2×CH), 3.01–3.15 (1H, m, CH), 3.80 (2H, br s, 2×CH), 6.02 (2H, s, 2×CH), 6.48–6.50 (1H, m, Ar—H), 7.28–7.31 (1H, m, Ar—H); LCMS retention time ~1.78 min, m/z 352.1 [(M+H)$^+$].

EXAMPLE 42

5-Chloro-6-[endo-(8-methyl-8-azabicyclo[3.2.1]oct-3-yl)thio]-1,4-dihydro-2H-3,1-benzoxazin-2-one

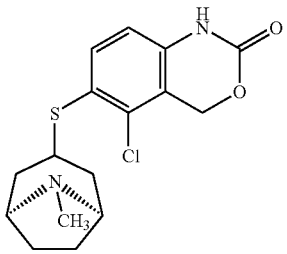

(i) Methyl-2,3-dichloro-6-nitrobenzoate

To a stirred solution of methyl-2,3-dichlorobenzoate (10 g, 48.7 mmol) in concentrated sulphuric acid (40 ml), cooled to 5° C., was added dropwise, (at such a rate to keep the reaction temperature <25° C.), concentrated nitric acid (8.4 ml, 82.9 mmol). The mixture was then stirred at ambient temperature for 2 h.

The mixture was poured slowly into water (200 ml) and stirred for 2 h. The suspension was filtered, the filter cake washed with more water on the sinter, and dried in vacuo to give the crude product as a white solid (10.3 g). The crude product was recrystallised from hexane, the crystallised solid (5-nitro isomer) removed by filtration, and the mother liquors evaporated in vacuo. The resultant white solid was recrystallised from hexane and the crystallised solid collected by filtration and dried in vacuo to give the product as a white crystalline solid (1.3 g).

(ii) Methyl-2-chloro-3-[endo-(8-methyl-8-azabicyclo[3.2.1]oct-3-yl)thio]-6-nitrobenzoate To a stirred solution of methyl-2,3-dichloro-6-nitrobenzoate (3.6 g, 14.4 mmol) in ethanol (75 ml) was added a solution of ENDO-methanesulfonic acid 8-methyl-8-azabicyclo[3.2.1]oct-3-yl ester (4.3 g, 21.6 mmol) in ethanol (75 ml) and then 2M sodium hydroxide (10.8 ml, 21.6 mmol). The mixture was stirred under nitrogen at ambient temperature for 24 h. The mixture was evaporated in vacuo to give a viscous orange oil (10.7 g).

The crude product was purified by flash chromatography (SiO$_2$; CH$_2$Cl$_2$ 5% MeOH 0.1% NH$_4$OH) to give the product as a yellow solid (3.0 g).

(iii) Methyl-6-amino-2-chloro-3-[endo-(8-methyl-8-azabicyclo[3.2.1]oct-3-yl)thio]benzoate To a stirred solution of methyl-2-chloro-3-[endo-(8-methyl-8-azabicyclo[3.2.1]oct-3-yl)thio]-6-nitrobenzoate (3.0 g, 8.1 mmol) in ethyl acetate (400 ml) was added tin chloride dihydrate (9.14 g, 40.5 mmol) and the mixture was heated under reflux for 2 h. The mixture was allowed to cool and then poured into saturated sodium bicarbonate (400 ml). The organic phase was separated and the aqueous phase extracted 2× with ethyl acetate. The combined organic phases were washed with (1) water and (2) saturated sodium chloride solution, dried (MgSO$_4$) and evaporated in vacuo to give a brown viscous oil (2.2 g). The crude product was purified by flash chromatography (SiO$_2$; CH$_2$Cl$_2$ 20% MeOH 0.1% NH$_4$OH) to give the product as a light-brown oil (1.76 g).

(iv) {6-Amino-2-chloro-3-[endo-(8-methyl-8-azabicyclo[3.2.1]oct-3-yl)thio]phenyl}methanol To a suspension of lithium aluminium hydride (180 mg, 4.7 mmol) in dry tetrahydrofuran (5 ml) was added a solution of methyl-6-amino-2-chloro-3-[endo-(8-methyl-8-azabicyclo[3.2.1]oct-3-yl)thio]benzoate (800 mg, 2.35 mmol) in tetrahydrofuran (20 ml) and the mixture stirred at ambient temperature for 4 h.

The mixture was quenched with water, filtered and the filter cake washed with ethanol. The combined filtrate and washings were evaporated in vacuo to give a yellow gum (774 mg). The crude product was purified by flash chromatography (SiO$_2$; CH$_2$Cl$_2$ 20% MeOH 0.1% NH$_4$OH) to give the product as a light-yellow oil (408 mg).

(v) 5-Chloro-6-[endo-(8-methyl-8-azabicyclo[3.2.1]oct-3-yl)thio]-1,4-dihydro-2H-3,1-benzoxazin-2-one To a solution of {6-Amino-2-chloro-3-[endo-(8-methyl-8-azabicyclo[3.2.1]oct-3-yl)thio]phenyl}methanol (372 mg, 1.2 mmol) and triethylamine (0.83 ml, 5.96 mmol) in chloroform (10 ml), cooled to −10° C., was added, dropwise, a 20% solution of phosgene in toluene (0.66 ml, 1.3 mmol). The mixture was allowed to warm to ambient temperature and stirred for 2 h. The mixture was evaporated in vacuo to give an orange solid (1.24 g). The crude product was purified by ion-exchange chromatography (SCX 500 mg pre-washed with methanol; washed with methanol and eluted with 2M methanolic ammonia); evaporation in vacuo gave a yellow oil (228 mg). Further purification by preparative mass-guide LC-MS gave the acetate of the product as a yellow oil (230 mg). Final purification by ion-exchange chromatography as above gave the free base of the title compound as a white foam (148 mg, 37%). $^1$H NMR (300 MHz; CD$_3$OD): 1.5–1.6 (2H, m, CH$_2$), 1.63–1.72 (4H, m, 2×CH$_2$), 1.9–2.0 (2H, m, CH$_2$), 2.2 (3H, s, NCH$_3$), 3.2–3.35 (3H, m, 3×CH), 4.65 (2H, s, O—CH$_2$), 6.65 (1H, d, Ar—H), 7.35 (1H, d, Ar—H). LC-MS retention time ~1.4 min, m/z (FIAPOSES) 339.1 [M+H+, 100%].

EXAMPLE 43

EXO-5-Chloro-6-(8-methyl-8-aza-bicyclo[3.2.1]oct-3-ylsulfanyl)-1H-quinolin-2-one

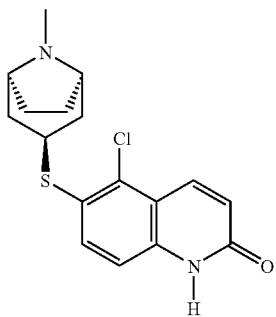

(i) 6-Chloro-5-nitroquinoline

A solution of 6-chloroquinioline (5 g, 30.6 mmol) in 30 mL cH$_2$SO$_4$ was cooled to 0° C. Sodium nitrite (70 mg, 1 mmol) was added followed by cHNO$_3$ (2.5 mL) dropwise at a rate to keep the temperature between 0° C. and 10° C. The mixture was stirred at 0° C. for 45 mins and at room temperature for 1 hour. After this time, the mixture was poured into ice and cNH$_3$ solution added until pH=7 (with cooling). The mixture was then filtered and the residue dried in vacuo to give 6-Chloro-5-nitroquinoline as an off-white solid (5.7 g, 89%); H (300 MHz; CDCl$_3$) 7.85 (1H, dd), 8.05 (1H, d), 8.25 (1H, d), 8.35 (1H, d) and 9.10 (1H, d).

(ii) 6-Chloro-5-nitroquinoline-N-oxide m-Chloroperbenzoic acid (70–75% by wt, 2.7 g, 15.6 mmol) was added in portions to a stirred, ambient temperature solution of 6-chloro-5-nitroquinoline (2 g, 9.6 mmol) in CHCl$_3$ (15 mL). The mixture was stirred for 6 h. After this time, more CHCl$_3$ was added, followed by 30 mL of a saturated aqueous solution of Na$_2$CO$_3$ and 1 mL 1M NaOH. The mixture was separated and the aqueous phase extracted with CHCl$_3$ (×2). The organic phases were combined and washed with a saturated aqueous solution of Na$_2$CO$_3$, H$_2$O and brine. The organic phase was dried (MgSO$_4$) and the solvent removed in vacuo to give 6-Chloro-5-nitroquinoline-N-oxide as a yellow solid (1.8 g, 84%); H (300 MHz; CDCl$_3$) 7.6 (1H, m), 7.7 (1H, d), 7.95 (1H, d), 8.65 (1H, d) and 8.75 (1H, d).

(iii) EXO-6-(8-Methyl-8-aza-bicyclo[3.2.1]oct-3-ylsulfanyl)-5-nitro-quinoline-N-oxide A mixture of 6-chloro-5-nitroquinoline-N-oxide (2.68 g, 11.7 mmol) and exo-thioacetic acid 8-methyl-8-aza-bicyclo[3.2.1]oct-3-yl ester (3 g, 15.1 mmol) in de-gassed MeOH (120 mL) was treated with 15 mL of 2M NaOH and stirred at room temperature under an atmosphere of nitrogen for 48 h. The solvent was removed in vacuo and the residue purified by flash column chromatography using an ISCO CombiFlash system (2×120 g column, eluent 40–50% MeOH (containing 1% NH$_3$) in CH$_2$Cl$_2$). The title compound was obtained as a yellow-brown semi-solid (90–95% pure) (2.1 g, 52%); H (300 MHz; CDCl$_3$) 1.9 (2H, m), 2.1 (2H, m), 2.3 (2H, m), 2.69 (2H, m), 3.3 (3H, s), 3.81 (2H, m), 3.99 (1H, m), 7.70 (1H, t), 7.8 (1H, d), 8.2 (1H, d), 8.7 (1H, d) and 8.8 (1H, d).

(iv) EXO-5-Amino-6-(8-methyl-8-aza-bicyclo[3.2.1]oct-3-ylsulfanyl)-quinoline-N-oxide A mixture of EXO-6-(8-Methyl-8-aza-bicyclo[3.2.1]oct-3-ylsulfanyl)-5-nitro-quinoline-N-oxide (1.9 g, 5.5 mmol) and tin (II) chloride dihydrate (7 g, 27.5 mmol) in EtOAc (200 mL) was heated under reflux for 18 h. The hot solution was filtered and the organic phase carefully washed with 33% aq NH$_3$. The residue was washed with 33% aq NH$_3$ and the aqueous phase extracted with EtOAc. The organic phases were then combined, dried (MgSO$_4$), filtered and solvent removed in vacuo to give the title compound as a bright yellow foam (550 mg, 32%); H (300 MHz; CDCl$_3$) 1.49 (2H, m), 1.70 (2H, m), 1.85 (2H m), 1.97 (2H, m), 2.24 (3H, s), 3.15 (3H, m), 5.27 (2H, bs), 7.22 (1H, t), 7.72 (2H, t), 8.04 (1H, d) and 8.48 (1H, d).

(v) EXO-5-Chloro-6-(8-methyl-8-aza-bicyclo[3.2.1]oct-3-ylsulfanyl)-quinoline-N-oxide To a stirred solution of EXO-5-Amino-6-(8-methyl-8-aza-bicyclo[3.2.1]oct-3-ylsulfanyl)-quinoline-N-oxide (500 mg, 1.6 mmol) in cHCl (4 mL) in H$_2$O (2 mL) cooled to −5° C. was added a solution of sodium nitrite (110 mg, 1.6 mmol) in H$_2$O (0.6 mL). After stirring at low temperature for 15 mins, the mixture was added to a stirred suspension of copper (I) chloride (630 mg, 6.3 mmol) in cHCl (1.3 mL) heated to 83–65° C. The combined mixture was stirred at elevated temperature for 5 mins. Ice was added and the mixture made alkaline with 10% NaOH, extracted with CHCl$_3$ (×5), washed with brine and the organic phase dried (MgSO$_4$). The solvent was removed in vacuo and the resulting residue purified by flash column chromatography using the ISCO CombiFlash system (35 g column, eluent 15–30% MeOH (containing 1% NH$_3$) in CH$_2$Cl$_2$) to give the title compound as a colourless solid (98 mg, 18%); H (300 MHz; CDCl$_3$) 1.65 (2H, m), 1.90 (4H, m), 2.12 (2H, m), 2.34 (3H, s), 3.20 (2H, m), 3.65 (1H, m), 7.35 (1H, t), 7.65 (1H, d), 8.05 (1H, d), 8.45 (1H, d) and 8.65 (1H, d).

(vi) EXO-5-Chloro-6-(8-methyl-8-aza-bicyclo[3.2.1]oct-3-ylsulfanyl)-1H-quinolin-2-one Benzoyl chloride (45 mg, 0.32 mmol) was added dropwise to a vigorously stirred two-phase mixture of EXO-5-Chloro-6-(8-methyl-8-aza-bicyclo[3.2.1]oct-3-ylsulfanyl)-quinoline-N-oxide (90 mg, 0.27 mmol) and NaOH (25 mg, 0.62 mmol) in H$_2$O (0.8 mL) and CH$_2$Cl$_2$ (0.42 mL). The reaction mixture was allowed to stir at room temperature for 1 h and then filtered. The residue was washed with CH$_2$Cl$_2$ and H$_2$O and dried in vacuo. The solid was purified by LC-MS to give the acetate salt of the title compound as a colourless solid (11.3 mg, 11%); H (300 MHz; CDCl$_3$) 2.05 (6H, m), 2.29 (2H, m), 2.65 (3H, s), 3.65 (1H, m), 3.75 (2H, m), 6.75 (1H, d), 7.35 (1H, d), 7.75 (1H, d) and 8.35 (1H, d).

EXAMPLE 44

EXO-6-(8-Methyl-8-aza-bicyclo[3.2.1]oct-3-ylsulfanyl)-1H-quinolin-2-one

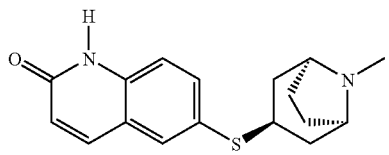

(i) 2-Oxo-1,2-dihydro-quinoline-6-sulfonyl chloride

To an ice bath cooled stirred slurry of 2-hydroxyquinoline (30.5 g, 0.210 mol) in dichloromethane (300 cm³) was added chlorosulphonic acid (70 cm³, 1.05 mol) in 4 equal sized batches. This was left to stir at room temperature for 2 days then slowly poured onto crushed ice. Large amount of a white solid formed in the lower chlorinated layer. This was filtered off and dried in vacua to yield 2-Oxo-1,2-dihydro-quinoline-6-sulfonyl chloride as a dry white solid (36.3 g); $\delta_H$ (300 MHz; D6 DMSO) 6.51–6.59 (1H, m, 1×Ar—H), 7.29–7.34 (1H, m, Ar—H), 7.71–7.79 (1H, m, Ar—H), 7.90–7.96 (1H, m, Ar—H) and 8.00–8.06 (1H, m, Ar—H); LCMS retention time ~3.43 min, m/z (FIANEG) 241.9 [Cl$^{35}$(M)$^-$, 100%] and 244.0 [Cl$^{37}$(M)$^-$, 33%]. NMR and LCMS showed that this material contained some starting material as a minor impurity but no further purification was performed.

(ii) Thioacetic acid S-(2-oxo-1,2-dihydro-quinolin-6-yl) ester

To an ice bath cooled, stirred mixture of impure 2-Oxo-1,2-dihydro-quinoline-6-sulfonyl chloride (20 g, ~82 mmol), acetic acid (240 cm³) and acetic anhydride (80 cm³) was added sodium acetate (24 g) in three equal sized batches. Then Zinc (20 g) was added in small batches (exothermic reaction). After one hour the ice bath was removed and the reaction was left stirring at room temperature for five days then concentrated in vacuo then triturated with water (~200 cm³). The solid that was formed was filtered off and dried in vacua to yield Thioacetic acid S-(2-oxo-1,2-dihydro-quinolin-6-yl) ester as a dry grey solid (11.7 g, ~65%); $\delta_H$ (300 MHz; D6 DMSO) 2.42 (3H, s, COCH$_3$), 6.51–6.57 (1H, m, Ar—H), 7.32–7.37 (1H, m, Ar—H), 7.43–7.48 (1H, m, Ar—H), 7.72 (1H, s, Ar—H), 7.88–7.92 (1H, m, Ar—H) and 11.95 (1H, br s, N—H); LCMS retention time ~3.03 min, m/z (FIAPOS) 220 [(M+H)$^+$, 100%].

(iii) EXO-6-(8-Methyl-8-aza-bicyclo[3.2.1]oct-3-ylsulfanyl)-1H-quinolin-2-one To a stirred mixture of thioacetic acid S-(2-oxo-1,2-dihydro-quinolin-6-yl) ester (3.00 g, 13.7 mmol) and ENDO-methanesulfonic acid 8-methyl-8-aza-bicyclo[3.2.1]oct-3-yl ester (2.7 g, 12.3 mmol) with 2-propanol (~150 cm³) was added pyrrolidine (1.14 cm³, 13.7 mmol) in one quick injection, at room temperature, under a flow of nitrogen gas causing a strong yellow colouration. The reaction was then treated with potassium carbonate (2.1 g, 15.2 mmol) and then heated to 80° C. The reaction was maintained at this temperature overnight then cooled to room temperature and concentrated in vacuo to a yellow paste. This was treated with 1N HCl (100 cm³) and washed with CHCl$_3$ (3×50 cm³). The aqueous layer was filtered through paper and then basified using 2N NaOH (~50 cm³), then extracted with CHCl$_3$ (3×50 cm³). The organics were dried (MgSO$_4$) and concentrated in vacuo then columned on silica (gradient elution, 98:2 to 85:15, CH$_2$Cl$_2$:methanolic ammonia) but NMR still showed some minor impurities. The solid was recrystallised by dissolving in the minimum warm (~50° C.) EtOAc and methanol (1:1, ~10 cm³), then slowly cooling to room temperature, thus yielding EXO-6-(8-Methyl-8-aza-bicyclo[3.2.1]oct-3-ylsulfanyl)-1H-quinolin-2-one (213 mg) as fine colourless crystals; $\delta_H$ (300 MHz; CDCl$_3$) 1.50–1.60 (2H, m, 2× one of CH$_2$), 1.70–1.87 (4H, m, 4× one of CH$_2$), 1.98–2.06 (2H, m, 2×one of CH$_2$), 2.21 (3H, s, NCH$_3$), 3.10–3.27 (3H, m, HCS and 2×NCH), 6.62–6.70 (1H, m, Ar—H), 7.20–7.27 (1H, m, Ar—H), 7.50–7.56 (1H, m, Ar—H), 7.62–7.64 (1H, m, Ar—H) and 7.70–7.73 (1H, m, Ar—H); LCMS retention time ~2.03 min, m/z (FIAPOSES) 301.1 [(M+H)$^+$, 100%].

EXAMPLE 45

Exo-5-[(8-methyl-8-azabicyclo[3.2.1]oct-3-yl)sulfanyl]-1,3-dihydro-2H-benzimidazol-2-one

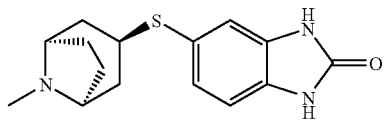

By proceeding in a similar manner to Example 44 but using 1,3-dihydro-2H-benzimidazol-2-one in place of 2-hydroxyquinoline there was prepared the title compound as colourless solid. m.p.=178.5–181.6° C.

$^1$H nmr, $\delta_H$ (300 MHz; C$_2$D$_6$SO) 1.42–1.5 (2H, m, CH$_2$), 1.60–1.65 (4H, 2×CH$_2$), 1.72–1.82 (2H, m, CH$_2$), 2.08–2.14 (3H, s, NCH$_3$), 3.00–3.05 (2H, m, NCHCH$_2$), 3.10–3.23 (1H, m, HCS), 6.87–6.89 (1H, m, Ar—H), 6.95–6.97 (1H, s, Ar—H), 7.00–7.04 (1H, m, Ar—H), 10.60–10.68 (1H, s, NH), 10.72–10.82 (1H, s, NH); LCMS retention time ~0.803 min, m/z (FIAPOSES) 290.1 [(M+H)$^+$, 97.8%].

EXAMPLE 46

Exo-6-[(8-methyl-8-azabicyclo[3.2.1]oct-3-yl)sulfanyl]-2,4-(1H,3H)-quinazolindio

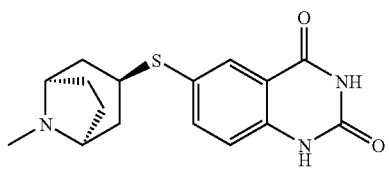

By proceeding in a similar manner to Example 44 but using 2,4-(1H,3H)-quinazolindione in place of 2-hydroxyquinoline there was prepared the title compound as colourless solid.

m.p.>260° C. $^1$H nmr, $\delta_H$ (300 MHz; C$_2$D$_6$SO) 1.60–1.78 (6H, m, 3×CH$_2$), 1.92–2.05 (2H, m, CH$_2$), 2.25–2.30 (3H, s, NCH$_3$), 3.28–3.48 (1H, m, HCS; 2H, m, NCHCH$_2$), 7.10–7.15 (1H, m, Ar—H), 7.65–7.72 (1H, m, Ar—H), 7.83–7.88 (1H, s, Ar—H), 8.24–8.35 (1H, s, HCOOH), 10.90–11.90 (2H, s, 2×NH); LCMS retention time ~0.910 min, m/z (FIAPOSES) 318.1 [(M+H)$^+$, 97.4%].

EXAMPLE 47

Exo-7-chloro-1-methyl-6-[(8-methyl-8-azabicyclo[3.2.1]oct-3-yl)sulfanyl]-1,3-dihydro-2H-benzimidazole-2-thione

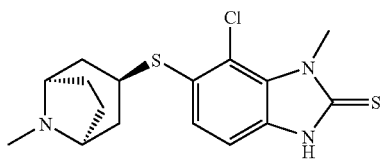

(i) 2,3-dichloro-N-methyl-6-nitroaniline 2,3-dichloro-6-nitroaniline (1.026 g, 5 mmole), was suspended in toluene (10 ml). To this vigorously stirred suspension was added 50% aqueous sodium hydroxide solution (1.7 g), tertiary-butyl ammonium chloride (0.07 g, 0.25 mmole) and dimethyl sulfate (0.51 ml, 5.4 mmole). After 4 hr stirring at room temperature the intense red solution was washed with water, brine, dried with magnesium sulfate, filtered, evaporated in vacuo. Weight=1.03 g, m.p.=82° C.

Spectra: $^1$H nmr, $\delta_H$ (300 MHz; CDCl$_3$) 2.96–3.05 (3H, d, N—CH$_3$), 6.60–6.65 (1H, d, Ar—H; 1H, m, N—H), 7.72–7.80 (1H, d, Ar—H); LCMS retention time ~5.959 min, m/z (GRADNL.M)=219.1 [(M–H)$^-$, 100%].

(ii) Exo-2-chloro-N-methyl-3-[(8-methyl-8-azabicyclo[3.2.1]oct-3-yl)sulfanyl]-6-nitroaniline 2,3-dichloro-N-methyl-6-nitroaniline (3.99 g, 18 mmole) and (8-methyl-8-azabicyclo[3.2.1]oct-3-yl)ethanethioate (4.92 g, 24.7 mmole) were stirred in ethanol (90 ml). To this was added 2M aqueous sodium hydroxide (25 ml, 50 mmole). The solution was stirred magnetically, at room temperature, for 24 hr, under a nitrogen atmosphere. The mixture was evaporated in vacuo, dissolved in chloroform, washed with water, then brine. The chloroform solution was extracted with 5M HCl, this was washed with chloroform. The acid extract was basified with aqueous 50% sodium hydroxide, and extracted into chloroform, washed with brine, dried with magnesium sulfate, filtered, evaporated in vacuo, purified by flash chromatography, using 1% ammonia-methanol:dichloromethane (0% to 10%). Weight=0.512 g of red oil, that crystallised on standing, m.p.=89° C.

Spectra: $^1$H nmr, $\delta_H$ (300 MHz; CDCl$_3$) 1.64–1.72 (2H, m, CH$_2$), 1.83–1.93 (4H, m, 2×CH$_2$), 2.08–2.14 (2H, m, CH$_2$), 2.30–2.34 (3H, s, NCH$_3$), 3.11–3.14 (3H, d, NCH$_3$) 3.21–3.24 (2H, m, NCHCH$_2$), 3.50–3.62 (1H, m, HCS), 6.62–6.65 (1H, d, Ar—H), 7.00–7.10 (1H, s, N—H), 7.90–7.92 (1H, d, Ar—H), LCMS retention time ~1.930 min, m/z (GRADNL.M)=342.1 [(M–H)$^+$, 100%]

(iii) Exo-3-chloro-N$^2$-methyl-4-[(8-methyl-8-azabicyclo[3.2.1]oct-3-yl)sulfanyl]-benzenediamine Exo-2-chloro-N-methyl-3-[(8-methyl-8-azabicyclo[3.2.1]oct-3-yl)sulfanyl]-6-nitroaniline (0.512 g, 1.5 mmole) was dissolved in ethyl acetate (20 ml), and to this was added SnCl$_4$.2H$_2$O (1.69 g, 7.5 mmole). The stirred mixture was brought to reflux, under a nitrogen atmosphere, and held at this temperature for 20 min. The supernatent liquid of the cooled solution was added to an acid ion-exchange solid phase contained in a cartridge (10 g, SCX-2). A gum that remained in the flask was repeatedly extracted into ethyl acetate, and this was also added to the cartridge. The cartridge was washed with ethyl acetate, then methanol. The product was stripped off the cartridge using 2M NH$_3$ in methanol. The fractions containing product were combined, re-filtered to remove residual tin residues, evaporated in vacuo. Weight of solid (broad m.p.),=0.471 g. Spectra: $^1$H nmr, $\delta_H$ (300 MHz; CD$_3$OD) 1.92–2.95 (6H, m, 3×CH$_2$), 2.22–2.34 (2H, m, CH$_2$), 2.65–2.70 (3H, s, NCH$_3$), 2.75–2.77 (3H, broad singlet, NCH$_3$), 3.34–3.50 (1H, m, HCS), 3.85 –3.92 (2H, m, NCHCH$_2$), 6.64–6.70 (1H, d, Ar—H), 7.12–7.15 (1H, d, Ar—H), LCMS retention time ~1.223 min, m/z (GRADNL.M)=312.1 [(M–H)$^+$, 100%]. Similarly prepared were: Exo-3-chloro-N$^2$-propyl-4-[(8-methyl-8-azabicyclo[3.2.1]oct-3-yl)sulfanyl]-benzenediamine (an oil), m/z (GRADNL.M)=340.1, and Exo-3-chloro-N$^2$-isopropyl-4-[(8-methyl-8-azabicyclo[3.2.1]oct-3-yl)sulfanyl]-benzenediamine (an oil),), m/z (GRADNL.M)=340.1

(iv) Exo-7-chloro-1-methyl-6-[(8-methyl-8-azabicyclo[3.2.1]oct-3-yl)sulfanyl]-1,3-dihydro-2H-benzimidazole-2-thione Exo-3-chloro-N$^2$-methyl-4-[(8-methyl-8-azabicyclo[3.2.1]oct-3-yl)sulfanyl]-benzenediami (0.475 g, 1.52 mmole) was dissolved in THF (15 ml) and DMF (15 ml). Triethylamine (0.86 ml, 6.16 mmole) was added and the solution was cooled to 0° C. in an ice-water bath. Thiophosgene (0.134 ml, 1.76 mmole) was dissolved in THF (10 ml) and added, with stirring, dropwise, to the solution of the benzendiamine, at such a rate that the temperature did not exceed 10° C. On completion of addition the mixture was stirred at ambient temperature for 1 hr. The mixture was evaporated in vacuo, the residue was dissolved in water, if necessary using a few drops of acetic acid to aid solubilisation. This solution was added to an acid ion-exchange resin contained in a cartridge (10 g, SCX-2), the cartridge was washed through with water, then methanol. The product could be stripped off using 2M-NH$_3$ in methanol. Fractions containing product were bulked, evaporated, and purified by flash chromatography using florisil as stationary phase and gradient elution with methanol: chloroform (2% to 10%). Weight=0.0494 g, m.p.=217.3–219.1° C.

Spectra: $^1$H nmr, $\delta_H$ (300 MHz; CDCl$_3$) 1.70–1.88 (2H, m, CH$_2$), 1.92–1.98 (2H, m, CH$_2$), 2.06–2.35 (4H, m, 2×CH$_2$; 3H, s, NCH$_3$), 3.10–3.24 (1H, m, HCS), 3.45–3.52 (2H, m, NCHCH$_2$), 4.10–4.14 (3H, s, NCH$_3$), 6.50–6.52 (1H, s, Ar—H), 7.22–7.25 (1H, s, Ar—H), LCMS retention time ~2.603 min, m/z (FIAPOSES)=354.1 [(M+H)$^+$, 98.6%].

EXAMPLE 48

Exo-7-chloro-1-propyl-6-[(8-methyl-8-azabicyclo[3.2.1]oct-3-yl)sulfanyl]-1,3-dihydro-2H-benzimidazole-2-thione

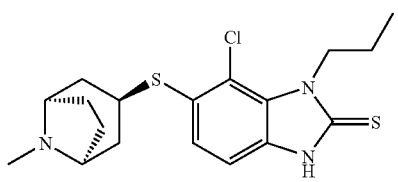

By proceeding in a similar manner to Example 47 there was prepared the title compound as colourless solid. m.p.=131.4–133.9° C.

$^1$H nmr, $\delta_H$ (300 MHz; CDCl$_3$) 1.00–1.06 (3H, m, CH$_3$), 1.08–1.22 (2H, m, CH$_2$), 1.70–2.12 (8H, m, 4×CH$_2$), 2.20–2.22 (3H, s, NCH$_3$), 3.14–3.25 (1H, m, HCS), 3.38–3.42 (2H, m, NCHCH$_2$), 4.52–4.58 (2H, m, CH$_2$), 6.70–6.72 (1H, s, Ar—H), 7.25–7.30 (1H, s, N—H; 1H, s, Ar—H), LCMS retention time ~2.291 min, m/z (FIAPOSES) 382.1 [(M+H)$^+$, 100%]

EXAMPLE 49

Exo-7chloro-1-isopropyl-6-[(8-methyl-8-azabicyclo[3.2.1]oct-3-yl)sulfanyl]-1,3-dihydro-2H-benzimidazole-2-thione

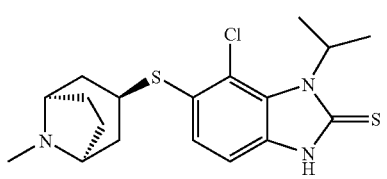

By proceeding in a similar manner to Example 47 there was prepared the title compound as colourless solid. m.p.=228.9–230.9° C. Spectra: $^1$H nmr, $\delta_H$ (300 MHz; CDCl$_3$) 1.58–1.60 (6H, d, 2×CH$_3$), 1.72–2.08 (8H, m, 4×CH$_2$), 2.28–2.30 (3H, s, NCH$_3$), 3.23–3.40 (2H, m, NCHCH$_2$H; 1H, m, HCS), 5.48–5.60 (1H, m, C—H), 7.17–7.19 (1H, s, Ar—H), 7.42–7.48(1H, s, Ar—H), LCMS retention time ~2.115 min, m/z (FIAPOSES)=382.1 [(M+H)$^+$, 98.2%]

EXAMPLE 50

Exo-7-chloro-1-methyl-6-[(8-methyl-8-azabicyclo[3.2.1]oct-3-yl)sulfanyl]-1,3-dihydro-2H-benzimidazol-2-one hydrochloride

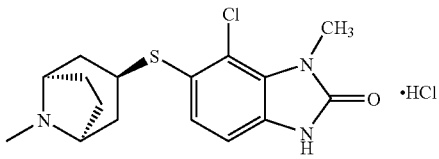

Exo-3-chloro-N$^2$-methyl-4-[(8-methyl-8-azabicyclo[3.2.1]oct-3-yl)sulfanyl]-benzenediamine [Example 46 (iii), 0.471 g, 1.51 mmole], was dissolved in a mixture of THF (20 ml) and DMF (20 ml). To this was added triethylamine (0.86 ml, 6.16 mmole), and the mixture was cooled to 0° C. in an ice-water bath. A 20% phosgene in toluene solution was added, dropwise, to this stirred solution, at a rate that the temperature never exceeded 10° C. The solution was allowed to stir at ambient temperature for 1 hr, the mixture was then evaporated in vacuo. The residue was dissolved in water (a few drops of acetic acid were added to facilitate solubilisation), and added to an acid ion-exchange polymer in a cartridge (10 g, SCX-2). The cartridge was washed with water, then methanol, the product was stripped off using 2M NH$_3$ in methanol. Fractions containing product were bulked, evaporated, purified by flash chromatography, gradient elution using ammoniamethanol:dichloromethane (0% to 12.5%). Fractions containing product were bulked, dissolved in chloroform, and enough ethereal HCl was added such that the solution was acid by pH paper. The solution was evaporated to dryness, triturated with dry ether, filtered, dried. Weight=0.0879 g, m.p. >260° C. Spectra: $^1$H nmr, □H (300 MHz; CD$_3$OD) 1.95–2.40 (8H, m, 4×CH$_3$), 2.70–2.80 (3H, s, NCH$_3$), 3.42–3.55 (1H, m, HCS), 3.72–3.75 (3H, s, NCH$_3$), 3.86–3.92 (2H, m, NCHCH$_2$H) 6.99–7.20 (1H, s, Ar—H), 7.36–7.42 (1H, s, Ar—H), LCMS retention time ~1.468 min, m/z (FIAPOSES)=338.1 [(M+H)$^+$, 100%]

EXAMPLE 51

Exo-5-chloro-1-methyl-6-[(8-methyl-8-azabicyclo[3.2.1]oct-3-yl)sulfanyl]-1,3-dihydro-2H-benzimidazol-2-one

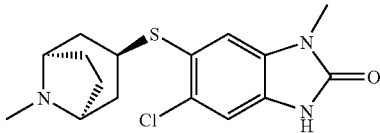

By proceeding in a similar manner to examples 47 and 50 but using 3,4-dichloro-N-methyl-6-nitroaniline there was prepared the title compound as a colourless solid. m.p.=206.4–207.2° C.

$^1$H nmr, $\delta_H$ (300 MHz; CDCl$_3$) 1.63–1.73 (2H, m, CH$_2$), 1.90–1.96 (4H, 2×CH$_2$), 2.04–2.10 (2H, m, CH$_2$), 2.10–2.14 (3H, s, NCH$_3$), 3.11–3.20 (1H, m, HCS), 3.12–3.25 (2H, m, NCHCH$_2$),3.25–3.35 (3H, s, NCH$_3$), 6.75–6.78 (1H, s, Ar—H), 7.05–7.08 (1H, s, Ar—H), 12.05–12.95 (1H, s, NH); LCMS retention time ~1.966 min, m/z (FIAPOSES) 338.1 [(M+H)$^+$, 100%].

EXAMPLE 52

EXO-5-Chloro-6-(8-methyl-8-aza-bicyclo[3.2.1]oct-3-ylsulfanyl)-3H-benzooxazol-2-one hydrochloride salt

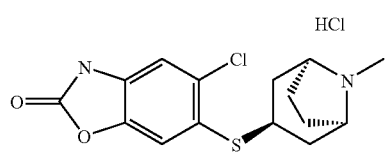

(i) 5-Chloro-2-oxo-2,3-dihydro-benzooxazole-6-sulfonic acid

To a stirred mixture of chlorzoxazone (10 g, 58.9 mmol) and CH$_2$Cl$_2$ (~500 cm$^3$) was added chlorosulphonic acid (4.3 cm$^3$, 64.8 mmol) at room temperature. The reaction was left at room temperature for a week whereupon all the solvent had evaporated leaving a white solid. NMR showed a 1:2 mixture of product and starting material respectively. This crude was extracted with H$_2$O (3×15 cm$^3$), then the aqueous was concentrated in vacuo to a sticky solid which was washed with CH$_2$Cl$_2$ (4×40 cm$^3$) to yield 5-Chloro-2-oxo-2,3-dihydro-benzooxazole-6-sulfonic acid as a fine white solid; δ$_H$ (300 MHz; D6 DMSO) 7.10 (1H, s, Ar—H), 7.68 (1H, s, Ar—H) and 11.80 (1H, s, N—H); LCMS retention time ~0.47 min, m/z (FIANEG) 247.9 [Cl$^{35}$ (M–H)$^-$, 100%] and 249.9 [Cl$^{37}$ (M–H)$^-$, 33%].

(ii) 5-Chloro-2-oxo-2,3-dihydro-benzooxazole-6-sulfonyl chloride

To a stirred mixture of 5-Chloro-2-oxo-2,3-dihydro-benzooxazole-6-sulfonic acid (~10 g, 40 mmol) and CH$_2$Cl$_2$ was added thionyl chloride (5.8 cm$^3$, 80 mmol) at room temperature, causing gas to be evolved. This was stirred at room temperature for two hours but the solid didn't dissolve and FIA only showed starting material. Therefore a few drops of DMF were added and the reaction heated to 50° C. overnight but no reaction occurred. The starting material was filtered off and then treated with neat thionyl chloride (15 cm$^3$) and heated to 70° C. overnight, FIA now detected starting material and product, so the reaction was treated with DMF (2×1 cm$^3$) to aid solvation, FIA showed completion of the reaction. The reaction was diluted with CH$_2$Cl$_2$ (100 cm$^3$) then poured onto ice. The solid formed was filtered off and dried in vacuo yielding 5-Chloro-2-oxo-2,3-dihydro-benzooxazole-6-sulfonyl chloride (4.6 g, 43%) as a fine white solid; δ$_H$ (300 MHz; D6 DMSO) 7.09 (1H, s, Ar—H), 7.69 (1H, s, Ar—H) and 11.81 (1H, s, N—H); m/z (FIANEG) 266.0 [(M–H)$^-$, 100%] and 268.0 [(M–H)$^-$, 67%].

(iii) Thioacetic acid S-(3-acetyl-5-chloro-2-oxo-2,3-dihydro-benzooxazol-6-yl) ester To an ice bath cooled stirred solution of 5-Chloro-2-oxo-2,3-dihydro-benzooxazole-6-sulfonyl chloride (4.6 g, 17.2 mmol) in acetic acid (60 cm$^3$) and acetic anhydride (20 cm$^3$) was added sodium acetate (8 g). This mixture was treated with zinc (5×1 g) in batches due to the strongly exothermic reaction. This was stirred at room temperature overnight to give a pale grey slurry. The reaction was concentrated in vacuo then treated with H$_2$O.

The solid was filtered off and washed with more H$_2$O then dried in vacuo to yield thioacetic acid S-(3-acetyl-5-chloro-2-oxo-2,3-dihydro-benzooxazol-6-yl) ester as a a grey solid (4.4 g, 90%); δ$_H$ (300 MHz; D6 DMSO) 2.48 (3H, s, COCH$_3$), 2.60 (3H, s, COCH$_3$), 7.72 (1H, s, Ar—H) and 8.08 (1H, s, Ar—H); LCMS retention time ~4.86 min.

(iv) EXO-5-Chloro-6-(8-methyl-8-aza-bicyclo[3.2.1]oct-3-ylsulfanyl)-3H-benzooxazol-2-one hydrochloride salt To a stirred mixture of thioacetic acid S-(3-acetyl-5-chloro-2-oxo-2,3-dihydrobenzooxazol-6-yl) ester (2.00 g, 6.98 mmol), ENDO-methanesulfonic acid 8-methyl-8-aza-bicyclo[3.2.1]oct-3-yl ester (1.53 g, 6.98 mmol) and cesium fluoride (1.05 g, 6.98 mmol) in DMF was added pyrrolidine (1.17 cm$^3$, 14.0 mmol) in one quick injection, at 80° C., under a flow of nitrogen gas. The reaction was maintained at this temperature overnight then treated with acetic anhydride (1 cm$^3$) and concentrated in vacuo to a sticky oil. This was purified using SCX powder to yield a thick brown oil which was triturated with CH$_2$Cl$_2$ and diethyl ether to yield a very insoluble powder. This powder was stirred for two days in 0.5N HCl$_{(aq)}$ and then treated with methanol. Not all of the solid would dissolve so the mother liquor was filtered and concentrated in vacuo to yield EXO-5-Chloro-6-(8-methyl-8-aza-bicyclo[3.2.1]oct-3-ylsulfanyl)-3H-benzooxazol-2-one hydrochloride salt (48 mg) as a pale yellow solid; bH (300 MHz; D4 methanol) 1.81–2.27 (8H, m, 4×CH$_2$), 2.62 (3H, s, NCH$_3$), 3.41–3.59 (1H, m, HCS), 3.75–3.85 (2H, m, 2×NCH), 7.25 (1H, s, Ar—H) and 7.43 (1H, s, Ar—H); LCMS retention time ~2.10 min, m/z (FIAPOSES) 325.0 [Cl$^{35}$ (M+H)$^+$, 100%] and 327.0 [Cl$^{37}$ (M+H)$^+$, 33%].

EXAMPLE 53

EXO-7-Chloro-6-(8-methyl-8-aza-bicyclo[3.2.1]oct-3-ylsulfanyl)-3H-benzooxazol-2-one hydrochloride salt

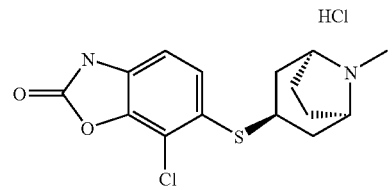

(i) 2-Chloro-3-fluoro-6-nitro-phenol

2-Chloro-3-fluoro-6-nitro-phenol (3 g, 15.7 mmol) was prepared using a literature procedure from 2-Chloro-1,3-difluoro-4-nitro-benzene. (Hayakawa, Isao; Hiramitsu, Tokiyuki; Tanaka, Yoshiaki; Chem. Pharm. Bull.; 32; 12; 1984; 4907–4913);

(ii) EXO-2-Chloro-3-(8-methyl-8-aza-bicyclo[3.2.1]oct-3-ylsulfanyl)-6-nitro-phenol To a stirred solution of 2-Chloro-3-difluoro-6-nitro-phenol (3 g, 15.7 mmol) and EXO-Thioacetic acid S-(8-methyl-8-aza-bicyclo[3.2.1]oct-3-yl) ester (4.8 g, 24.1 mmol) in ethanol (100 cm³) was added 2N NaOH (2×12 cm³) at room temperature under a flow of nitrogen gas. The reaction was stirred at room temperature overnight then concentrated in vacuo, diluted with H₂O (50 cm³) then treated with 2N HCl causing rapid formation of solid. This solid was washed with 2N HCl$_{(aq)}$, CHCl₃ and methanol to yield EXO-2-Chloro-3-(8-methyl-8-aza-bicyclo[3.2.1]oct-3-ylsulfanyl)-6-nitro-phenol (966 mg, 19%) as a fine yellow solid; $\delta_H$ (300 MHz; D6 DMSO) 2.09–2.34 (8H, m, 4×CH₂), 2.50 (3H, s, NCH₃), 3.80–4.03 (3H, m, SCH and 2×NCH), 7.15–7.29 (1H, m, Ar—H) and 7.88–7.99 (1H, m, Ar—H); LCMC retention ~2.75min, m/z (FIAPOS) 329.1 [Cl³⁵ (M+H)⁺, 100%] and 331.0 [Cl³⁷ (M+H)⁺, 33%].

(iii) EXO-6-Amino-2-chloro-3-(8-methyl-8-aza-bicyclo[3.2.1]oct-3-ylsulfanyl)-phenol hydrochloride salt A slurry of EXO-2-Chloro-3-(8-methyl-8-aza-bicyclo[3.2.1]oct-3-ylsulfanyl)-6-nitrophenol (1.67 g, 5.11 mmol) in methanol was treated with ethanolic HCl and then water to try to aid solvation but solid still remained. His mixture was added to a cooled slurry of 5% Pd/C (400 mg) with ethanol. This mixture was placed under a pressurised atmosphere of hydrogen gas (60 PSI) at room temperature for one hour. The organic solid had dissolved leaving the undissolved palladium on charcoal. The reaction was filtered through celite® then concentrated in vacuo to yield EXO-6-Amino-2-chloro-3-(8-methyl-8-aza-bicyclo[3.2.1]oct-3-ylsulfanyl)-phenol hydrochloride salt (1.55 g, 91%) as a white crystalline solid; $\delta_H$ (300 MHz; D4 methanol) 2.10–2.51 (8H, m, 4×CH₂), 2.79 (3H, s, NCH₃), 3.79–3.92 (1H, m, SCH), 4.02–4.10 (2H, m, 2×NCH), 7.25–7.32 (1H, m, Ar—H) and 7.37–7.43 (1H, m, Ar—H); LCMC retention ~0.92 min, m/z (FIAPOS) 150.1 [Cl³⁵ (M+2H)²⁺, 90%], 151.1 [Cl³⁷ (M+2H)²⁺, 30%], 299.1 [Cl³⁵ (M+H)⁺, 100%] and 301.1 [Cl³⁷ (M+H)⁺, 33%].

(iv) EXO-7-Chloro-6-(8-methyl-8-aza-bicyclo[3.2.1]oct-3-ylsulfanyl)-3H-benzooxazol-2-one hydrochloride salt To a stirred solution EXO-6-Amino-2-chloro-3-(8-methyl-8-aza-bicyclo[3.2.1]oct-3-ylsulfanyl)-phenol hydrochloride salt (506 mg, 1.7 mmol) and triethylamine (684 mg, 6.8 mmol) in CHCl₃ (30 cm³) was added a solution of triphosgene (167 mg, 0.56 mmol) as a solution in CHCl₃ (3×2 cm³) causing an exothermic reaction. The reaction was concentrated in vacuo to a greyish brown solid which was washed with methanol (3×10 cm³) to yield a brown solution and a sticky grey paste. The solid was dried in vacuo overnight then dissolved in a mixture of methanol (100 cm³) and CHCl₃ (5 cm³) and treated with a few drops of ethanolic HCl solution. This solution was concentrated in vacuo to yield EXO-7-Chloro-6-(8-methyl-8-aza-bicyclo[3.2.1]oct-3-ylsulfanyl)-3H-benzooxazol-2-one hydrochloride salt (160 mg) as a fluffy white solid; $\delta_H$ (300 MHz; D4 methanol) 1.82–2.26 (8H, m, 4×CH₂), 2.65 (3H, s, NCH₃), 3.35–3.49 (1H, m, HCS), 3.72–3.83 (2H, m, 2×NCH), 6.90–7.01 (1H, m, Ar—H) and 7.39–7.46 (1H, m, Ar—H); LCMS retention time ~2.62 min, m/z (FIAPOSES) 325.0 [Cl³⁵ (M+H)⁺, 100%] and 327.0 [Cl³⁷ (M+H)⁺, 33%].

EXAMPLE 54

EXO-7-Chloro-6-(8-methyl-8-aza-bicyclo[3.2.1]oct-3-ylsulfanyl)-3H-benzooxazole-2-thione

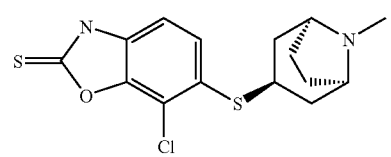

To a stirred solution EXO-6-Amino-2-chloro-3-(8-methyl-8-aza-bicyclo[3.2.1]oct-3-ylsulfanyl)-phenol hydrochloride salt (Example 16 (iii), 250 mg, 0.84 mmol) and triethylamine (338 mg, 3.4 mmol) in CHCl₃ (30 cm³) was added a solution of thiophosgene (115 mg, 1.00 mmol) as a solution in CHCl₃ (3 cm³). After stirring at room temperature for one hour the reaction was loaded onto a 10 g SCX-2 cartridge, washed with methanol then extracted using methanolic ammonia (~2N). The basic eluant was concentrated in vacuo to a brown solid which was washed with CHCl₃ (2×5 cm³) and methanol (2×2 cm³) to yield EXO-7-Chloro-6-(8-methyl-8-aza-bicyclo[3.2.1]oct-3-ylsulfanyl)-3H-benzooxazole-2-thione (136 mg, 48%) as a pale brown solid; $\delta_H$ (300 MHz; D6 DMSO) 1.79–1.99 (6H, m, 6×one of CH₂), 2.14–2.19 (2H, m, 2×one of CH₂), 2.53 (3H, s, NCH₃), 3.28–3.50 (1H, m, HCS), 3.72–3.86 (2H, m, 2×NCH), 6.92–7.0 (1H, m, Ar—H) and 7.20–7.28 (1H, m, Ar—H); LCMS retention time ~2.83 min, m/z (FIAPOSES) 341.0 [Cl³⁵ (M+H)⁺, 100%] and 343.0 [Cl³⁷ (M+H)⁺, 33%].

EXAMPLE 55

EXO-5-Chloro-3-methyl-6-(8-methyl-8-aza-bicyclo[3.2.1]oct-3-ylsulfanyl)-1H-quinazoline-2,4-dione

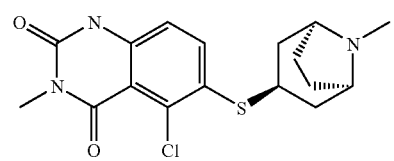

By proceeding in a similar manner to Example 41 but using N-methyl-2,3-dichlorobenzene-carboxamide in step (i) and omitting step (iv), there was prepared the title compound as a colourless solid. $\delta_H$ (300 MHz; CDCl₃) 1.52–1.61 (2H, m, 2×one of CH₂), 1.69–1.91 (4H, m, 4×one of CH₂), 1.99–2.09 (2H, m, 2×one of CH₂), 2.25 (3H, s, CHNCH₃), 3.17–3.22 (2H, m, 2×NCH), 3.30–3.49 (4H, m, CONCH₃ and SCH), 7.84–6.92 (1H, m, Ar—H) and 7.61–7.70 (1H, m, Ar—H); LCMS retention time ~1.37 min, m/z (FIAPOSES) 366.1 [Cl³⁵ (M+H)⁺, 100%] and 368.1 [Cl³⁷ (M+H)⁺, 33%].

EXAMPLE 56

EX)-4-Chloro-5-(8-methyl-8-aza-bicyclo[3.2.1]oct-3-ylsulfanyl)-1H-indazole

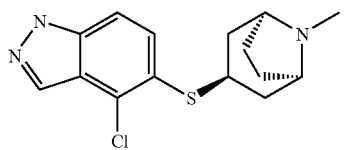

(i) 1,2-Dichloro-3-methyl4-nitro-benzene

The title compound was prepared according to the procedure described in patent application EP 0778 258 A2 (Example 1). The crude mixture of products and starting material was purified using Flash Chromatography on silica (eluant=hexane). Yielding a 10:1 mixture of 1,2-Dichloro-3-methyl4-nitro-benzene {$\delta_H$ (300 MHz; CDCl$_3$) 7.41–7.50 (1H, m, Ar—H) and 7.65–7.71 (1H, m, Ar—H); LCMC retention ~6.42 min} and 2,3-Dichloro-1-methyl4-nitro-benzene{$\delta_H$ (300 MHz; CDCl$_3$) 8.01–8.08 (1H, m, Ar—H) and 8.17–8.21 (1H, m, Ar—H); LCMC retention ~6.57 min} as a waxy solid.

(ii) EXO-3-(2-Chloro-3-methyl4-nitro-phenylsulfanyl)-8-methyl-8-aza-bicyclo[3.2.1]octane To a stirred solution of 1,2-Dichloro-3-methyl4-nitro-benzene (300 mg, 1.45 mmol) and EXO-Thioacetic acid S-(8-methyl-8-aza-bicyclo[3.2.1]oct-3-yl) ester (376 mg, 1.89 mmol) in ethanol was added 2N NaOH (~2 cm$^3$) at room temperature under a flow of nitrogen gas. The reaction was stirred at room temperature overnight then treated with 2N HCl (2 cm$^3$) to reach pH~5 then concentrated in vacuo onto silica and columned using gradient elution (98:2 to 85:15 CH$_2$Cl$_2$:methanolic ammonia) yielding EXO-3-(2-Chloro-3-methyl-4-nitro-phenylsulfanyl)-8-methyl-8-aza-bicyclo[3.2.1]octane (~150 mg) as a crystalline solid; $\delta_H$ (300 MHz; CDCl$_3$) 1.62–1.71 (2H, m, 2×one of CH$_2$), 1.87–1.97 (4H, m, 4×one of CH$_2$), 2.09–2.19 (2H, m, 2×one of CH$_2$), 2.31 (3H, s, CH$_3$), 2.60 (3H, S, CH$_3$), 3.21–3.28 (2H, m, 2×NCH), 3.50–3.61 (1H, m SCH), 7.12–7.20 (1H, m, Ar—H) and 7.70–7.79 (1H, m, Ar—H); LCMC retention ~3.56 min, m/z (FIAPOS) 327.1 [Cl$^{35}$ (M+H)$^+$, 100%] and 329.1 [Cl$^{37}$ (M+H)$^+$, 33%].

(iii) EXO-3-Chloro-2-methyl-4-(8-methyl-8-aza-bicyclo[3.2.1]oct-3-ylsulfanyl)-phenylamine To a slurry of 5% Pd on charcoal (145 mg) and ethanol was added a solution of EXO-3-(2-Chloro-3-methyl-4-nitro-phenylsulfanyl)-8-methyl-8-aza-bicyclo[3.2.1]octane (145 mg, 0.44 mmol) in ethanol. This mixture was placed under a pressurised atmosphere of hydrogen gas (60 PSI) at room temperature for 90 minutes. The reaction was filtered through celite® then concentrated in vacuo to yield EXO-3-Chloro-2-methyl4-(8-methyl-8-aza-bicyclo[3.2.1]oct-3-ylsulfanyl)-phenylamine (77 mg); $\delta_H$ (300 MHz; CDCl$_3$) 1.50–1.59 (2H, m, 2×one of CH$_2$), 1.60–1.71 (2H, m, 2×one of CH$_2$), 1.73–189 (2H, m, 2×one of CH$_2$), 1.93–2.01 (2H, m, 2×one of CH$_2$), 2.24 (3H, s, CH$_3$), 2.30 (3H, CH$_3$), 3.14–3.31 (3H, m, SCH and 2×NCH), 6.47–6.54 (1H, m, Ar—H) and 7.16–7.22 (1H, m, Ar—H);

(iv) EXO$_4$-Chloro-5-(8-methyl-8-aza-bicyclo[3.2.1]oct-3-ylsulfanyl)-1H-indazole To a stirred solution EXO-3-Chloro-2-methyl4-(8-methyl-8-aza-bicyclo[3.2.1]oct-3-ylsulfanyl)-phenylamine (1.1 g, 3.7 mmol) in HBF$_{4(aq)}$ (48% solution in H$_2$O) (2.5 cm$^3$) was added NaNO$_2$ (256 mg, 3.7 mmol) as a solution in H$_2$O at room temperature. The reaction changed colour from orange/yellow to blue/green. After one hour the reaction was filtered to yield a sticky pale green solid which was washed with water then CHCl$_3$ and then dried in vacuo. This solid was treated with CHCl$_3$ and 18-crown-6 ether (catalytic amount) and then Potassium acetate (727 mg, 7.4 mmol) was added causing a colour change from green to reddish orange with a sticky insoluble gum. The solution was purified using Flash chromatography {gradient elution (98:2 to 85:15 CH$_2$Cl$_2$:methanolic ammonia)} yielding EXO$_4$-Chloro-5-(8-methyl-8-aza-bicyclo[3.2.1]oct-3-ylsulfanyl)-1H-indazole (510 mg) as a reddish brown dry foam; $\delta_H$ (300 MHz; CDCl$_3$) 1.56–1.70 (2H, m, 2×one of CH$_2$), 1.72–2.10 (6H, m, 6×one of CH$_2$), 2.22 (3H, s, NCH$_3$), 3.18–3.40 (3H, m, HCS and 2×NCH), 7.11–7.20 (1H, m, Ar—H), 7.41–7.50 (1H, m, Ar—H) and 8.08 (1H, s, Ar—H); LCMS retention time ~2.38 min, m/z (FIAPOSES) 308.1 [Cl$^{35}$ (M+H)$^+$, 100%] and 310.1 [Cl$^{37}$ (M+H)$^+$, 33%].

EXAMPLE 57

EXO-4-Chloro-5-(8-methyl-8-aza-bicyclo[3.2.1]octane-3-sulfonyl)-1H-indazole

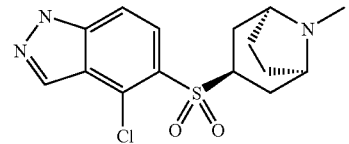

To a cloudy slurry of EXO-4-Chloro-5-(8-methyl-8-aza-bicyclo[3.2.1]oct-3-ylsulfanyl)-1H-indazole (Example 19, 393 mg, 1.28 mmol) in methanol (18 cm$^3$) with a small amount of CHCl$_3$ (2 cm$^3$) to try and aid solvation, was added a solution of Oxone (1.57 g, 2.56 mmol) at room temperature causing instant formation of a white solid. After stirring for one hour the reaction was loaded onto a SCX-2 cartridge and washed with methanol, then the cartridge was extracted with methanolic ammonia (2N). The basic solution was concentrated in vacua to yield EXO-4-Chloro-5-(8-methyl-8-aza-bicyclo[3.2.1]octane-3-sulfonyl)-1H-indazole (420 mg) as a brown foam; $\delta_H$ (300 MHz CDCl$_3$) 1.51–1.71 (4H, m, 4×one of CH$_2$), 2.02–2.19 (4H, m, 4×one of CH$_2$), 2.31 (3H, s, NCH$_3$), 3.29–3.35 (2H, m, 2×NCH), 3.71–3.89 (1H, m, HCS), 7.40–7.48 (1H, m, Ar—H), 7.90–7.99 (1H, m, Ar—H) and 8.25 (1H, s, Ar—H); LCMS retention time ~1.69 min, (FIAPOSES) 340.0 [Cl$^{35}$ (M+H)$^+$, 100%], 342.0 [Cl$^{37}$ (M+H)$^+$, 33%].

By proceeding in a similar manner there were prepared the following:

EXAMPLE 58

EXO 5,7-Dichloro-6-(8-methyl-8-aza-bicyclo[3.2.1]octane-3-sulfonyl)-1H-quinolin-2-one

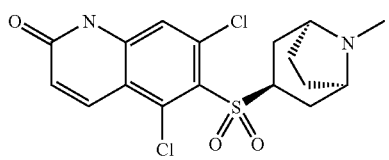

$\delta_H$ (300 MHz; D4 methanol) 1.78–1.99 (4H, m, 4×one of CH$_2$), 2.28–2.49 (4H, m, 4×one of CH$_2$), 2.53 (3H, s, NCH$_3$), 4.10-4.25 (1H, m, HCS), 6.99–7.08 (1H, m, Ar—H), 8.11 (1H, s, Ar—H) and 8.61–8.69 (1H, m, Ar—H); LCMS retention time ~0.64 min, m/z (FIAPOSES). 401.0 [Cl$^{35}$+Cl$^{35}$ (M+H)$^+$, 100%] and 403.0 [Cl$^{35}$+Cl$^{37}$ (M+H)$^+$, 67%].

EXAMPLE 59

EXO-5-Chloro-6-(8-methyl-8-aza-bicyclo[3.2.1]octane-3-sulfonyl)-3H-benzooxazol-2-one

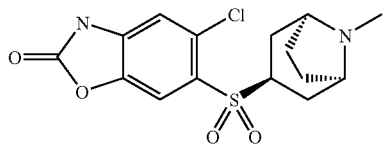

$\delta_H$ (300 MHz; D6 DMSO) 1.45–1.59 (4H, m, 4×one of CH$_2$), 1.80–2.00 (4H, m, 4×one of CH$_2$), 2.26 (3H, s, NCH$_3$), 3.64–3.79 (1H, m, SCH), 6.92 (1H, s, Ar—H) and 7.28 (1H, s, Ar—H);

EXAMPLE 60

EXO-6-(8-Methyl-8-aza-bicyclo[3.2.1]octane-3-sulfonyl)-1H-quinolin-2-one

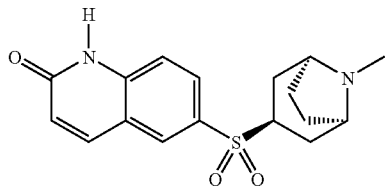

$\delta_H$ (300 MHz; D4 Methanol) 1.69–1.89 (4H, m, 4×one of CH$_2$), 2.00–2.20 (4H, m, 4×one of CH$_2$), 2.40 (3H, s, NCH$_3$), 3.45–3.55 (2H, m, 2×NCH), 3.56–3.67 (1H, m, HCS), 6.71–6.79 (1H, m, Ar—H), 7.51–7.58 (1H, m, Ar—H), 7.95–8.02 (1H, m, Ar—H), 8.08–8.13 (1H, m, Ar—H) and 8.22–8.24 (1H, m, Ar—H).

EXAMPLE 61

EXO-6-(8-Methyl-8-aza-bicyclo[3.2.1]octane-3-sulfonyl)-3H-benzooxazol-2-one

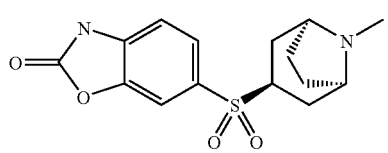

$\delta_H$ (300 MHz; D6 DMSO) 1.50–1.63 (4H, m, 4×one of CH$_2$), 1.72–1.85 (2H, m, 2×one of CH$_2$), 1.88–1.99 (2H, m, 2×one of CH$_2$), 2.22 (3H, s, NCH$_3$), 3.29–3.39 (2H, m, 2×NCH), 7.11–7.20 (1H, m, Ar—H) and 7.47–7.58 (2H, m, 2×Ar—H); LCMS retention time ~0.95 min, m/z (FLAPOS) 323.1 [(M+H)$^+$, 100%].

EXAMPLE 62

EXO-7-Chloro-6-(8-methyl-8-aza-bicyclo[3.2.1]octane-3-sulfonyl)-3H-benzooxazol-2-one hydrochloride salt

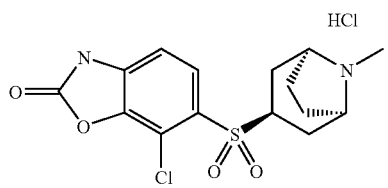

EXO-7-Chloro-6-(8-methyl-8-aza-bicyclo[3.2.1]octane-3-sulfonyl)-3H-benzooxazol-2-one hydrochloride salt; $\delta_H$ (300 MHz; D4 methanol) 1.81–1.99 (4H, m, 4×one of CH$_2$), 2.10–2.30 (4H, m, 4×one of CH$_2$), 2.61 (3H, s, NCH$_3$), 3.74-4.00 (3H, m, HCS and 2×NCH), 7.22–7.36 (1H, m, Ar—H) and 7.70–7.80 (1H, m, Ar—H).

EXAMPLE 63

EXO-3-Methyl-6-(8-methyl-8-aza-bicyclo[3.2.1]oct-3-ylsulfonyl)-1H,3H,4H-tetrahydroquinazolin-2-one

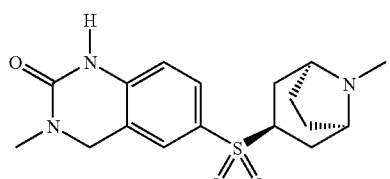

EXAMPLE 64

EXO-6-(8-methyl-8-aza-bicyclo[3.2.1]oct-3-ylsulfanyl)-3H-benzooxazol-2-one

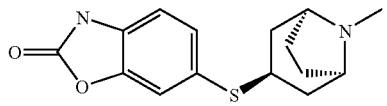

By proceeding in a similar manner to Example 44 but using 3H-benzooxazol-2-one in place of 2-hydroxyquinoline, there was prepared the title compound as a colourless solid.

EXAMPLE 65

EXO-6-(8-Methyl-8-aza-bicyclo[3.2.1]oct-3-ylsulfanyl)-1H,3H,4H-tetrahydroquinolin-2-one

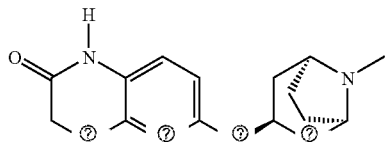

② indicates text missing or illegible when filed

By proceeding in a similar manner to Example 43 but using 1H,3H,4H-tetrahydroquinolin-2-one in place of 2-hydroxyquinoline, there was prepared the title compound as a pale yellow solid.

EXAMPLE 66

EXO-3-Methyl-6-(8-methyl-8-aza-bicyclo[3.2.1]oct-3-ylsulfanyl)-1H,3H,4H-tetrahydroquinazolin-2-one

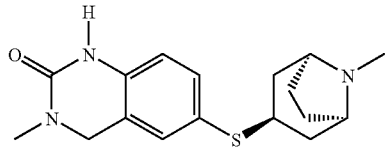

By proceeding in a similar manner to Example 44 but using 3-methyl-1H,3H,4H-tetrahydroquinazolin-2-one in place of 2-hydroxyquinoline, there was prepared the title compound as a pale yellow solid.

EXAMPLE 67

(a) EXO-5,7-Dichloro-6-(8-methyl-8-aza-bicyclo[3.2.1]oct-3-ylsulfanyl)-1H-quinolin-2-one

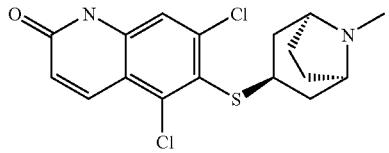

(i) EXO-3-(2,6-Dichloro-4-nitro-phenylsulfanyl)-8-methyl-8-aza-bicyclo[3.2.1]octane To a pale brown solution of EXO-Thioacetic acid S-(8-methyl-8-aza-bicyclo[3.2.1]oct-3-yl) ester (3.93 g, 19.7 mmol) and 1,2,3-Trichloro-5-nitro-benzene (5.37 g, 23.7 mmol) in ethanol was added 2 NaOH (10.85 $cm^3$, 21.7 mmol) at room temperature. After about five minutes the reaction was neutralised using 2N HCl (~1 $cm^3$) then concentrated in vacuo to remove the ethanol. The aqueous was treated with 2N NaOH (1.5 $cm^3$) and extracted using $CHCl_3$ (2×100 $cm^3$), the organics were combined, dried ($MgSO_4$) and concentrated in vacuo to dark yellow oil. This oil was purified by Flash Chromatography on silica (95:5 to 85:15; $CH_2Cl_2$,methanolic ammonia) yielding EXO-3-(2,6-Dichloro-4-nitrophenylsulfanyl)-8-methyl-8-azabicyclo[3.2.1]octane (5.12 g, 83%) as long yellow crystals {$δ_H$ (300 MHz; $CDCl_3$) 1.47–1.70 (4H, m, 4× one of $CH_2$), 1.87–2.05 (4H, m, 4× one of $CH_2$), 2.30 (3H, s, $NCH_3$), 3.11–3.20 (2H, m, 2×NCH), 3.60–3.73 (1H, m SCH) and 8.23 (2H, m, 2×Ar—H).

(ii) EXO-3,5-Dichloro-4-(8-methyl-8-aza-bicyclo[3.2.1]oct-3-ylsulfanyl)-phenylamine To a slurry of 5% Pd on charcoal (2 g) and ethanol was added a solution of EXO-3-(2,6-Dichloro-4-nitro-phenylsulfanyl)-8-methyl-8-aza-bicyclo[3.2.1]octane (5.12 g, 14.8 mmol) in ethanol. This mixture was placed under a pressurised atmosphere of hydrogen gas (60 PSI) at room temperature overnight. The reaction was filtered through celite® then concentrated in vacuo to give a colourless oil which was triturated with diethyl ether then concentrated in vacuo to yield EXO-3,5-Dichloro-4-(8-methyl-8-aza-bicyclo[3.2.1]oct-3-ylsulfanyl)-phenylamine (4.33 g, 93%) as a dry white foam; $δ_H$ (300 MHz; $CDCT_3$); 1.47–1.70 (4H, m, 4× one of $CH_2$), 1.82–2.03 (4H, m, 4×one of $CH_2$), 2.29 (3H, s, $NCH_3$), 3.11–3.21 (2H, m, 2×NCH), 3.22–3.39 (1H, m SCH), 3.81–3.92 ($NH_2$) and 6.70 (2H, s, 2×Ar—H); LCMC retention 1.70 min, m/z (FIAPOS) 317.1 [$Cl^{35}+Cl^{35}$ $(M+H)^+$, 100%] and 319.1 [$Cl^{35}+Cl^{37}$ $(M+H)^+$, 66%].

(iii) EXO—N-[3,5-Dichloro-4-(8-methyl-8-aza-bicyclo[3.2.1]oct-3-ylsulfanyl)-phenyl]-3-ethoxy-acrylamide To a solution of EXO-3,5-Dichloro-4-(8-methyl-8-aza-bicyclo[3.2.1]oct-3-ylsulfanyl)-phenylamine (300 mg, 0.95 mmol) in pyridine (1 $cm^3$) and $CH_2Cl_2$ (10 $cm^3$) was added 3-Ethoxy-acryloyl chloride (127 mg, 0.95 mmol) which was synthesised from ethoxy-ethene according to a literature procedure (Fernandez, Franco; Garcia-Mera, Xerardo; Morales, Melvin; Rodriguez-Borges, Jose E.; Synthesis; 2; 2001; 239–242). The reaction was stirred at room temperature for 2.5 hours then the solid that had formed was filtered off and washed with $CH_2Cl_2$ to yield EXO—N-[3,5-Dichloro-4-(8-methyl-8-aza-bicyclo[3.2.1]oct-3-ylsulfanyl)-phenyl]-3-ethoxy-acrylamide hydrochloride salt (289 mg, ~68%); $δ_H$ (300 MHz; D4 methaol) 1.30–1.41 (3H, m, $OCH_2CH_3$), 1.90–2.18 (6H, m, 6× one of $CH_2$), 2.23–2.47 (2H, m, 2×one of $CH_2$), 2.76 (3H, s, $NCH_3$), 3.48–3.52 (1H, m, SCH), 3.81–3.90 (2H, m, 2×NCH), 3.924.01 (2H, m, $OCH_2CH_3$), 5.55–5.65 (2H, m, NH and C=CH), 7.59–7.69 (1H, m, C=CH) and 7.81–7.86 (2H, m, 2×Ar—H); LCMC retention ~2.38 min, m/z (FIAPOS) 415.1 [$Cl^{35}+Cl^{35}$ $(M+H)^+$, 100%] and 417.1 [$Cl^{35}+Cl^{37}$ $(M+H)^+$, 66%].

(iv) EXO-5,7-Dichloro-6-(8-methyl-8-aza-bicyclo[3.2.1]oct-3-ylsulfanyl)-1H-quinolin-2-one hydrochloride salt EXO—N-[3,5-Dichloro-4-(8-methyl-8-aza-bicyclo[3.2.1]oct-3-ylsulfanyl)-phenyl]-3-ethoxy-acrylamide hydrochloride salt (280 mg) was treated with concentrated $H_2SO_4$ (~1 cm$^3$) causing a colour change from yellow to red. After 10 minutes the reaction was poured onto crushed ice. This was slowly warmed to room temperature to give a yellow solution which was basified using 2N NaOH (~10 cm$^3$) to give a turbid mixture which was extracted with CHCl$_3$ (2×30 cm$^3$). The chloroform layer was treated with methanol, dried (MgSO$_4$) and concentrated in vacuo to a yellow solid. This yellow solid was washed with CH$_2$Cl$_2$ then dissolved in methanol and treated with methanolic HCl to yield EXO-5,7-Dichloro-6-(8-methyl-8-aza-bicyclo[3.2.1]oct-3-ylsulfanyl)-1H-quinolin-2-one hydrochloride salt (100 mg) as a white solid; $\delta_H$ (300 MHz; CDCl$_3$) 1.95–2.36 (8H, m, 4×CH$_2$), 2.78 (3H, s, NCH$_3$), 3.53–3.70 (1H, m, HCS), 3.89–3.99 (2H, m, 2×NCH), 6.71–6.79 (1H, m, Ar—H), 7.52 (1H, s, Ar—H) and 8.28–8.33 (1H, m, Ar—H); LCMS retention time ~1.65 min, m/z (FIAPOSES) 369.1 [Cl$^{35}$+Cl$^{35}$ (M+H)$^+$, 100%] and 371.1 [Cl$^{35}$+Cl$^{37}$ (M+H)$^+$, 67%].

(b) EXO-5-chloro-8-methyl-6-(8-methyl-8-aza-bicyclo[3.2.1]oct-3-ylsulfanyl)-1H-quinolin-2-one By proceeding in a similar manner to Example 67(a) but using 4,5-dichloro-2-nitro-toluene in step (i), there was prepared EXO-5-chloro-8-methyl-6-(8-methyl-8-aza-bicyclo[3.2.1]oct-3-ylsulfanyl)-1H-quinolin-2-one.

(c) EXO-5,7-dichloro-6-(8-methyl-8-aza-bicyclo[3.2.1]oct-6en-3-ylsulfanyl)-1H-quinolin-2-one By proceeding in a similar manner to Example 67(a) but using exo-thioacetic acid S-(8-methyl-8-aza-bicyclo[3.2.1]oct-6-en-3-yl) ester [Example 42(ii)] in step (i), there was prepared EXO-5,7-dichloro-68-methyl-8-aza-bicyclo[3.2.1]oct-6-en-3-ylsulfanyl)-1H-quinolin-2-one.

Example 68

EXO-5,7-Dimethyl-6-(8-methyl-8-aza-bicyclo[3.2.1]oct-3-ylsulfanyl)-1H-quinolin-2-one

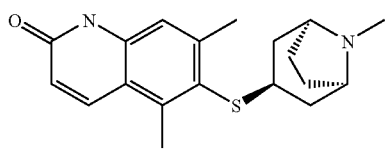

By proceeding in a similar manner to Example 67 but using 1-chloro-2,6-dimethyl4-nitro-benzene in place of 1,2,3-trichloro-5-nitro-benzene, there was prepared the title compound as a colourless solid.

$\delta_H$ (300 MHz CDCl$_3$) 1.39–1.48 (2H, m, 2×one of CH$_2$), 1.54–1.63 (2H, m, 2×one of CH$_2$), 1.79–2.00 (4H, m, 4×one of CH$_2$), 2.25 (3H, s, NCH$_3$), 2.61 (CH$_3$), 2.82'(CH$_3$), 2.91–3.08 (1H, m, HCS), 3.09–3.16 (2H, m, 2×NCH), 6.65–6.71 (1H, m, Ar—H), 7.20 (1H, s, Ar—H), 7.97–8.05 (1H, m, Ar—H) and 12.32 (1H, br s, NH); LCMS retention time ~2.93 min, (FIAPOSES). 329.1 [(M+H)$^+$, 100%].

EXAMPLE 69

EXO 5,7-Dichloro-6-(8-methyl-8-aza-bicyclo[3.2.1]oct-3-ylsulfanyl)-1H-quinoline-2-thione

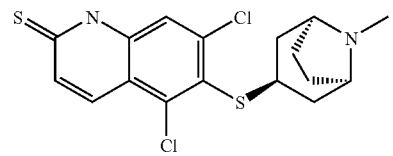

A slurry EXO-5,7-Dichloro-6-(8-methyl-8-aza-bicyclo[3.2.1]oct-3-ylsulfanyl)-1H-quinolin-2-one (407 mg, 1.1 mmol) and Lawesson's Reagent [2,4-bis(4-methoxyphenyl)-1,3-dithia-2,4-diphospbetane-2,4-disulfide] (446 mg, 1.10 mmol) in toluene was heated to reflux under a flow of nitrogen gas overnight. The reaction was cooled to room temperature then concentrated in vacuo onto silica and columned using gradient elution (98:2 to 75:25 CH$_2$Cl$_2$: methanolic ammonia) yielding EXO-5,7-Dichloro-6-(8-methyl-8-aza-bicyclo[3.2.1]oct-3-ylsulfanyl)-1H-quinoline-2-thione (160 mg) as a bright yellow solid; $\delta_H$ (300 MHz CDCl$_3$) 1.47–1.55 (2H, m, 2×one of CH$_2$), 1.60–1.71 (2H, m, 2×one of CH$_2$), 1.89–2.01 (4H, m, 4×one of CH$_2$),2.29 (3H, s, NCH$_3$),3.13–3.21 (2H, m, 2×NCH), 3.38–3.41 (1H, m, HCS), 7.39–7.47 (2H, m, 2×Ar—H) and 7.91–7.99 (1H, m, Ar—H).

EXAMPLE 70

EXO-7-Methyl-6-(8-methyl-8-aza-bicyclo[3.2.1]oct-3-ylsulfanyl)-3H-benzooxazol-2-one

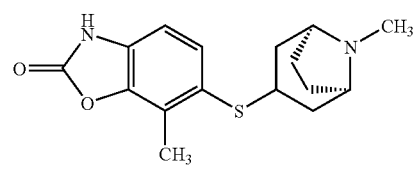

(i) 7-Methyl-3H-benzooxazol-2-one-6-sulfonic acid

7-Methyl-3H-benzooxazol-2-one [5.0 g, 33 mmol, prepared according to the procedure described in J. Org. Chem. (1982), 47(14), 2804–6) was treated with chlorosulphonic acid as described in Example 15 (i) to give the title compound as an off-white solid (4.5 g, 60%).

$\delta_H$ (300 MHz, DMSO) 2.50 (s, 3H), 6.83 (d, 1H), 7.58 (d, 1H), 11.60 (brs, 1H)

(ii) EXO-7-Methyl-6-(8-methyl-8-aza-bicyclo[3.2.1]oct-3-ylsulfanyl)-3H-benzooxazol-2-one A mixture of 7-methyl-3H-benzooxazol-2-one-6-sulfonic acid (2.5 g, 11 mmol), triphenylphosphine (13 g, 50 mmol) and benzene (100 ML) was heated at reflux for 2 h under Dean and Stark conditions. The reaction was cooled and treated with iodine (5 g, 20 mmol) in small portions. The reaction was heated to reflux for a further 48 h before being cooled and washed with 2.0M aqueous sodium hydroxide (2×20 ml). The combined aqueous extracts were washed with chloroform (2×50 ml) and acidified to pH 4 with concentrated hydrochloric acid. The resultant solid was collected and dried to yield a white solid which was used directly in the next step.

This material was treated with ENDO-methanesulfonic acid 8-methyl-8-aza-bicyclo[3.2.1]oct-3-yl ester and cesium fluoride in DMF according to the procedure described in Example 15 (iii). There was thus obtained the title compound as a colourless solid.

$\delta_H$ (300 MHz; D4 methanol) 1.82–2.26 (8H), 2.65 (3H, s), 2.78 (3H, s), 3.35–3.49 (1H, m), 3.72–3.83 (2H, m), 6.96 (1H, d) and 7.40 (1H, d). FIA-MS: 305 [(M+H)$^+$, 100%].

EXAMPLE 71

6-(9-Methyl-9-aza-bicyclo[3.3.1]non-3(exo)-ylsulfanyl)-1-NH-quinolin-2-one

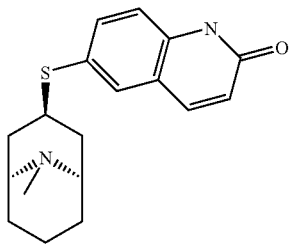

(i) 9-Methyl-9-aza-bicyclo[3,3, 1]nonan-3(endo)-ol

To a −78° C. cooled solution of pseudopelletierine (771 mg, 5.04 mmol), obtained from the its chloro hydrate (pseudopelletierine chloride, commercially available) by treatment with saturated aqueous solution of NaHC$_{0-3}$, extracted with methylene chloride, and dried; in THF anhydrous (20 mL), a solution 1.0 M of DIBAL-H in hexane or toluene (10.8 mL, 10.8 mmol) was added dropwise under N$_2$. The mixture was stirred and allowed to reach rt. for 3 h. The reaction was quenched with water (2 mL) and poured into diethyl ether (60 mL). NaHCO$_3$ anhydrous (20 g) and Na$_2$SO$_4$ anhydrous (20 g) were added. The mixture was stirred for 2 h at rt., and then, it was filtered and the filtrate was evaporated. The residue was the title compound pure, 684 mg, 88%.

Ion Electrospray Mass Spectrum M+1: 156. $^1$H NMR (200 MHz, CDCl$_3$) δ (ppm): 4.16 (m, 1 H), 2.95 (br m, 2 H), 2.40–2.20 (m, 2 H), 2.00–1.80 (m, 3 H), 1.40–1.25 (m, 3 H), 1.20–1.05 (m, 2H) $^{13}$C NMR (50 MHz, CDCl$_3$) δ (ppm): 62.9, 51.6, 40.4, 34.8, 24.9, 14.4

(ii) 3(endo)-Hydroxy-9-aza-bicyclo[3,3, 1]nonane-9-carboxylic acid ethyl ester

To a solution of the intermediate from step (i) (2.31 g, 14.90 mmol) in dry chloroform (300 mL), ethyl chloroformate (9.97 mL, 104.30 mmol) followed by potassium bicarbonate (1.78 g, 17.88 mmol) were added. The mixture was heated at 80° C. and stirred under N$_2$ overnight. The reaction was cooled down, quenched with water (30 mL) and extracted with chloroform. The organic layer was dried on MgSO$_4$ anhydrous, and the solvent was removed in vacuo. The residue was the title compound pure, 3.04 g, 96%. The product is a mixture of rotamers, the major one is described as following:

Ion Electrospray Mass Spectrum M+1: 214 $^1$H NMR (200 MHz, CDCl$_3$) δ (ppm): 4.45 (br d, 2 H), 4.10 (q, J=7.0 Hz, 2H), 3.68 (m, 1 H), 2.30 (m, 2 H), 1.84 (br, s, 1 H), 1.50–1.30 (m, 7 H), 1.23 (t, J=7.0 Hz, 3H) $^{13}$C NMR (75 MHz, CDCl$_3$) δ (ppm): 154.2, 62.8, 60.1, 43.9, 33.5, 29.3, 13.7, 13.0

(iii) 3(endo)-Methanesulfonyloxy-9-aza-bicyclo[3,3, 1]nonane-9-carboxylic acid ethyl ester To an ice-cooled solution of the intermediate from step (ii) (3.04 g, 14.27 mmol) in methylene chloride anhydrous, pyridine anhydrous (1.04 mL, 12.84 mmol) followed by methanesulfonate chloride (1.21 mL, 15.70 mmol) were added under N$_2$. The mixture was stirred overnight and allowed to reach rt. As the reaction hadn't finished pyridine anhydrous (2.08 mL, 26 mmol) and methanesulfonate chloride (2.42 mL, 31.40 rmnol) were added at 0° C. under N$_2$. The new mixture was stirred at rt for 24 h. The reaction was quenched with an aqueous solution of NH$_4$OH (32%), and extracted with methylene chloride. The organic layer was washed with brine and dried on MgSO$_4$ anli. The solvent was removed in vacuo to give the title compound, 1.34 g, 32%. The product is a mixture of rotamers, the major one is described as following Ion Electrospray Mass Spectrum M+1: 292 $^1$H NMR (200 MHz, CDCl$_3$) δ (ppm): 4.66 (m, 1 H), 4.50 (br m, 2 H), 4.10 (q, J=7.0 Hz, 2H), 2.99 (s, 3 H), 2.45 (m, 2 H), 1.70–1.50 (m, 8 H), 1.24 (t, J=7.0Hz, 3H)

(iv) 3 (exo)-(2-Oxo-1,2-dihydro-quinolin-6-ylsulfanyl)-9-aza-bicyclo[3.3.1]nonane-9-carboxylic acid ethyl ester To a solution of the intermediate from step (iii) (1.34 g, 4.60 mmol), thioacetic acid S-(2-oxo-1,2-dihydro-quinolin-6-yl) ester (98.3 mg, 0.78 mmol), cesium fluoride (699 mg, 4.60 mmol) in dry DMF (10 mL), pyrrolidine (654.3 mg, 9.20 mmol) was added at rt. The mixture was degassed, heated at 80° C. and stirred overnight under N$_2$. The reaction was quenched with water, and filtered to remove the cessium fluoride excess. The filtrate was extracted with ethyl acetate. The organic layer was washed with water and brine, and dried on MgSO$_4$ anh. The solvent was removed in vacuo to give the title compound, which was submitted to the next reaction without further treatment.

Ion Electrospray Mass Spectrum M+1: 373, M−1: 371.

(v) 6-(9-Methyl-9-aza-bicyclo[3.3.1]non-3 (exo)-ylsulfanyl)-1—NH—quinolin-2-one

To an ice-cooled solution of the intermediate from step (iv) (536 mg, 1.4 mmol) in toluene anhydrous (11 mL), sodium bis(methoxyethoxy) aluminium hydride (Red-Al (3.4 M in toluene)) (1.47 mL, 5.02 mmol) was added. The mixture was stirred overnight under N$_2$ and allowed to reach rt. Once the starting material had disappeared by mass analysis, the solvent was removed in vacuo. The residue was dissolved in methanol and submitted to SCX purification followed by SPE purification. As the desired product was further purified by reverse phase HPLC in two batches. For the first batch, formic acid was used in the purification and 50 mg, 10%, were obtained of the title compound. From the second one, trifluoroacetic acid was used getting 70 mg, 12% of the corresponding trifluorooacetate salt. Total yield: 22%

Ion Electrospray Mass Spectrum M+1: 315 $^1$H NMR (500 MHz, CD$_3$OD) δ (ppm) for the free amine: 7.96 (d, J=9.5 Hz, 1H), 7.87 (d, J=1.5 Hz, 1H), 7.70 (dd, J=8.5 y 1.9 Hz, 1H), 7.37 (d, J=8.5 Hz, 1H), 6.64 (d, J=9.5 Hz, 1H), 3.92 (m, 1H), 3.54 (br, s, 2H), 2.90 (s, 3H), 2.24 (m, 6H), 2.04 (m, 1H). 1.92 (m, 2H), 1.73 (m, 1H)

EXAMPLE 72

3-Chloro-4-[(8-methyl-8-azabicylo[3.2.1]oct-3-yl)thio]phenol

By proceeding in a similar manner to Example 9 but using 3-chlorophenol in place of 3-bromophenol in step (i), there was prepared the title compound as a colourless solid.

δ$_H$ (300 MHz; D6 DMSO) 1.47 (2H, m), 1.58 (4H, m), 1.90 (2H, m), 2.10 (3H, s), 3.02 (2H, m), 3.28 (1H, m), 6.75 (1H, m), 6.90 (1H, m); 7.39 (1H, m); FIA-MS: 284[(M+H)$^+$, 100%].

What is claimed is:

1. A compound represented by Formula (I) or pharmaceutically acceptable salts thereof:

(I)

wherein:
R$^1$ is —H, C$_{1-12}$alkyl optionally substituted with 1, 2 or 3 groups independently selected from halogen, hydroxyl, thiol, C$_{1-4}$alkoxy or C$_{1-4}$alkylthio, or aryl-C$_{1-4}$alkyl;
R$^2$ is
—OH,
—NH$_2$,
—NH-Q-V-T, wherein Q is —C(O)—, —C(O)—NH—, —C(O)O—, or —SO$_2$—;
V is H, aryl, aryl-C$_{1-12}$alkyl, diaryl-C$_{1-12}$alkyl, lactonyl, or C$_{1-18}$alkyl optionally substituted with halogen, hydroxyl, C$_{1-4}$alkoxy, —C(O)OC$_{1-4}$alkyl, —OC(O)C$_{1-4}$alkyl, aryl-C$_{1-4}$alkoxy, aryloxy, or SO$_2$C$_{1-4}$alkyl; and T is H, halogen, C$_{1-5}$alkyl, C$_{1-4}$alkoxy, nitro, aryl, aryl-C$_{1-4}$alkyl, or aryloxy unless V is H in which case T is absent,
aryl,
-(L)$_a$-Z, wherein L is CH$_2$, CO, O, NH or N(C$_{1-4}$alkyl) and a is
0 or 1; and Z is C$_{1-3}$alkyl-F, C$_{0-3}$alkyl-aryl-R$^6$, C$_{0-3}$alkyl-CO—R$^6$, C$_{0-3}$alkyl-CO—NR$^6_2$, C$_{0-3}$alkyl-CO$_2$—R$^6$, C$_{0-3}$alkyl-SO$_2$—R$^6$, C$_{0-3}$alkyl-SO$_2$—NR$^6_2$, C$_{1-3}$alkyl-OR$^6$, C$_{1-3}$alkyl-CN or C$_{1-3}$alkyl-NR$^6_2$, wherein each C$_{0-3}$alkyl or C$_{1-3}$alkyl portion is optionally substituted with from 1 to 6 groups selected from F and C$_{1-5}$alkyl, linked back to the aromatic ring so as to form a fused bicyclic compound represented by Formula (Ia)

(Ia)

wherein D is O or S; and
E is O, S, NR$^5$, C(R$^5$)$_2$, O—CR$^5_2$, NR$^5$—CR$^5_2$, NR$^5$—CO, CR$^5_2$—O, CR$^5_2$—S(O)$_r$, CR$^5_2$—NR$^5$, CR$^5_2$—CR$^5_2$, CO—NR$^5$, or CR$^5$=CR$^5$; or
linked back to the aromatic ring so as to form a fused bicyclic compound represented by Formula (Ib)

Formula (Ib)

wherein G is CR$^5$ or N; and
J is CR$^5$ or N;
unless X is N in which case R$^2$ is absent
R$^3$ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R$^4$ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R$^5$ is each independently H or C$_{1-4}$alkyl;
R$^6$ is each independently H, C$_{1-6}$alkyl, aryl or arylC$_{1-4}$alkyl, each of which (except H) may be optionally substituted with from 1 to 3 fluorine atoms;
X is C or N;
W is C or N;
W' is C or N;
Y is C or N;
Y' is C or N;
provided that there are no more than two N atoms in the aryl ring;
A is (CH$_2$)$_q$;

m, n are both 1;
o and p are both 0;
q 2;
r is 0, 1 or 2;
provided that when X, W, W', Y and Y' are all C, $R^3$ is H, $R^4$ is H or Cl positioned meta to the sulphur atom, A is $(CH_2)_Q$ and $R^1$ is selected from H, unsubstituted $C_{1-4}$alkyl and unsubstituted $C_{3-4}$cycloalkyl; then $R^2$ may not be H or —OH, and that
when one of X, Y and Y' is N, $R^3$ is H, $R^4$ is H or Cl positioned meta to the sulphur atom, A is $(CH_2)_Q$ and $R^1$ is selected from H, unsubstituted $C_{1-4}$alkyl and unsubstituted $C_{3-4}$cycloalkyl; the $R^2$ may not be H or —OH.

2. A compound as claimed in claim 1 wherein:
$R^1$ is
—$NH_2$,
—NH-Q-V-T,
aryl,
-(L)$_a$-Z,
linked back to the aromatic ring so as to form a fused bicyclic compound represented by Formula (Ia), or
linked back to the aromatic ring so as to form a fused bicyclic compound represented by Formula (Ib);
unless X is N in which case $R^2$ is absent.

3. A compound as claimed in claim 1 or claim 2 wherein:
$R^2$ is —NH-Q-V-T,
aryl,
-(L)$_a$-Z,
linked back to the aromatic ring so as to form a fused bicyclic compound represented by Formula (Ia), or
linked back to the aromatic ring so as to form a fused bicyclic compound represented by Formula (Ib);
unless X is N in which case $R^2$ is absent.

4. A compound as claimed in claim 3 wherein:
$R^2$ is —NH-Q-V-T wherein Q is —C(O)—NH—, or —C(O)O—;
V; and
T;
aryl,
-(L)$_a$-Z,
linked back to the aromatic ring so as to form a fused bicyclic compound represented by Formula (Ia), or
linked back to the aromatic ring so as to form a fused bicyclic compound represented by Formula (Ib);
unless X is N in which case $R^2$ is absent.

5. A compound as claimed in claim 1 wherein:
$R^1$ is —H,
$C_{1-12}$alkyl optionally substituted with 1, 2 or 3 groups independently selected from halogen, hydroxyl, thiol, $C_{1-4}$alkoxy or $C_{1-4}$alkylthio, or
aryl-$C_{1-4}$alkyl;
$R^2$ is
—OH,
—$NH_2$,
—NH-Q-V-T, wherein Q is —C(O)—, —C(O)—NH—, —C(O)O—, or —$SO_2$—;
V is aryl, aryl-$C_{1-12}$alkyl, diaryl-$C_{1-12}$alkyl, lactonyl, or $C_{1-8}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or $SO_2C_{1-4}$ alkyl; and
T is H, halogen, aryl, aryl-$C_{1-4}$alkyl, or aryloxy,
$R^3$ is H, halogen, $C_{1-4}$alkyl, cyano, $CF_3$, $OC_{1-4}$alkyl, aryloxy, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH,
$R^4$ is H, halogen, $C_{1-4}$alkyl, cyano, $CF_3$, $OC_{1-4}$alkyl, aryloxy, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH,
X is C or N,
W is C or N, provided that both X and Y are not N,
W' is C
Y is C or N
Y' is C
q is optionally 1, 2 or 3
r is 0.

6. A compound as claimed in claim 5 wherein $R^1$ is H, $C_{1-6}$alkyl optionally substituted with 1 or 2 hydroxyl groups, or aryl-$C_{1-4}$alkyl.

7. A compound as claimed in claim 6 wherein $R^1$ is benzyl, p-methoxybenzyl, furanylmethyl, imidazolylmethyl, pyridinylmethyl, thienylmethyl, pyridylmethyl, N-hydroxypyridylmethyl or thiazolylmethyl.

8. A compound as claimed in claim 7 wherein $R^2$ is $R^3$ is carbonamido (—$CONH_2$) or $C_{1-4}$alkyl-OH, and $R^4$ is H, $C_{1-4}$alkyl, $CF_3$, halogen or cyano.

9. A compound as claimed in claim 7 wherein $R^2$ is OH, and $R^3$ and $R^4$ each independently represent H, $C_{1-4}$alkyl, $CF_3$, cyano or halogen.

10. A compound as claimed in claim 7 wherein $R^2$ is of formula —NH-Q-V-T; T is H and $R^3$ and $R^4$ each independently represent H, methyl, $CF_3$, chloro- or cyano-.

11. A compound as claimed in claim 7 wherein $R^2$ is of formula —NH—SO2-V-T; V is aryl, —$C_{1-12}$alkyl or aryl-$C_{1-12}$alkyl; $R^3$ is H, methyl, $CF_3$, Cl or cyano and $R^4$ is H.

12. A compound as claimed in claim 7 wherein $R^2$ is of formula —NH—$SO_2$-V-T, V is selected from $C_{1-12}$alkyl, phenyl, naphthyl, thienyl, oxazolyl, isoxazolyl, or phenyl (CH=CH)—, optionally substituted with 1, 2, 3 or 4 substituents selected from:
—$NO_2$;
halogen;
—$CF_3$;
$C_{1-12}$alkoxy;
$C_{1-12}$alkylthio;
$C_{1-12}$alkyl;
$C_{1-4}$alkylsulfonyl;
—CN;
—$OCF_3$;
—C(O)O$C_{1-4}$alkyl;
—$OCH_2CF_3$;
—NHC(O)$C_{1-4}$alkyl.

13. A compound as claimed in claim 7 wherein $R^2$ is of formula —NH—$SO_2$-V-T, T is selected from H; or diazole, oxazole, isoxazole, phenyl or phenoxy, optionally substituted with 1, 2, 3 or 4 substituents selected from
—$NO_2$;
halogen;
—$CF_3$;
$C_{1-12}$alkoxy;
$C_{1-12}$alkylthio;
$C_{1-12}$alkyl;
$C_{1-4}$alkylsulfonyl;
—CN;
—$OCF_3$;
—C(O)O$C_{1-4}$alkyl;
—$OCH_2CF_3$;
—NHC(O)$C_{1-4}$alkyl.

14. A compound as claimed in claim 7 wherein $R^2$ is of formula —NH—SO$_2$-V-T, V is selected from 3-chloro-4-methylphenyl, 3-chlorophenyl, 3-methoxyphenyl, 4-bromophenyl, 4-methylphenyl, 4-methylphenyl, naphthyl, 2,4,6-trimethylphenyl, phenyl(CH=CH)—, 4-chlorophenyl, 2-chlorophenyl, 2,5-dichlorothien-3-yl, 2,5,6-trimethyl-4-methoxyphenyl, 4-methoxyphenyl, 2,3,4-trifluorophenyl, 3-cyanophenyl, 2-methoxycarbonylthien-3-yl or 4-pentylphenyl and T is H.

15. A compound as claimed in claim 7 wherein $R^2$ is of formula —NH—SO$_2$-V-T, T is 2-chloro-5-nitrophenoxy and V is phenyl.

16. A compound as claimed in claim 7 wherein $R^2$ is of formula —NH—C(O)-V-T wherein V is selected from aryl; aryl-C$_{1-12}$alkyl; diaryl-C$_{1-12}$alkyl; lactonyl; or C$_{1-18}$alkyl optionally substituted with halogen, hydroxyl, C$_{1-4}$alkoxy, C(O)OC$_{1-4}$alkyl, OC(O)C$_{1-4}$alkyl, aryl-C$_{1-4}$alkoxy or aryloxy.

17. A compound as claimed in claim 7 wherein $R^2$ is of formula —NH—C(O)-V-T, and V is selected from C$_{1-2}$alkyl, phenyl, phenyl-C$_{1-12}$alkyl, diphenylmethyl, naphthyl, furanyl, thienyl, diazolyl, pyridinyl, thiazolyl, benzothienyl, fluorenyl, oxazolyl or isoxazolyl, optionally substituted with 1, 2, 3 or 4 substituents independently selected from
- —NO$_2$;
- halogen;
- —CF$_3$;
- C$_{1-12}$alkoxy;
- C$_{1-12}$alkylthio;
- C$_{1-12}$alkyl;
- C$_{1-4}$alkylsulfonyl;
- —CN;
- —OCF$_3$;
- —C(O)O—C$_{1-4}$alkyl;
- —OCH$_2$CF$_3$.

18. A compound as claimed in claim 7 wherein $R^2$ is of formula —NH—C(O)-V-T, T is selected from H; halogen; or diazole, oxazole, isoxazole, phenyl, phenoxy or benzodioxanyl optionally substituted with 1, 2, 3 or 4 substituents selected from
- —NO$_2$;
- halogen;
- —CF$_3$;
- C$_{1-12}$alkylthio;
- C$_{1-12}$alkoxy;
- C$_{1-12}$alkyl;
- C$_{1-4}$alkylsulfonyl;
- —CN;
- —OCF$_3$;
- —C(O)O—C$_{1-4}$alkyl.

19. A compound as claimed in claim 7 wherein $R^2$ is of formula —NH—C(O)NH-V-T wherein V is selected from C$_{1-18}$alkyl optionally substituted with halogen, hydroxyl, C$_{1-4}$alkoxy, C(O)OC$_{1-4}$alkyl, OC(O)C$_{1-4}$alkyl, aryl-C$_{1-4}$alkoxy or aryloxy; aryl; or aryl-C$_{1-12}$alkyl.

20. A compound as claimed in claim 7 wherein $R^2$ is of formula —NH—C(O)NH-V-T, V is selected from phenyl, phenyl-C$_{1-12}$alkyl or naphthyl optionally substituted with 1, 2, 3 or 4 substituents selected from
- —NO$_2$;
- halogen;
- —CF$_3$;
- C$_{1-12}$alkylthio;
- C$_{1-12}$alkoxy;
- C$_{1-12}$alkyl;
- C$_{1-4}$alkylsulfonyl;
- —CN;
- —OCF$_3$;
- —C(O)O—C$_{1-4}$alkyl.

21. A compound as claimed in claim 7 wherein $R^2$ is of formula —NH—C(O)O-V-T, wherein V is selected from C$_{1-18}$alkyl optionally substituted with halogen, hydroxyl, C$_{1-4}$alkoxy, C(O)OC$_{1-4}$alkyl, OC(O)C$_{1-4}$alkyl, aryl-C$_{1-4}$alkoxy or aryloxy; aryl; or aryl-C$_{1-12}$alkyl.

22. A compound as claimed in claim 7 wherein $R^2$ is of formula —NH—C(O)O-V-T, preferably V is selected from phenyl or phenyl-C$_{1-12}$alkyl optionally substituted with 1, 2, 3 or 4 substituents selected from
- —NO$_2$;
- halogen;
- —CF$_3$;
- C$_{1-12}$alkylthio;
- C$_{1-12}$alkoxy;
- C$_{1-12}$alkyl;
- C$_{1-4}$alkylsulfonyl;
- —CN;
- —OCF$_3$;
- —C(O)O—C$_{1-4}$alkyl; or
- —OCH$_2$CF$_3$.

23. A compound as claimed in claim 1 wherein $R^2$ is of formula —NH—C(O)-V-T
wherein
V is H, C$_{1-6}$alkyl, C$_{3-6}$cycloalkyl, aryl or aryl-C$_{1-12}$alkyl; and
T is H, halogen, C$_{1-5}$alkyl, C$_{1-4}$alkoxy, nitro, aryl, aryl-C$_{1-4}$alkyl, or aryloxy unless V is H in which case T is absent.

24. A compound as claimed in claim 23
wherein
V is H, C$_{1-6}$alkyl or C$_{3-6}$cycloalkyl; and
T is H unless V is H in which case T is absent.

25. A compound as claimed in claim 23
wherein
V is aryl or aryl-C$_{1-12}$alkyl; and
T is H, halogen, C$_{1-5}$alkyl, C$_{1-4}$alkoxy, nitro, aryl, aryl-C$_{1-4}$alkyl, or aryloxy.

26. A compound as claimed in claim 25
wherein
V is phenyl, pyridyl, thienyl, thiazolyl, thiadiazolyl, or phenyl-C$_{1-6}$alkyl; and
T is H, halogen, C$_{1-5}$alkyl, C$_{1-4}$alkoxy, nitro, aryl, aryl-C$_{1-4}$alkyl, or aryloxy.

27. A compound as claimed in claim 1
wherein
$R^1$ is —H,
  C$_{1-12}$alkyl optionally substituted with 1, 2 or 3 groups independently selected from halogen, hydroxyl, thiol, C$_{1-4}$alkoxy or C$_{1-4}$alkylthio, or
  aryl-C$_{1-4}$alkyl;
$R^2$ is —NH$_2$, or
  —NH-Q-V-T, wherein Q is —C(O)—, —C(O)—NH—, —C(O)O—, or —SO$_2$—;
    V is H, aryl, aryl-C$_{1-12}$alkyl, diaryl-C$_{1-12}$alkyl, lactonyl, or C$_{1-18}$alkyl optionally substituted with halogen, hydroxyl, C$_{1-4}$alkoxy, —C(O)OC$_{1-4}$alkyl, —OC(O) C$_{1-4}$alkyl, aryl-C$_{1-4}$alkoxy, aryloxy, or SO$_2$C$_{1-4}$alkyl; and
    T is H, halogen, aryl, aryl-C$_{1-4}$alkyl, or aryloxy unless V is H in which case T is absent,
$R^3$ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—$C_{1-4}$ alkyl, aryl, hydroxy, —$SO_2NH_2$, —$SO_2NHC_{1-4}$alkyl, or —$C_{1-4}$alkyl-OH;

$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$ alkyl, aryl, hydroxy, —$SO_2NH_2$, —$SO_2NHC_{1-4}$alkyl, or —$C_{1-4}$alkyl-OH;

X is C;

W is C or N;

W' is C or N;

Y is C or N;

Y' is C or N;

provided that there are not more than two N atoms in the aryl ring and provided that at least one of W, W', Y or Y' is N;

A is optionally a CH=CH double bond, $(CH_2)_q$ or $(CH_2)O(CH_2)$;

r is 0, 1 or 2.

28. A compound as claimed in claim 27 wherein
W is C;
W' is C;
Y' is C; and
Y is N.

29. A compound as claimed in claim 27 wherein
W is N;
W' is C;
Y' is C; and
Y is C.

30. A compound as claimed in claim 29 wherein
$R^2$ is —$NH_2$.

31. A compound as claimed in claim 29 wherein
$R^2$ is —NH-Q-V-T, wherein Q is —C(O)—, —C(O)—NH—, —C(O)O—, or —$SO_2$—;
V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O) $C_{1-4}$alkyl, aryl-$C_{1-4}$alkoxy, aryloxy, or $SO_2C_{1-4}$alkyl; and
T is H, halogen, aryl, aryl-$C_{1-4}$alkyl, or aryloxy unless V is H in which case T is absent.

32. A compound as claimed in claim 31 wherein
Q is —$SO_2$—or —CO—.

33. A compound as claimed in claim 1 wherein
$R^1$ is —H,
$C_{1-12}$alkyl optionally substituted with 1, 2 or 3 groups independently selected from halogen, hydroxyl, thiol, $C_{1-4}$alkoxy or $C_{1-4}$alkylthio, or
aryl-$C_{1-4}$alkyl;
$R^2$ is aryl,
$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$ alkyl, aryl, hydroxy, —$SO_2NH_2$, —$SO_2NHC_{1-4}$alkyl, or —$C_{1-4}$alkyl-OH,
$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$ alkyl, aryl, hydroxy, —$SO_2NH_2$, —$SO_2NHC_{1-4}$alkyl, or —$C_{1-4}$alkyl-OH;

X is C,

W is C or N;

W' is C or N;

Y is C or N;

Y' is C or N;

provided that there are no more than two N atoms in the aryl ring;

r is 0, 1 or 2.

34. A compound as claimed in claim 33 wherein $R^2$ is a $C_3$ to $C_{12}$ aromatic or heteroaromatic group optionally substituted with one or more substituents selected from $C_{1-12}$alkyl, $C_{1-12}$alkoxy, thio, $C_{1-12}$alkylthio, carboxy, carboxy($C_{1-6}$alkyl), formyl, $C_{1-6}$alkylcarbonyl, $C_{1-6}$alkylsulfonyl, $C_{1-6}$alkylcarbonylalkoxy, nitro, trihalomethyl, trihaloalkoxy, trihalomethoxy, trihalomethyl($C_{1-6}$alkyl), hydroxy, hydroxy($C_{1-6}$)alkyl, ($C_{1-6}$alkoxy)carbonyl, amino, $C_{1-6}$alkylamino, di($C_{1-6}$alkyl)amino, aminocarboxy, $C_{1-6}$alkylaminocarboxy, di($C_{1-6}$alkyl)aminocarboxy, aminocarboxy($C_{1-6}$)alkyl, $C_{1-6}$alkylaminocarboxy($C_{1-6}$alkyl), di($C_{1-6}$alkyl)aminocarboxy($C_{1-6}$alkyl), $C_{1-6}$alkylcarbonylamino, $C_{1-6}$alkylcarbonyl($C_{1-6}$alkyl)amino, halo, $C_{1-6}$alkylhalo, sulphamoyl, tetrazolyl and cyano.

35. A compound as claimed in claim 33 wherein $R^2$ is phenyl, naphthyl, fluorenyl, thienyl, furanyl, pyrrolyl, imidazolyl, pyrazolyl, thiazolyl, isothiazolyl, oxazolyl, isoxazolyl, oxadiazolyl, thiadiazolyl, diazolyl, triazolyl, tetrazolyl, benzothiazolyl, benzimidazolyl, pyrrolinyl, imidazolinyl, pyranyl, pyronyl, pyridyl, pyrazinyl, pyridazinyl, thianaphthyl, benzofuranyl, isobenzofuranyl, benzothienyl, isobenzothienyl, indolyl, oxyindolyl, isoindolyl, indazolyl, indolinyl, 7-azaindolyl, azabenzimidazolyl, carbazolyl benzopyranyl, coumarinyl, isocoumarinyl, quinolinyl, isoquinolinyl, quinazolinyl, benzoxazinyl, quinoxalinyl, chromenyl, chromanyl, isochromanyl, phthalazinyl, benzodioxolyl, benzodioxanyl, cinnolinyl or carbolinyl optionally substituted with one or more substituents selected from $C_{1-2}$alkyl, $C_{1-12}$alkoxy, thio, $C_{1-12}$alkylthio, carboxy, carboxy($C_{1-6}$alkyl), formyl, $C_{1-6}$alkylcarbonyl, $C_{1-6}$alkylsulfonyl, $C_{1-6}$alkylcarbonylalkoxy, nitro, trihalomethyl, trihaloalkoxy, trihalomethoxy, trihalomethyl($C_{1-6}$alkyl), hydroxy, hydroxy($C_{1-6}$)alkyl, ($C_{1-6}$alkoxy)carbonyl, amino, $C_{1-6}$alkylamino, di($C_{1-6}$alkyl)amino, aminocarboxy, $C_{1-6}$alkylaminocarboxy, di($C_{1-6}$alkyl)aminocarboxy, aminocarboxy($C_{1-6}$)alkyl, $C_{1-6}$alkylaminocarboxy($C_{1-6}$alkyl), di($C_{1-6}$alkyl)aminocarboxy($C_{1-6}$alkyl), $C_{1-6}$alkylcarbonylamino, $C_{1-6}$alkylcarbonyl($C_{1-6}$alkyl)amino, halo, $C_{1-6}$alkylhalo, sulphamoyl, tetrazolyl and cyano.

36. A compound as claimed in claim 33 wherein $R^2$ is phenyl, thienyl, imidazolyl, oxazolyl, isoxazolyl, oxadiazolyl, thiadiazolyl, diazolyl, triazolyl, tetrazolyl, benzothiazolyl, benzimidazolyl, pyridyl, pyrazinyl, pyridazinyl, benzofuranyl, benzothienyl, or quinolinyl, optionally substituted with one or more substituents selected from $C_{1-2}$alkyl, $C_{1-12}$alkoxy, thio, $C_{1-12}$alkylthio, carboxy, carboxy($C_{1-6}$alkyl), formyl, $C_{1-6}$alkylcarbonyl, $C_{1-6}$alkylsulfonyl, $C_{1-6}$alkylcarbonylalkoxy, nitro, trihalomethyl, trihaloalkoxy, trihalomethoxy, trihalomethyl($C_{1-6}$alkyl), hydroxy, hydroxy($C_{1-6}$)alkyl, ($C_{1-6}$alkoxy)carbonyl, amino, $C_{1-6}$alkylamino, di($C_{1-6}$alkyl)amino, aminocarboxy, $C_{1-6}$alkylaminocarboxy, di($C_{1-6}$alkyl)aminocarboxy, aminocarboxy($C_{1-6}$)alkyl, $C_{1-6}$alkylaminocarboxy($C_{1-6}$alkyl), di($C_{1-6}$alkyl)aminocarboxy($C_{1-6}$alkyl), $C_{1-6}$alkylcarbonylamino, $C_{1-6}$alkylcarbonyl($C_{1-6}$alkyl)amino, halo, $C_{1-6}$alkylhalo, sulphamoyl, tetrazolyl and cyano.

37. A compound as claimed in claim 1
wherein:
$R^1$ is —H,
$C_{1-12}$alkyl optionally substituted with 1, 2 or 3 groups independently selected from halogen, hydroxyl, thiol, $C_{1-4}$alkoxy or $C_{1-4}$alkylthio, or
aryl-$C_{1-4}$alkyl;
$R^2$ is $(L)_a$-Z, wherein L is O, CO, $CH_2$, NH or $N(C_{1-4}$alkyl) and a is 0 or 1; and
Z is $C_{1-3}$alkyl-F, $C_{0-3}$alkyl-aryl-$R^6$, $C_{0-3}$alkyl-CO—$R^6$, $C_{0-3}$alkyl-CO—$NR^6_2$, $C_{0-3}$alkyl-$CO_2$—$R^6$, $C_{0-3}$alkyl-$SO_2$—$R^6$, $C_{0-3}$alkyl-$SO_2$—$NR^6_2$, $C_{1-3}$alkyl-$OR^6$, $C_{1-3}$alkyl-CN or $C_{1-3}$alkyl-$NR^6_2$ wherein each $C_{0-3}$alkyl or $C_{1-3}$alkyl portion is optionally substituted with from 1 to 6 groups selected from F and $C_{1-5}$alkyl,
$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;
$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$ alkyl, aryl, hydroxy, —$SO_2NH_2$, —$SO_2NHC_{1-4}$alkyl, or —$C_{1-4}$alkyl-OH;
$R^6$ is each independently H, $C_{1-6}$alkyl, aryl, or aryl$C_{1-4}$alkyl, each of which (except H) may be optionally substituted with from 1 to 3 fluorine atoms;
X is C;
W is C or N,
Y is C or N,
W' is C or N,
Y' is C or N,
provided that there are no more than two N atoms in the aryl ring,
r is 0, 1 or 2.

38. A compound as claimed in claim 37 wherein L is O, CO or $CH_2$.

39. A compound as claimed in claim 37 wherein L is NH or $N(C_{1-4}$alkyl).

40. A compound as claimed in claim 39 wherein Z is $C_{0-3}$alkyl-aryl-$R^6$, $C_{0-3}$alkyl-CO—$NR^6_2$, $C_{03}$alkyl-$CO_2$—$R^6$, $C_{1-3}$alkyl-$OR^6$ or $C_{1-3}$alkyl-$NR^6_2$ wherein each $C_{0-3}$alkyl or $C_{1-3}$alkyl portion is optionally substituted with from 1 to 6 groups selected from F and $C_{1-5}$alkyl.

41. A compound as claimed in claims 38 or 39 wherein Z is $C_{0-3}$alkyl-aryl-$R^6$, wherein aryl is selected from phenyl, naphthyl, fluorenyl, thienyl, furanyl, pyrrolyl, imidazolyl, pyrazolyl, thiazolyl, isothiazolyl, oxazolyl, isoxazolyl, oxadiazolyl, thiadiazolyl, diazolyl, triazolyl, tetrazolyl, benzothiazolyl, benzimidazolyl, pyrrolinyl, imidazolinyl, pyranyl, pyronyl, pyridyl, pyrazinyl, pyridazinyl, thianaphthyl, benzofuranyl, isobenzofuranyl, benzothienyl, isobenzothienyl, indolyl, oxyindolyl, isoindolyl, indazolyl, indolinyl, 7-azaindolyl, azabenzimidazolyl, carbazolyl benzopyranyl, coumarinyl, isocoumarinyl, quinolinyl, isoquinolinyl, quinazolinyl, benzoxazinyl, quinoxalinyl, chromenyl, chromanyl, isochromanyl, phthalazinyl, benzodioxolyl, benzodioxanyl, cinnolinyl or carbolinyl optionally, be substituted with one or more substituents selected from $C_1$ to $C_{12}$ alkyl (preferably $C_1$ to $C_6$ alkyl), $C_1$ to $C_{12}$ alkoxy (preferably $C_1$ to $C_6$ alkoxy), thio, $C_1$ to $C_{12}$ alkylthio (preferably $C_1$ to $C_6$ alkylthio), carboxy, carboxy($C_1$ to $C_6$)alkyl, formyl, $C_1$ to $C_6$ alkylcarbonyl, $C_1$ to $C_6$ alkylsulfonyl, $C_1$ to $C_6$ alkylcarbonylalkoxy, nitro, trihalomethyl, trihalo($C_1$ to $C_6$ alkoxy), trihalomethoxy, trihalomethyl($C_1$ to $C_6$ alkyl), hydroxy, hydroxy($C_1$ to $C_6$)alkyl, ($C_1$ to $C_6$ alkoxy)carbonyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy($C_1$ to $C_6$)alkyl, di($C_1$ to $C_6$ alkyl)aminocarboxy ($C_1$ to $C_6$)alkyl, $C_1$ to $C_6$ alkylcarbonylamino, $C_1$ to $C_6$ alkylcarbonyl($C_1$ to $C_6$ alkyl)amino, halo, $C_1$ to $C_6$ alkylhalo, sulphamoyl, tetrazolyl and cyano and wherein each $C_{0-3}$alkyl portion is optionally substituted with from 1 to 3 groups selected from F and $C_{1-3}$alkyl.

42. A compound as claimed in claims 38 or 39 wherein Z is $C_{1-3}$alkyl-CO—$NR^6_2$, wherein each $C_{1-3}$alkyl portion is optionally substituted with from 1 to 3 groups selected from F and $C_{1-3}$alkyl.

43. A compound as claimed in claims 38 or 39 wherein Z is $C_{1-3}$alkyl-$CO_2$—$R^6$, wherein each $C_{1-3}$alkyl portion is optionally substituted with from 1 to 3 groups selected from F and $C_{1-3}$alkyl.

44. A compound as claimed in claims 38 or 39 wherein Z is $C_{1-3}$alkyl-$OR^6$ wherein each $C_{1-3}$alkyl portion is optionally substituted with from 1 to 3 groups selected from F and $C_{1-3}$alkyl.

45. A compound as claimed in claims 38 or 39 wherein Z is $C_{0-3}$alkyl-$NR^6_2$ wherein each $C_{1-3}$alkyl portion is optionally substituted with from 1 to 3 groups selected from F and $C_{1-3}$alkyl.

46. A compound as claimed in any one of claims 37 to 39 wherein $R^6$ is/are each independently H, $C_{1-6}$alkyl, phenyl, or phenyl$C_{1-4}$alkyl, each of which (except H) may be optionally substituted with from 1 to 3 fluorine atoms.

47. A compound as claimed in any one of claims 37 to 39 wherein $R^6$ is/are each independently H, methyl, ethyl, propyl, cyclohexyl, or benzyl, each of which (except H) may be optionally substituted with 1, 2 or 3 fluorine atoms.

48. A compound as claimed in claim 1
wherein:
$R^1$ is —H,
$C_{1-12}$alkyl optionally substituted with 1, 2 or 3 groups independently selected from halogen, hydroxyl, thiol, $C_{1-4}$alkoxy or $C_{1-4}$alkylthio, or
aryl-$C_{1-4}$alkyl;
$R^2$ is linked back to the aromatic ring so as to form a fused bicyclic compound represented by Formula (Ia)

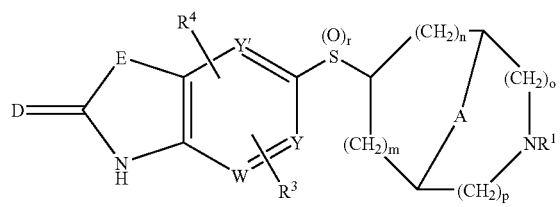

(Ia)

wherein D is O or S; and
E is O, S, $NR^5$, or $C(R^5)_2$,
$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$ alkyl, aryl, hydroxy, —$SO_2NH_2$, —$SO_2NHC_{1-4}$alkyl, or —$C_{1-4}$alkyl-OH;
$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

$R^5$ is each independently H or $C_{1-4}$alkyl;

X is C;

W is C or N;

Y is C or N;

Y' is C or N;

provided that there are no more than two N atoms in the aryl ring, r is 0, 1 or 2.

49. A compound as claimed in claim 48 wherein E is O or $NR^5$.

50. A compound as claimed in claim 48 or 49 wherein $R^5$ is/are each independently H or $C_{1-4}$alkyl.

51. A compound as claimed in claim 1 wherein:

$R^1$ is —H, $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;

$R^2$ is linked back to the aromatic ring so as to form a fused bicyclic compound represented by Formula (Ia)

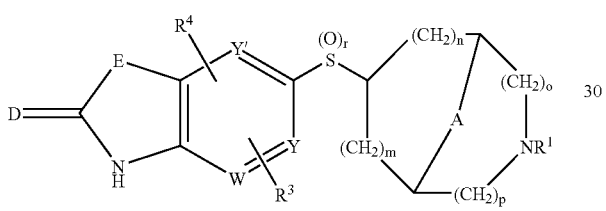

(Ia)

wherein D is O or S; and

E is O—$CR^5_2$, $NR^5$—$CR^5_2$, $NR^5$—CO, $CR^5_2$—O, $CR^5_2$—$S(O)_r$, $CR^5_2$—$NR^5$, $CR^5_2$—$CR^5_2$, CO—$NR^5$, or $CR^5$=$CR^5$;

$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

$R^5$ is each independently H, $C_{1-4}$alkyl;

X is C;

W is C or N;

Y is C or N;

Y' is C or N;

provided that there are no more than two N atoms in the aryl ring;

r is 0, 1 or 2.

52. A compound as claimed in claim 51 wherein E is O—$CR^5_2$, $NR^5$—$CR^5_2$, $NR^5$—CO, $CR^5_2$—$CR^5_2$, or $CR^5$=$CR^5$.

53. A compound as claimed in claim 51 or 52 wherein E is O—$CR^5_2$, $NR^5$—CO, or $CR^5$=$CR^5$.

54. A compound as claimed in claim 53 wherein $R^5$ is/are each independently H or $C_{1-4}$alkyl.

55. A compound as claimed in claim 1 wherein:

$R^1$ is —H, $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;

$R^2$ is linked back to the aromatic ring so as to form a fused bicyclic compound represented by Formula (Ib)

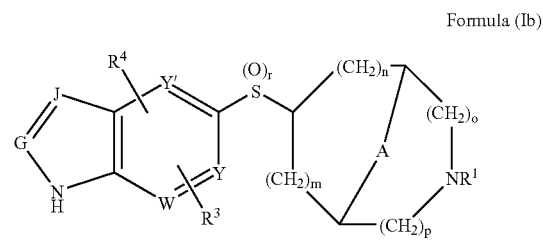

Formula (Ib)

wherein G is $CR^5$ or N; and

J is $CR^5$ or N;

$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

$R^5$ is each independently H or $C_{1-4}$alkyl;

X is C;

W is C or N;

Y is C or N;

Y' is C or N provided that there are no more than two N atoms in the aryl ring;

r is 0, 1 or 2.

56. A compound as claimed in claim 55 wherein each $R^5$ is H.

57. A compound as claimed in claims 1, 48, 51 or 55 wherein r is 0.

58. A compound as claimed in claims 1, 48, 51 or 55 wherein r is 2.

59. A compound as claimed in any one of claims 1, 48, 51 or 55 wherein $R^1$ is H or $C_{1-3}$alkyl.

60. A compound as claimed in any one of claims 1, 48, 51 or 55 wherein $R^3$ is H, halogen, $C_{1-4}$alkyl, $CF_3$, or $OC_{1-4}$alkyl, and $R^4$ is H, halogen, $C_{1-4}$alkyl, $CF_3$, or $OC_{1-4}$alkyl.

61. A compound as claimed in any one of claims 1, 48, 51 or 55 wherein one or both of $R^3$ and $R^4$ are positioned ortho to the $S(O)_r$ moeity.

62. A pharmaceutical composition comprising a therapeutically effective amount of a compound as claimed in any one of claims 1, 48, 51 or 55 with a pharmaceutically acceptable diluent or carrier.

* * * * *